United States Patent
Lee et al.

(10) Patent No.: US 11,472,800 B2
(45) Date of Patent: Oct. 18, 2022

(54) ORGANIC COMPOUND AND ORGANIC ELECTROLUMINESCENT DEVICE COMPRISING THE SAME

(71) Applicant: DOOSAN SOLUS CO., LTD., Iksan-si (KR)

(72) Inventors: Yong Hwan Lee, Yongin-si (KR); Jae Yi Sim, Yongin-si (KR)

(73) Assignee: DOOSAN SOLUS CO., LTD., Iksan-si (KR)

(*) Notice: Subject to any disclaimer, the term of this patent is extended or adjusted under 35 U.S.C. 154(b) by 474 days.

(21) Appl. No.: 16/345,593

(22) PCT Filed: Oct. 16, 2017

(86) PCT No.: PCT/KR2017/011368
§ 371 (c)(1),
(2) Date: Apr. 26, 2019

(87) PCT Pub. No.: WO2018/080068
PCT Pub. Date: May 3, 2018

(65) Prior Publication Data
US 2019/0263806 A1    Aug. 29, 2019

(30) Foreign Application Priority Data
Oct. 27, 2016   (KR) .................... 10-2016-0141056

(51) Int. Cl.
*H01L 51/00* (2006.01)
*C07D 471/04* (2006.01)
(Continued)

(52) U.S. Cl.
CPC ......... *C07D 471/04* (2013.01); *C07D 471/14* (2013.01); *C07D 487/04* (2013.01);
(Continued)

(58) Field of Classification Search
None
See application file for complete search history.

(56) References Cited

U.S. PATENT DOCUMENTS

| 6,551,723 B1 * | 4/2003 | Okada .................. H01L 51/004 313/504 |
| 2011/0284799 A1 * | 11/2011 | Stoessel .................. C07F 19/00 252/301.16 |

FOREIGN PATENT DOCUMENTS

| CN | 101792457 A | * 4/2010 | ........... C07D 519/00 |
| CN | 106749234 A | 5/2017 | |

(Continued)

OTHER PUBLICATIONS

Smirnova et al. "2-Dicyanomethylidene-3-ethoxymethylidene-2,3-dihydroindole in the synthesis of fused tri- and tetracyclic systmes" Russian Chemical Bulletin, International Edition, 59(1), 2010, 177-185. (Year: 2010).*

(Continued)

*Primary Examiner* — Robert S Loewe
(74) *Attorney, Agent, or Firm* — Sughrue Mion, PLLC

(57) ABSTRACT

The present invention relates to a novel compound and an organic electroluminescent device including the same, and the compound according to the present invention is used in an organic material layer of an organic electroluminescent device, preferably an electron transport layer or a hole blocking layer, and may increase luminous efficiency, driving voltage and lifespan of the organic electroluminescent device.

12 Claims, 1 Drawing Sheet

(51) Int. Cl.
  *C07D 471/14* (2006.01)
  *C07D 487/04* (2006.01)
  *C07D 491/147* (2006.01)
  *C07D 495/14* (2006.01)
  *H01L 51/50* (2006.01)
  *C09K 11/06* (2006.01)
  *C07D 491/153* (2006.01)
  *C07D 487/14* (2006.01)

(52) U.S. Cl.
  CPC ....... *C07D 487/14* (2013.01); *C07D 491/147* (2013.01); *C07D 491/153* (2013.01); *C07D 495/14* (2013.01); *C09K 11/06* (2013.01); *H01L 51/00* (2013.01); *H01L 51/0054* (2013.01); *H01L 51/0058* (2013.01); *H01L 51/0059* (2013.01); *H01L 51/0067* (2013.01); *H01L 51/0072* (2013.01); *H01L 51/50* (2013.01); *H01L 51/5096* (2013.01); *H01L 51/5072* (2013.01)

(56) References Cited

FOREIGN PATENT DOCUMENTS

| | | |
|---|---|---|
| CN | 106967065 A | 7/2017 |
| CN | 109071555 | 12/2018 |
| KR | 10-2012-0029258 A | 3/2012 |
| KR | 10-2014-0075084 A | 6/2014 |
| KR | 10-2014-0080685 | 7/2014 |
| KR | 10-2017-0002209 A | 6/2017 |
| KR | 10-2017-0076292 A | 7/2017 |
| WO | 2013/090771 A1 | 6/2013 |

OTHER PUBLICATIONS

Machine translation of KR-1020140080685, translation generated Jul. 2021, 24 pages. (Year: 2021).*
Wang et al. "Synthesis of unprecedented benzofused [1, 2, 4]-triazoloquinazolines via benzyne Diels-Alder reaction with 7-vinyl-[1, 2, 4] triazolo [1,5-c] pyrimidines as dienes." Synlett 26, No. 07 (2015): 931-936. (Year: 2015).*
Chinese Patent Office, Communication dated Mar. 12, 2021 in Chinese Application No. 201780066461.0, with English translation.
International Search Report for PCT/KR2017/011368 dated Feb. 14, 2018 (PCT/ISA/210).

* cited by examiner

【FIG. 1】
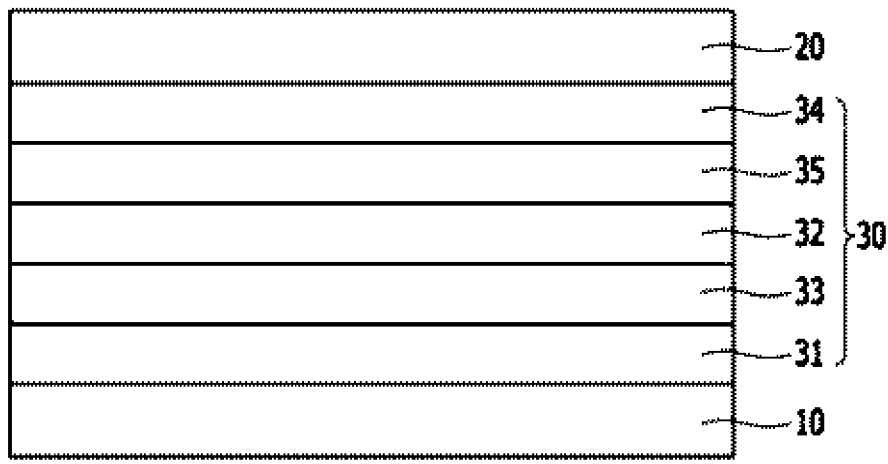
【FIG. 2】
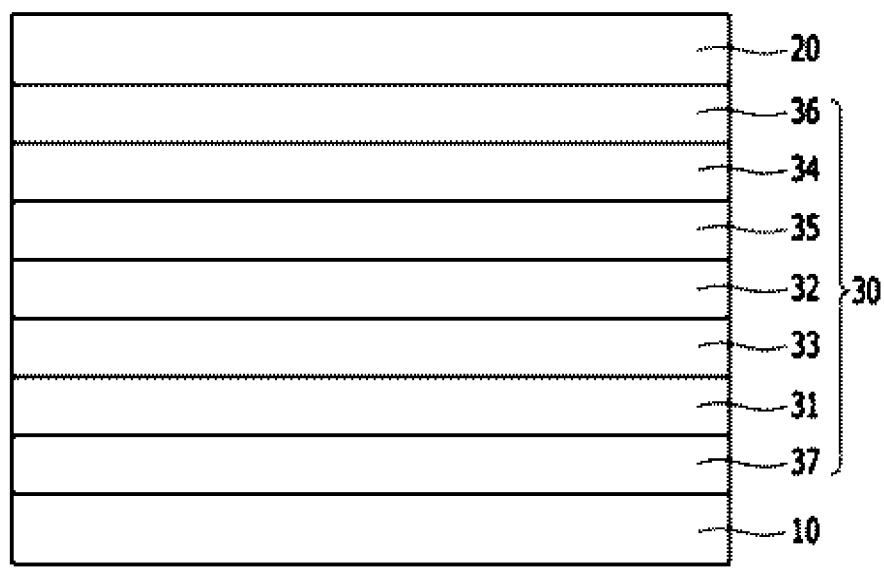

ORGANIC COMPOUND AND ORGANIC ELECTROLUMINESCENT DEVICE COMPRISING THE SAME

CROSS REFERENCE TO RELATED APPLICATIONS

This application is a National Stage of International Application No. PCT/KR2017/011368 filed Oct. 16, 2017, claiming priority based on Korean Patent Application No. 10-2016-0141056, filed Oct. 27, 2016.

TECHNICAL FIELD

The present invention relates to a novel organic compound capable of being used as a material for an organic electroluminescent device, and an organic electroluminescent device including the same.

BACKGROUND ART

With the observation of organic thin film light emission made by Bemanose in 1950s as a start, studies on organic electroluminescent (EL) devices have been continued leading to blue electroluminescence using a single anthracene crystal in 1965, and in 1987, an organic electroluminescent device having a laminated structure divided into functional layers of a hole layer and a light emitting layer has been proposed by Tang. After that in order to manufacture organic electroluminescent devices with high efficiency and long lifespan, development has been made in the form of introducing each characteristic organic material layer into the device, which leads to the development of specialized materials used therein.

When a voltage is applied between the two electrodes in an organic electroluminescent device, holes and electrons are injected to an organic material layer from the anode and the cathode, respectively. When the injected holes and electrons meet, excitons are formed, and light emits when these excitons fall back to the ground state. Herein, materials used as the organic material layer may be divided into a light emitting material, a hole injection material, a hole transport material, an electron transport material, an electron injection material and the like depending on the function.

The light emitting material may be divided into, depending on the light emitting color, blue, green and red light emitting materials, and yellow and orange light emitting materials for obtaining better natural colors. In addition, in order to increase color purity and increase luminous efficiency through energy transfer, host/dopant series may be used as the light emitting material.

The dopant material may be divided into fluorescent dopants using organic materials and phosphorescent dopants using metal complex compounds including heavy atoms such as Ir or Pt. Herein, development of phosphorescent materials may enhance luminous efficiency up to 4 times compared to fluorescence theoretically, and therefore, studies on phosphorescent host materials have been widely progressed as well as on phosphorescent dopants.

So far, NPB, BCP, Alq$_3$ and the like have been widely known as materials of a hole injection layer, a hole transport layer, a hole blocking layer and an electron transport layer, and anthracene derivatives have been reported as a material of a light emitting layer. Particularly, among light emitting layer materials, metal complex compounds including Ir such as Firpic, Ir(ppy)$_3$ or (acac)Ir(btp)$_2$ having advantages in terms of efficiency enhancement have been used as blue, green and red phosphorescent dopant materials, and 4,4-dicarbazolylbiphenyl (CBP) has been used as a phosphorescent host material.

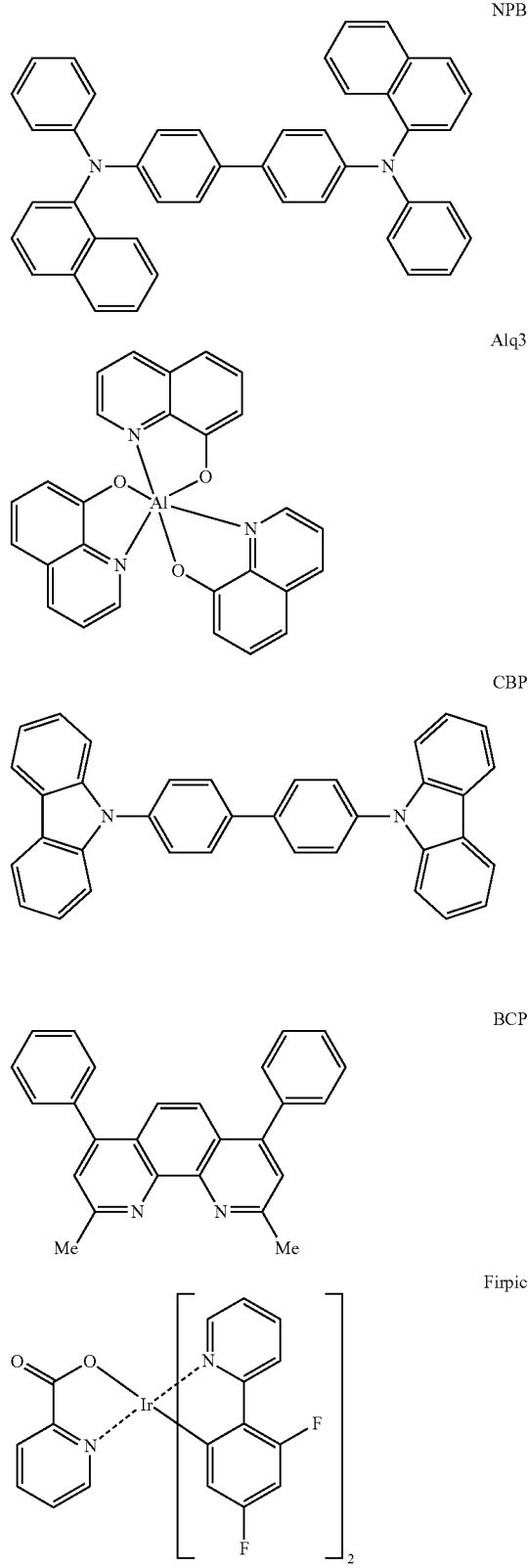

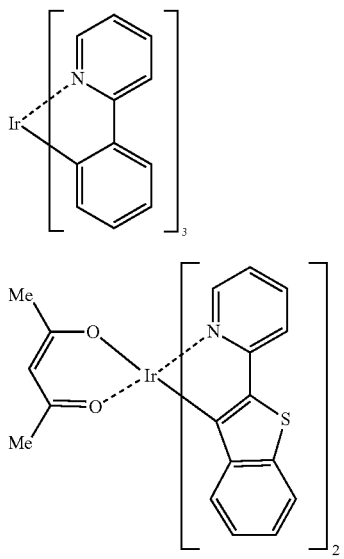

However, although being advantageous in terms of a light emission property, existing organic material layer materials have a low glass transition temperature and thereby have very unfavorable thermal stability, which is not satisfactory in terms of an organic electroluminescent device lifespan. Accordingly, development of organic material layer materials having superior performance has been required.

DISCLOSURE

Technical Problem

The present invention is directed to providing a novel organic compound capable of being used in an organic electroluminescent device, and having excellent hole and electron injection and transport abilities, a light emitting ability and the like.

The present invention is also directed to providing an organic electroluminescent device including the new organic compound, and thereby exhibiting a low driving voltage, high luminous efficiency, and an enhanced lifespan.

Technical Solution

In view of the above, one embodiment of the present invention provides a compound represented by the following Chemical Formula 1:

[Chemical Formula 1]

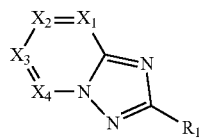

in Chemical Formula 1,
$X_1$ to $X_4$ are each independently N or $C(R_2)$;
$R_1$ and $R_2$ are each independently a substituent represented by the following Chemical Formula 2, and when $R_2$ is present in plural numbers, these are the same as or different from each other;

[Chemical Formula 2]

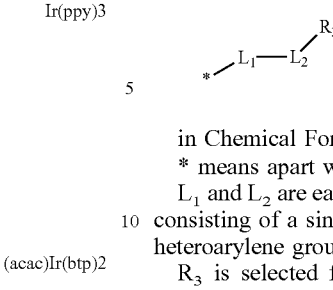

in Chemical Formula 2,
* means apart where a bond is formed;
$L_1$ and $L_2$ are each independently selected from the group consisting of a single bond, a $C_6$~$C_{18}$ arylene group and a heteroarylene group having 5 to 18 nuclear atoms;
$R_3$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, or bonds to an adjacent group to form an aromatic ring having 5 to 50 nuclear atoms, a non-aromatic fused polycyclic ring having 5 to 50 nuclear atoms, an aromatic heteroring having 5 to 50 nuclear atoms, or a non-aromatic fused heteropolycyclic ring having 5 to 50 nuclear atoms; and the arylene group and the heteroarylene group of $L_1$ and $L_2$, the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_3$, and the aromatic ring, the non-aromatic fused polycyclic ring, the aromatic heteroring and the non-aromatic fused heteropolycyclic ring formed by adjacent two $R_3$s bonding to each other are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

Another embodiment of the present invention provides an organic electroluminescent device including an anode, a cathode, and one or more organic material layers provided between the anode and the cathode, wherein at least one of the one or more organic material layers includes the compound of Chemical Formula 1.

In the present invention, the "alkyl" is a monovalent substituent derived from linear or branched saturated hydrocarbon having 1 to 40 carbon atoms. Examples thereof may include methyl, ethyl, propyl, isobutyl, sec-butyl, pentyl, iso-amyl, hexyl and the like, but are not limited thereto.

In the present invention, the "alkenyl" is a monovalent substituent derived from linear or branched unsaturated hydrocarbon having one or more carbon-carbon double bonds and having 2 to 40 carbon atoms. Examples thereof may include vinyl, allyl, isopropenyl, 2-butenyl and the like, but are not limited thereto.

In the present invention, the "alkynyl" is a monovalent substituent derived from linear or branched unsaturated hydrocarbon having one or more carbon-carbon triple bonds and having 2 to 40 carbon atoms. Examples thereof may include ethynyl, 2-propynyl and the like, but are not limited thereto.

In the present invention, the "aryl" means a monovalent substituent derived from aromatic hydrocarbon having a single ring or two or more rings combined and having 6 to 60 carbon atoms. In addition, a monovalent substituent having two or more rings fused with each other, including only carbon (for example, the number of carbon atoms may be from 8 to 60) as a ring-forming atom, and with the whole molecule having non-aromaticity may also be included. Examples of such aryl may include phenyl, naphthyl, phenanthryl, anthryl, fluorenyl and the like, but are not limited thereto.

In the present invention, the "heteroaryl" means a monovalent substituent derived from monoheterocyclic or polyheterocyclic aromatic hydrocarbon having 5 to 60 nuclear atoms. Herein, one or more carbons, preferably 1 to 3 carbons, in the ring are substituted with a heteroatom selected from among N, O, P, S and Se. In addition, a monovalent group having two or more rings simply attached (pendant) or fused with each other, including a heteroatom selected from among N, O, P, S and Se as a ring-forming atom in addition to carbon, and with the whole molecule having non-aromaticity is interpreted to be included as well. Examples of such heteroaryl may include 6-membered monocyclic rings such as pyridyl, pyrazinyl, pyrimidinyl, pyridazinyl or triazinyl; polycyclic rings such as phenoxathienyl, indolizinyl, indolyl, purinyl, quinolyl, benzothiazole or carbazolyl; 2-furanyl, N-imidazolyl, 2-isoxazolyl, 2-pyridinyl, 2-pyrimidinyl and the like, but are not limited thereto.

In the present invention, the "aryloxy" is a monovalent substituent represented by RO—, and R means aryl having 5 to 60 carbon atoms. Examples of such aryloxy may include phenyloxy, naphthyloxy, diphenyloxy and the like, but are not limited thereto.

In the present invention, the "alkyloxy" is a monovalent substituent represented by R'O—, and R' means alkyl having 1 to 40 carbon atoms and is interpreted to include a linear, branched or cyclic structure. Examples of such alkyloxy may include methoxy, ethoxy, n-propoxy, 1-propoxy, t-butoxy, n-butoxy, pentoxy and the like, but are not limited thereto.

In the present invention, the "arylamine" means amine substituted with aryl having 6 to 60 carbon atoms.

In the present invention, the "cycloalkyl" means a monovalent substituent derived from monocyclic or polycyclic non-aromatic hydrocarbon having 3 to 40 carbon atoms. Examples of such cycloalkyl may include cyclopropyl, cyclopentyl, cyclohexyl, norbomyl, adamantine and the like, but are not limited thereto.

In the present invention, the "heterocycloalkyl" means a monovalent substituent derived from non-aromatic hydrocarbon having 3 to 40 nuclear atoms, and one or more carbons, preferably 1 to 3 carbons, in the ring are substituted with a heteroatom such as N, O, S or Se. Examples of such heterocycloalkyl may include morpholine, piperazine and the like, but are not limited thereto.

In the present invention, the "alkylsilyl" means silyl substituted with alkyl having 1 to 40 carbon atoms, and the "arylsilyl" means silyl substituted with aryl having 5 to 60 carbon atoms.

In the present invention, the "aromatic ring" means a monovalent substituent derived from aromatic hydrocarbon having a single ring or two or more rings combined and having 6 to 60 carbon atoms. Examples of such an aromatic ring may include phenyl, naphthyl, phenanthrenyl, anthrenyl and the like, but are not limited thereto.

In the present invention, the "non-aromatic fused polycyclic ring" means a monovalent group (for example, having 8 to 60 carbon atoms) having two or more rings fused with each other, including only carbon as a ring-forming atom, and with the whole molecule having non-aromaticity. Examples of the non-aromatic fused polycyclic ring may include a fluorenyl group and the like, but are not limited thereto.

In the present invention, the "aromatic heteroring" means monoheterocyclic or polyheterocyclic aromatic hydrocarbon having 5 to 60 nuclear atoms. Herein, one or more carbons, preferably 1 to 3 carbons, in the ring are substituted with a heteroatom selected from among N, O, P, S and Se. In addition, 2 or more ring are simply attached (pendant) or fused with each other, and a heteroatom selected from among N, O, P, S and Se is included as a ring-forming atom in addition to carbon. Examples of such heteroaryl may include a 6-membered monocyclic ring such as pyridyl, pyrazinyl, pyrimidinyl, pyridazinyl or triazinyl; a polycyclic ring such as phenoxathienyl, indolizinyl, indolyl, purinyl, quinolyl, benzothiazole or carbazolyl; 2-furanyl, N-imidazolyl, 2-isoxazolyl, 2-pyridinyl, 2-pyrimidinyl and the like, but are not limited thereto.

In the present invention, the "non-aromatic fused heteropolycyclic ring" means a group (for example, having 2 to 60 carbon atoms) having two or more rings fused with each other, including a heteroatom selected from among N, O, P and S as a ring-forming atom in addition to carbon, and with the whole molecule having non-aromaticity. Examples of the non-aromatic fused heteropolycyclic ring may include a carbazolyl group and the like, but are not limited thereto.

In the present invention, the "fused ring" means a fused aliphatic ring, a fused aromatic ring, a fused heteroaliphatic ring, a fused heteroaromatic ring, or a combined form thereof.

Advantageous Effects

A compound of the present invention has excellent thermal stability, carrier transport ability, light emitting ability and the like, and therefore, is useful as a material of an organic material layer of an organic electroluminescent device.

In addition, an organic electroluminescent device including a compound of the present invention in an organic material layer exhibits greatly enhanced properties in terms of light emitting performance, driving voltage, lifespan, efficiency and the like, and can be effectively used in a full color display panel and the like.

DESCRIPTION OF DRAWINGS

FIG. 1 is a sectional diagram illustrating an organic electroluminescent device according to one embodiment of the present invention.

FIG. 2 is a sectional diagram illustrating an organic electroluminescent device according to one embodiment of the present invention.
10: Anode
20: Cathode
30: Organic Layer
31: Hole Transport Layer
32: Light Emitting Layer
33: Electron Blocking Layer
34: Electron Transport Layer
35: Hole Blocking Layer
36: Electron Injection Layer
37: Hole Injection Layer

MODE FOR DISCLOSURE

A novel compound of the present invention may be represented by the following Chemical Formula 1:

[Chemical Formula 1]

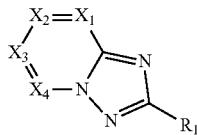

in Chemical Formula 1, $X_1$ to $X_4$ are each independently N or $C(R_2)$;

$R_1$ and $R_2$ are each independently a substituent represented by the following Chemical Formula 2, and when $R_2$ is present in plural numbers, these are the same as or different from each other;

[Chemical Formula 2]

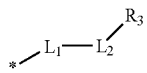

in Chemical Formula 2,

* means a part where a bond is formed;

$L_1$ and $L_2$ are each independently selected from the group consisting of a single bond, a $C_6$~$C_{18}$ arylene group and a heteroarylene group having 5 to 18 nuclear atoms;

$R_3$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, or bonds to an adjacent group to form an aromatic ring having 5 to 50 nuclear atoms, a non-aromatic fused polycyclic ring having 5 to 50 nuclear atoms, an aromatic heteroring having 5 to 50 nuclear atoms, or a non-aromatic fused heteropolycyclic ring having 5 to 50 nuclear atoms; and the arylene group and the heteroarylene group of $L_1$ and $L_2$, the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_3$, and the aromatic ring, the non-aromatic fused polycyclic ring, the aromatic heteroring and the non-aromatic fused heteropolycyclic ring formed by adjacent two $R_3$s bonding to each other are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

Hereinafter, the present invention will be described in detail.

Novel Organic Compound

A novel compound of the present invention may be represented by the following Chemical Formula 1:

[Chemical Formula 1]

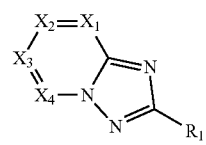

in Chemical Formula 1, $X_1$ to $X_4$ are each independently N or $C(R_2)$;

$R_1$ and $R_2$ are each independently a substituent represented by the following Chemical Formula 2, and when $R_2$ is present in plural numbers, these are the same as or different from each other;

[Chemical Formula 2]

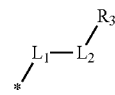

in Chemical Formula 2,

* means a part where a bond is formed;

$L_1$ and $L_2$ are each independently selected from the group consisting of a single bond, a $C_6$~$C_{18}$ arylene group and a heteroarylene group having 5 to 18 nuclear atoms;

$R_3$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, or bonds to an adjacent group to form an aromatic ring having 5 to 50 nuclear atoms, a non-aromatic fused polycyclic ring having 5 to 50 nuclear atoms, an aromatic heteroring having 5 to 50 nuclear atoms, or a non-aromatic fused heteropolycyclic ring having 5 to 50 nuclear atoms; and the arylene group and the heteroarylene group of $L_1$ and $L_2$, the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_3$, and the aromatic ring, the non-aromatic fused polycyclic ring, the aromatic heteroring and the non-aromatic fused heteropolycyclic ring formed by adjacent two $R_3$s bonding to each other are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

In the present invention, the compound represented by Chemical Formula 1 has excellent electron withdrawing group (EWG) properties, is more electrochemically stable compared to a 6-membered heteroring structure known in the art and has excellent electron mobility, and in addition thereto, has a high glass transition temperature and excellent thermal stability. Accordingly, the compound represented by Chemical Formula 1 of the present invention has excellent electron transport ability and light emission property, and may be used as a material of any one of a hole injection layer, a hole transport layer, a light emitting layer, an electron transport layer and an electron injection layer that are organic material layers of an organic electroluminescent device. The compound represented by Chemical Formula 1 of the present invention may be preferably used as a material of any one of a light emitting layer, an electron transport layer, and a hole blocking layer further laminated on the electron transport layer, and more preferably used as a material of an electron transport layer or a hole blocking layer.

Accordingly, when used in an organic electroluminescent device, the compounds having the structure of Chemical Formula 1 of the present invention may be expected to have excellent thermal stability and carrier transport ability (particularly, electron transport ability and light emitting ability, and in addition thereto, may have enhanced driving voltage, efficiency, lifespan and the like of a device, and may exhibit an excellent efficiency increase as a material of a latest organic electroluminescent device by high triplet energy.

According to preferred one embodiment of the present invention, the compound represented by Chemical Formula 1 may be a compound represented by any one of the following Chemical Formulae 3 to 6:

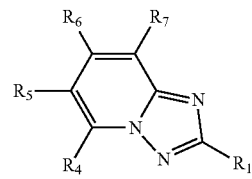

[Chemical Formula 3]

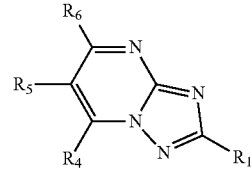

[Chemical Formula 4]

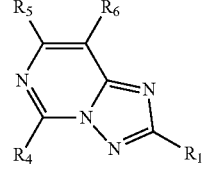

[Chemical Formula 5]

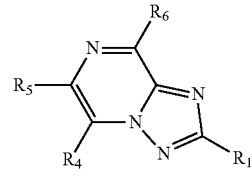

[Chemical Formula 6]

in Chemical Formulae 3 to 6, $R_1$ and $R_4$ to $R_7$ may be each independently the substituent represented by Chemical Formula 2.

According to preferred one embodiment of the present invention, one or more of $R_4$ and $R_5$, $R_5$ and $R_6$, and $R_6$ and $R_7$ bond to each other to form an aromatic ring having 5 to 50 nuclear atoms, a non-aromatic fused polycyclic ring having 5 to 50 nuclear atoms, an aromatic heteroring having 5 to 50 nuclear atoms, or anon-aromatic fused heteropolycyclic ring having 5 to 50 nuclear atoms; and the aromatic ring, the non-aromatic fused polycyclic ring, the aromatic heteroring and the non-aromatic fused heteropolycyclic ring formed by $R_4$ and $R_5$, $R_5$ and $R_6$, and $R_6$ and $R_7$ bonding to each other are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_1$~$C_{40}$ alkylsulfonyl group, a $C_6$~$C_{60}$ arylsulfonyl group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

According to preferred one embodiment of the present invention, in the compounds represented by Chemical Formulae 3 to 6, one or more of $R_4$ and $R_5$, $R_5$ and $R_6$, and $R_6$ and $R_7$ may each independently form a fused ring with a ring represented by any one of the following Chemical Formulae 7 to 11:

[Chemical Formula 7]

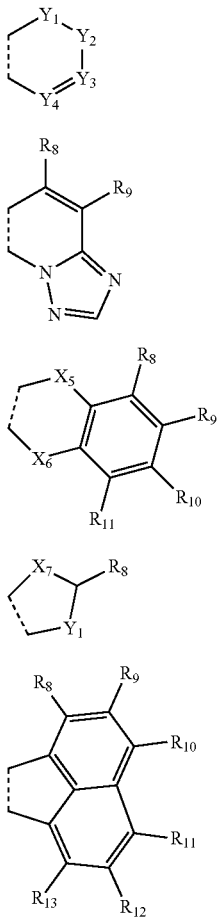

[Chemical Formula 8]

[Chemical Formula 9]

[Chemical Formula 10]

[Chemical Formula 11]

in Chemical Formulae 7 to 11, a dotted line means a part that is fused;

$Y_1$ to $Y_4$ are each independently N or $C(Ar_1)$, and when $Ar_1$ is present in plural numbers, these are the same as or different from each other;

$X_5$ and $X_6$ are each independently selected from the group consisting of a single bond, O, N, a $C(Ar_2)(Ar_3)$, S, $Si(Ar_4)(Ar_5)$ and $P(=O)(Ar_6)$, however, $X_5$ and $X_6$ are not both a single bond;

$X_7$ is O, $N(Ar_7)$ or S;

$Ar_1$ to $Ar_7$ and $R_8$ to $R_{13}$ are each independently a substituent represented by the following Chemical Formula 12;

[Chemical Formula 12]

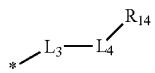

in Chemical Formula 12,

* means a part where a bond is formed;

$L_3$ and $L_4$ are each independently selected from the group consisting of a single bond, a $C_6 \sim C_{18}$ arylene group and a heteroarylene group having 5 to 18 nuclear atoms;

$R_{14}$ is selected from the group consisting of hydrogen, deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_3 \sim C_{40}$ cycloalkyl group, a heterocycloalkyl group having 3 to 40 nuclear atoms, a $C_6 \sim C_{60}$ aryl group, a heteroaryl group having 5 to 60 nuclear atoms, a $C_1 \sim C_{40}$ alkyloxy group, a $C_6 \sim C_{60}$ aryloxy group, a $C_3 \sim C_{40}$ alkylsilyl group, a $C_6 \sim C_{60}$ arylsilyl group, a $C_1 \sim C_{40}$ alkylsulfonyl group, a $C_6 \sim C_{60}$ arylsulfonyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group, a $C_1 \sim C_{40}$ alkylcarbonyl group, a $C_6 \sim C_{60}$ arylcarbonyl group and a $C_6 \sim C_{60}$ arylamine group, or bonds to an adjacent group to form an aromatic ring having 5 to 50 nuclear atoms, a non-aromatic fused polycyclic ring having 5 to 50 nuclear atoms, an aromatic heterorring having 5 to 50 nuclear atoms, or a non-aromatic fused heteropolycyclic ring having 5 to 50 nuclear atoms; and the arylene group and the heteroarylene group of $L_3$ and $L_4$, the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_{14}$, and the aromatic ring, the non-aromatic fused polycyclic ring, the aromatic heteroring and the non-aromatic fused heteropolycyclic ring formed by adjacent two substituents bonding to each other are each independently unsubstituted or substituted with one or more types of substituents selected from the group consisting of deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_6 \sim C_{60}$ aryl group, a heteroaryl group having 5 to 60 nuclear atoms, a $C_6 \sim C_{60}$ aryloxy group, a $C_1 \sim C_{40}$ alkyloxy group, a $C_6 \sim C_{60}$ arylamine group, a $C_3 \sim C_{40}$ cycloalkyl group, a heterocycloalkyl group having 3 to 40 nuclear atoms, a $C_1 \sim C_{40}$ alkylsilyl group, a $C_1 \sim C_{40}$ alkylsulfonyl group, a $C_6 \sim C_{60}$ arylsulfonyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group, a $C_1 \sim C_{40}$ alkylcarbonyl group, a $C_6 \sim C_{60}$ arylcarbonyl group and a $C_6 \sim C_{60}$ arylsilyl group, and when substituted with a plurality of the substituents, these are the same as or different from each other.

According to preferred one embodiment of the present invention, the ring represented by Chemical Formula 7 may be represented by the following Chemical Formula 13 or 14:

[Chemical Formula 13]

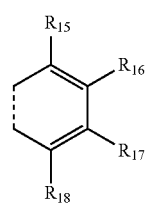

[Chemical Formula 14]

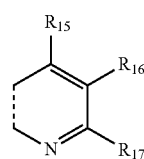

in Chemical Formulae 13 and 14, a dotted line means a part that is fused;

$R_{15}$ to $R_{18}$ are each independently a substituent represented by the following Chemical Formula 15;

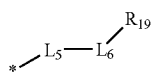

[Chemical Formula 15]

in Chemical Formula 15,

* means a part where a bond is formed;

$L_5$ and $L_6$ are each independently selected from the group consisting of a single bond, a $C_6$~$C_{18}$ arylene group and a heteroarylene group having 5 to 18 nuclear atoms;

$R_{19}$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, or bonds to an adjacent group to form an aromatic ring having 5 to 50 nuclear atoms, a non-aromatic fused polycyclic ring having 5 to 50 nuclear atoms, an aromatic heteroring having 5 to 50 nuclear atoms, or a non-aromatic fused heteropolycyclic ring having 5 to 50 nuclear atoms; and the arylene group and the heteroarylene group of $L_5$ and $L_6$, the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_{19}$, and the aromatic ring, the non-aromatic fused polycyclic ring, the aromatic heteroring and the non-aromatic fused heteropolycyclic ring formed by adjacent two substituents bonding to each other are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

According to preferred one embodiment of the present invention, in the rings represented by Chemical Formulae 13 and 14, one or more of $R_{15}$ and $R_{16}$, $R_{16}$ and $R_{17}$, and $R_{17}$ and $R_{18}$ may each independently form a fused ring with a ring represented by the following Chemical Formula 16:

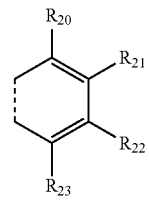

[Chemical Formula 16]

in Chemical Formula 16,
a dotted line means a part that is fused;
$R_{20}$ to $R_{23}$ are each independently a substituent represented by the following Chemical Formula 17;

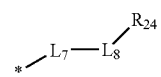

[Chemical Formula 17]

in Chemical Formula 17,

* means a part where a bond is formed;

$L_7$ and $L_8$ are each independently selected from the group consisting of a single bond, a $C_6$~$C_{18}$ arylene group and a heteroarylene group having 5 to 18 nuclear atoms;

$R_{24}$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group; and the arylene group and the heteroarylene group of $L_7$ and $L_8$, and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_{24}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

According to preferred one embodiment of the present invention, in the ring represented by Chemical Formula 8, $R_8$ and $R_9$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group, the alkylcarbonyl group, the arylcarbonyl group and the arylsilyl group of $R_8$ and $R_9$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

According to preferred one embodiment of the present invention, the ring represented by Chemical Formula 8 may be represented by the following Chemical Formula 18:

[Chemical Formula 18]

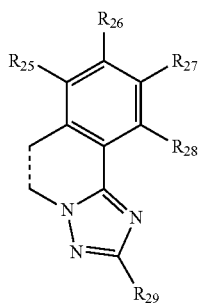

in Chemical Formula 18,
a dotted line means a part that is fused;
$R_{25}$ to $R_{29}$ are each independently a substituent represented by the following Chemical Formula 15;

[Chemical Formula 15]

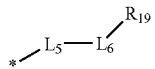

in Chemical Formula 15,
* means a part where a bond is formed;
$L_5$ and $L_6$ are each independently selected from the group consisting of a single bond, a $C_6$~$C_{18}$ arylene group and a heteroarylene group having 5 to 18 nuclear atoms;

$R_{19}$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, or bonds to an adjacent group to form an aromatic ring having 5 to 50 nuclear atoms, a non-aromatic fused polycyclic ring having 5 to 50 nuclear atoms, an aromatic heterring having 5 to 50 nuclear atoms, or a non-aromatic fused heteropolycyclic ring having 5 to 50 nuclear atoms; and the arylene group and the heteroarylene group of $L_5$ and $L_6$, the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_{19}$, and the aromatic ring, the non-aromatic fused polycyclic ring, the aromatic heterring and the non-aromatic fused heteropolycyclic ring formed by adjacent two substituents bonding to each other are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

According to preferred one embodiment of the present invention, in the ring represented by Chemical Formula 9, any one of $X_5$ and $X_6$ is a single bond, and the other one is O, N, a $C(Ar_2)(Ar_3)$, S, $Si(Ar_4)(Ar_5)$ or $P(=O)(Ar_6)$;

herein, $Ar_2$ to $Ar_6$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1 \sim C_{40}$ alkylcarbonyl group, a $C_6 \sim C_{60}$ arylcarbonyl group and a $C_6 \sim C_{60}$ arylamine group; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $Ar_2$ to $Ar_6$ are each independently unsubstituted or substituted with one or more types of substituents selected from the group consisting of deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_6 \sim C_{60}$ aryl group, a heteroaryl group having 5 to 60 nuclear atoms, a $C_6 \sim C_{60}$ aryloxy group, a $C_1 \sim C_{40}$ alkyloxy group, a $C_6 \sim C_{60}$ arylamine group, a $C_3 \sim C_{40}$ cycloalkyl group, a heterocycloalkyl group having 3 to 40 nuclear atoms, a $C_1 \sim C_{40}$ alkylsilyl group, a $C_1 \sim C_{40}$ alkylsulfonyl group, a $C_6 \sim C_{60}$ arylsulfonyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group, a $C_1 \sim C_{40}$ alkylcarbonyl group, a $C_6 \sim C_{60}$ arylcarbonyl group and a $C_6 \sim C_{60}$ arylsilyl group, and when substituted with a plurality of the substituents, these are the same as or different from each other.

According to preferred one embodiment of the present invention, the ring represented by Chemical Formula 9 may be represented by the following Chemical Formula 19 or 20:

[Chemical Formula 19]

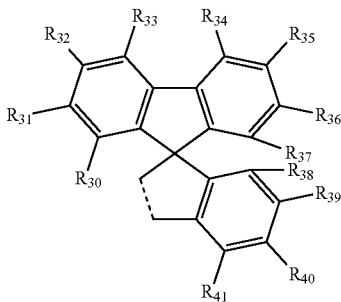

[Chemical Formula 20]

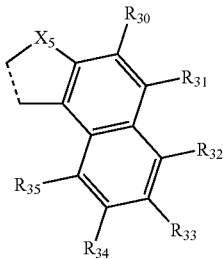

in Chemical Formulae 19 and 20, a dotted line means a part that is fused;

$X_5$ is O, N, a $C(Ar_2)(Ar_3)$, S, $Si(Ar_4)(Ar_5)$ or $P(=O)(Ar_6)$;

$Ar_2$ to $Ar_6$ are each independently selected from the group consisting of hydrogen, deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_3 \sim C_{40}$ cycloalkyl group, a heterocycloalkyl group having 3 to 40 nuclear atoms, a $C_6 \sim C_{60}$ aryl group, a heteroaryl group having 5 to 60 nuclear atoms, a $C_1 \sim C_{40}$ alkyloxy group, a $C_6 \sim C_{60}$ aryloxy group, a $C_3 \sim C_{40}$ alkylsilyl group, a $C_6 \sim C_{60}$ arylsilyl group, a $C_1 \sim C_{40}$ alkylsulfonyl group, a $C_6 \sim C_{60}$ arylsulfonyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group, a $C_1 \sim C_{40}$ alkylcarbonyl group, a $C_6 \sim C_{60}$ arylcarbonyl group and a $C_6 \sim C_{60}$ arylamine group;

the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $Ar_2$ to $Ar_6$ are each independently unsubstituted or substituted with one or more types of substituents selected from the group consisting of deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_6 \sim C_{60}$ aryl group, a heteroaryl group having 5 to 60 nuclear atoms, a $C_6 \sim C_{60}$ aryloxy group, a $C_1 \sim C_{40}$ alkyloxy group, a $C_6 \sim C_{60}$ arylamine group, a $C_3 \sim C_{40}$ cycloalkyl group, a heterocycloalkyl group having 3 to 40 nuclear atoms, a $C_1 \sim C_{40}$ alkylsilyl group, a $C_1 \sim C_{40}$ alkylsulfonyl group, a $C_6 \sim C_{60}$ arylsulfonyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group, a $C_1 \sim C_{40}$ alkylcarbonyl group, a $C_6 \sim C_{60}$ arylcarbonyl group and a $C_6 \sim C_{60}$ arylsilyl group, and when substituted with a plurality of the substituents, these are the same as or different from each other;

$R_{30}$ to $R_{41}$ are each independently a substituent represented by the following Chemical Formula 15;

[Chemical Formula 15]

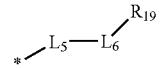

in Chemical Formula 15,

* means a part where a bond is formed;

$L_5$ and $L_6$ are each independently selected from the group consisting of a single bond, a $C_6 \sim C_{18}$ arylene group and a heteroarylene group having 5 to 18 nuclear atoms;

$R_{19}$ is selected from the group consisting of hydrogen, deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_3 \sim C_{40}$ cycloalkyl group, a heterocycloalkyl group having 3 to 40 nuclear atoms, a $C_6 \sim C_{60}$ aryl group, a heteroaryl group having 5 to 60 nuclear atoms, a $C_1 \sim C_{40}$ alkyloxy group, a $C_6 \sim C_{60}$ aryloxy group, a $C_3 \sim C_{40}$ alkylsilyl group, a $C_6 \sim C_{60}$ arylsilyl group, a $C_1 \sim C_{40}$ alkylsulfonyl group, a $C_6 \sim C_{60}$ arylsulfonyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group, a $C_1 \sim C_{40}$ alkylcarbonyl group, a $C_6 \sim C_{60}$ arylcarbonyl group and a $C_6 \sim C_{60}$ arylamine group, or bonds to an adjacent group to form an aromatic ring having 5 to 50 nuclear atoms, a non-aromatic fused polycyclic ring having 5 to 50 nuclear atoms, an aromatic heteroring having 5 to 50 nuclear atoms, or a non-aromatic fused heteropolycyclic ring having 5 to 50 nuclear atoms; and the arylene group and the heteroarylene group of $L_5$ and $L_6$, the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_{19}$, and the aromatic ring, the non-aromatic fused polycyclic ring, the aromatic heteroring and the non-aromatic fused heteropolycyclic ring formed by adjacent two substituents bonding to each other are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$-$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

According to preferred one embodiment of the present invention, the compound represented by Chemical Formula 1 may be represented by the following Chemical Formula 21:

[Chemical Formula 21]

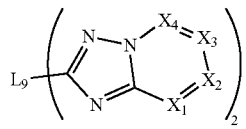

in Chemical Formula 21, $L_9$ is selected from the group consisting of a single bond, a $C_6$~$C_{18}$ arylene group and a heteroarylene group having 5 to 18 nuclear atoms; and $X_1$ to $X_4$ each have the same definition as in Chemical Formula 1, however, each of the two $X_1$s to $X_4$s may be the same as or different from each other.

According to preferred one embodiment of the present invention, $L_1$ to $L_5$ may be each independently selected from the group consisting of a phenylene group, a biphenylene group, a naphthalenyl group, a quinazolinyl group, a carbazolyl group and a fluorenyl group.

According to preferred one embodiment of the present invention, $L_1$ to $L_8$ may be each independently a linker represented by any one of the following Chemical Formulae A-1 to A-6:

A-1

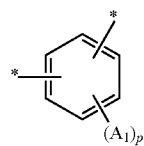

A-2

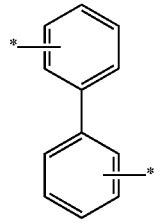

A-3

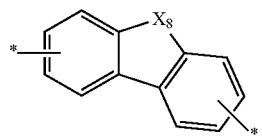

A-4

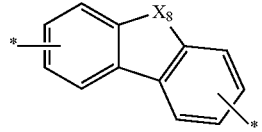

A-5

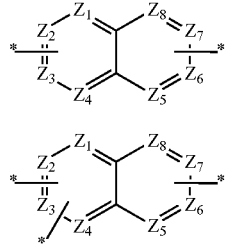

A-6 in Chemical Formulae A-1 to A-6,

* means a part where a bond is formed;

p is an integer of 0 to 4;

$A_1$ is selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, and when $A_1$ is present in plural numbers, these are the same as or different from each other;

$Z_1$ to $Z_8$ are each independently N or $C(Ar_5)$;

any one of $Z_1$ to $Z_4$ and any one of $Z_5$ to $Z_8$ bonding as a linker in Chemical Formula A-3 are $C(Ar_5)$, and herein, $Ar_8$ is not present;

any two of $Z_1$ to $Z_4$ bonding as a linker in Chemical Formula A-4 are $C(Ar_5)$, and herein, $Ar_5$ is not present;

$X_8$s are each independently O, S, $N(Ar_9)$ or $C(Ar_{10})(Ar_1)$;

$X_9$ is N or $C(Ar_{12})$;

$Ar_8$ to $Ar_{12}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1\sim C_{40}$ alkyloxy group, a $C_6\sim C_{60}$ aryloxy group, a $C_3\sim C_{40}$ alkylsilyl group, a $C_6\sim C_{60}$ arylsilyl group, a $C_1\sim C_{40}$ alkylsulfonyl group, a $C_6\sim C_{60}$ arylsulfonyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphinyl group, a $C_1\sim C_{40}$ alkylcarbonyl group, a $C_6\sim C_{60}$ arylcarbonyl group and a $C_6\sim C_{60}$ arylamine group, and when $Ar_8$ is present in plural numbers, these are the same as or different from each other; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $A_1$ and $Ar_8$ to $Ar_{12}$ are each independently unsubstituted or substituted with one or more types of substituents selected from the group consisting of deuterium, halogen, a cyano group, a nitro group, a $C_1\sim C_{40}$ alkyl group, a $C_2\sim C_{40}$ alkenyl group, a $C_2\sim C_{40}$ alkynyl group, a $C_6\sim C_{60}$ aryl group, a heteroaryl group having 5 to 60 nuclear atoms, a $C_6\sim C_{60}$ aryloxy group, a $C_1\sim C_{40}$ alkyloxy group, a $C_6\sim C_{60}$ arylamine group, a $C_3\sim C_{40}$ cycloalkyl group, a heterocycloalkyl group having 3 to 40 nuclear atoms, a $C_1\sim C_{40}$ alkylsilyl group, a $C_1\sim C_{40}$ alkylsulfonyl group, a $C_6\sim C_{60}$ arylsulfonyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphinyl group, a $C_1\sim C_{40}$ alkylcarbonyl group, a $C_6\sim C_{60}$ arylcarbonyl group and a $C_6\sim C_{60}$ arylsilyl group, and when substituted with a plurality of the substituents, these are the same as or different from each other.

According to preferred one embodiment of the present invention, any one of $R_1$, $R_3$, $R_{14}$, $R_{19}$ and $R_{24}$ is selected from the group consisting of a $C_2\sim C_{40}$ alkenyl group, a $C_6\sim C_{60}$ aryl group, a heteroaryl group having 5 to 60 nuclear atoms, a $C_3\sim C_{40}$ alkylsilyl group, a $C_6\sim C_{60}$ arylsilyl group, a $C_1\sim C_{40}$ alkylsulfonyl group, a $C_6\sim C_{60}$ arylsulfonyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphinyl group, a $C_1\sim C_{40}$ alkylcarbonyl group, a $C_6\sim C_{60}$ arylcarbonyl group and a $C_6\sim C_{60}$ arylamine group, and the alkenyl group, the aryl group, the heteroaryl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_1$, $R_3$, $R_{14}$, $R_{19}$ and $R_{24}$ are each independently unsubstituted or substituted with one or more types of substituents selected from the group consisting of halogen, a cyano group, a $C_1\sim C_{40}$ alkyl group, a $C_2\sim C_{40}$ alkenyl group, a $C_2\sim C_{40}$ alkynyl group, a $C_6\sim C_{60}$ aryl group and a heteroaryl group having 5 to 60 nuclear atoms, and when substituted with a plurality of the substituents, these are the same as or different from each other.

According to preferred one embodiment of the present invention, at least one of $R_1$ and $R_3$ is each independently selected from the group consisting of a $C_2\sim C_{40}$ alkenyl group, a $C_6\sim C_{60}$ aryl group, a heteroaryl group having 5 to 60 nuclear atoms, a $C_3\sim C_{40}$ alkylsilyl group, a $C_6\sim C_{60}$ arylsilyl group, a $C_1\sim C_{40}$ alkylsulfonyl group, a $C_6\sim C_{60}$ arylsulfonyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphinyl group, a $C_1\sim C_{40}$ alkylcarbonyl group, a $C_6\sim C_{60}$ arylcarbonyl group and a $C_6\sim C_{60}$ arylamine group, and the alkenyl group, the aryl group, the heteroaryl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_1$ and $R_3$ are each independently unsubstituted or substituted with one or more types of substituents selected from the group consisting of halogen, a cyano group, a $C_1\sim C_{40}$ alkyl group, a $C_2\sim C_{40}$ alkenyl group, a $C_2\sim C_{40}$ alkynyl group, a $C_6\sim C_{60}$ aryl group and a heteroaryl group having 5 to 60 nuclear atoms, and when substituted with a plurality of the substituents, these are the same as or different from each other.

According to preferred one embodiment of the present invention, $R_{14}$ is selected from the group consisting of a $C_2\sim C_{40}$ alkenyl group, a $C_6\sim C_{60}$ aryl group, a heteroaryl group having 5 to 60 nuclear atoms, a $C_3\sim C_{40}$ alkylsilyl group, a $C_6\sim C_{60}$ arylsilyl group, a $C_1\sim C_{40}$ alkylsulfonyl group, a $C_6\sim C_{60}$ arylsulfonyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphinyl group, a $C_1\sim C_{40}$ alkylcarbonyl group, a $C_6\sim C_{60}$ arylcarbonyl group and a $C_6\sim C_{60}$ arylamine group, and the alkenyl group, the aryl group, the heteroaryl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_{14}$ are each independently unsubstituted or substituted with one or more types of substituents selected from the group consisting of halogen, a cyano group, a $C_1\sim C_{40}$ alkyl group, a $C_2\sim C_{40}$ alkenyl group, a $C_2\sim C_{40}$ alkynyl group, a $C_6\sim C_{60}$ aryl group and a heteroaryl group having 5 to 60 nuclear atoms, and when substituted with a plurality of the substituents, these are the same as or different from each other.

According to preferred one embodiment of the present invention, $R_{19}$ is selected from the group consisting of a $C_2\sim C_{40}$ alkenyl group, a $C_6\sim C_{60}$ aryl group, a heteroaryl group having 5 to 60 nuclear atoms, a $C_3\sim C_{40}$ alkylsilyl group, a $C_6\sim C_{60}$ arylsilyl group, a $C_1\sim C_{40}$ alkylsulfonyl group, a $C_6\sim C_{60}$ arylsulfonyl group, a $C_6\sim C_{40}$ alkylboron group, a $C_6\sim C_{60}$ arylboron group, a $C_6\sim C_{60}$ arylphosphanyl group, a $C_6\sim C_{60}$ mono or diarylphosphinyl group, a $C_1\sim C_{40}$ alkylcarbonyl group, a $C_6\sim C_{60}$ arylcarbonyl group and a $C_6\sim C_{60}$ arylamine group, and the alkenyl group, the aryl group, the heteroaryl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_{19}$ are each independently unsubstituted or substituted with one or more types of substituents selected from the group consisting of halogen, a cyano group, a $C_1\sim C_{40}$ alkyl group, a $C_2\sim C_{40}$ alkenyl group, a $C_2\sim C_{40}$ alkynyl group, a $C_6\sim C_{60}$ aryl group and a heteroaryl group having 5 to 60 nuclear atoms, and when substituted with a plurality of the substituents, these are the same as or different from each other.

According to preferred one embodiment of the present invention, $R_{24}$ is selected from the group consisting of a $C_2\sim C_{40}$ alkenyl group, a $C_6\sim C_{60}$ aryl group, a heteroaryl group having 5 to 60 nuclear atoms, a $C_3\sim C_{40}$ alkylsilyl group, a $C_6\sim C_{60}$ arylsilyl group, a $C_1\sim C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, and the alkenyl group, the aryl group, the heteroaryl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_{24}$ are each independently unsubstituted or substituted with one or more types of substituents selected from the group consisting of halogen, a cyano group, a $C_1$~$C_{40}$ alkyl group, a $C_2$~$C_{40}$ alkenyl group, a $C_2$~$C_{40}$ alkynyl group, a $C_6$~$C_{60}$ aryl group and a heteroaryl group having 5 to 60 nuclear atoms, and when substituted with a plurality of the substituents, these are the same as or different from each other.

According to preferred one embodiment of the present invention, at least one of $R_1$, $R_3$, $R_{14}$, $R_{19}$ and $R_{24}$ is each independently a substituent represented by any one of the following Chemical Formulae B-1 to B-7:

B-1

B-2

B-3

B-4

B-5

B-6

B-7 in Chemical Formulae B-1 to B-7,

* means a part where a bond is formed;

$Z_9$ to $Z_{13}$ are each independently N or $C(Ar_{13})$;

any one of $Z_9$ to $Z_{12}$ forming a bond as a substituent in Chemical Formula B-4 is $C(Ar_{13})$, and herein, $Ar_3$ is present;

$T_1$ and $T_2$ are each independently selected from the group consisting of a single bond, a $C(Ar_{14})(Ar_{15})$, $N(Ar_{16})$, O, S, $S(=O)(=O)$, $B(Ar_{17})$ and $Si(Ar_{18})(Ar_{19})$, however, $T_1$ and $T_2$ are not both a single bond;

$T_3$ is $N(Ar_{20})$ or O;

q and r are each independently an integer of 0 to 4;

$A_2$ and $A_3$ are each independently selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, and when $A_2$ and $A_3$ are each present in plural numbers, these are the same as or different from each other;

$B_1$ and $Ar_{13}$ to $Ar_{20}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, and when $Ar_{13}$ to $Ar_{19}$ are each present in plural numbers, these are the same as or different from each other; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $A_2$, $A_3$, $B_1$ and $Ar_{13}$ to $Ar_{20}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

The compound represented by Chemical Formula 1 of the present invention may be represented by the following compounds, but is not limited thereto:

J-1

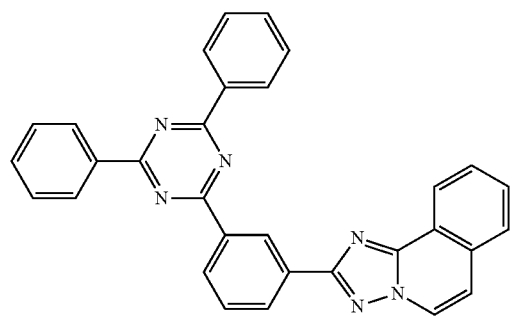

J-2

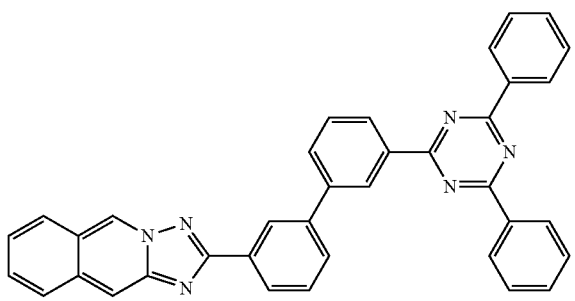

J-3

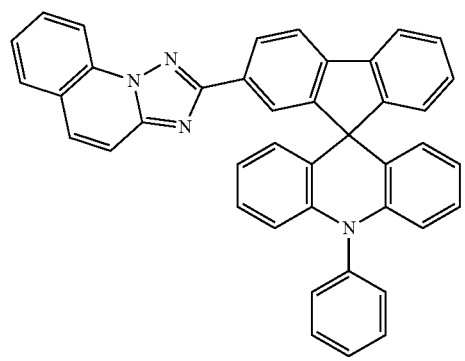

J-4

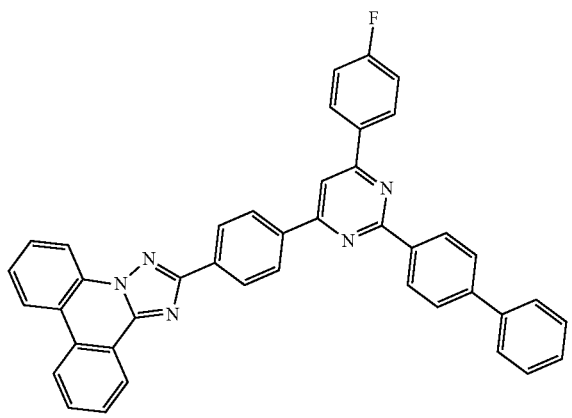

J-5

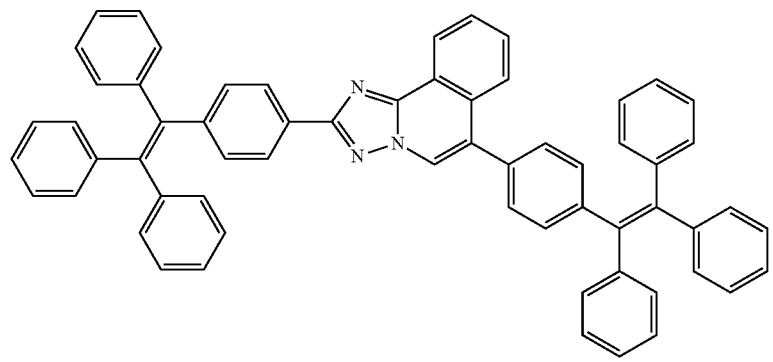

-continued
J-6 J-7
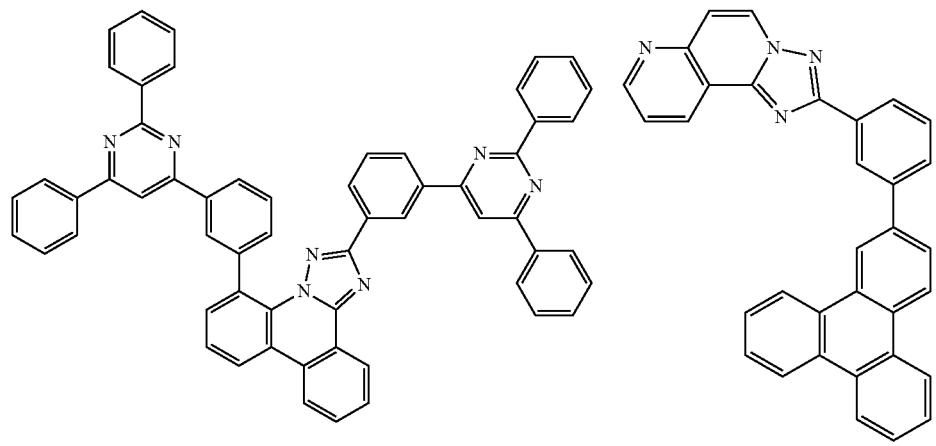
J-8 J-9
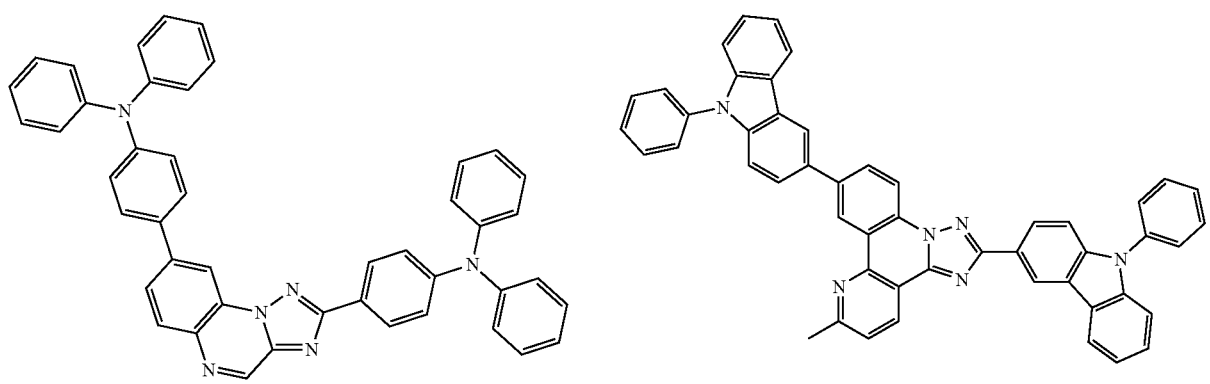
J-10 J-11
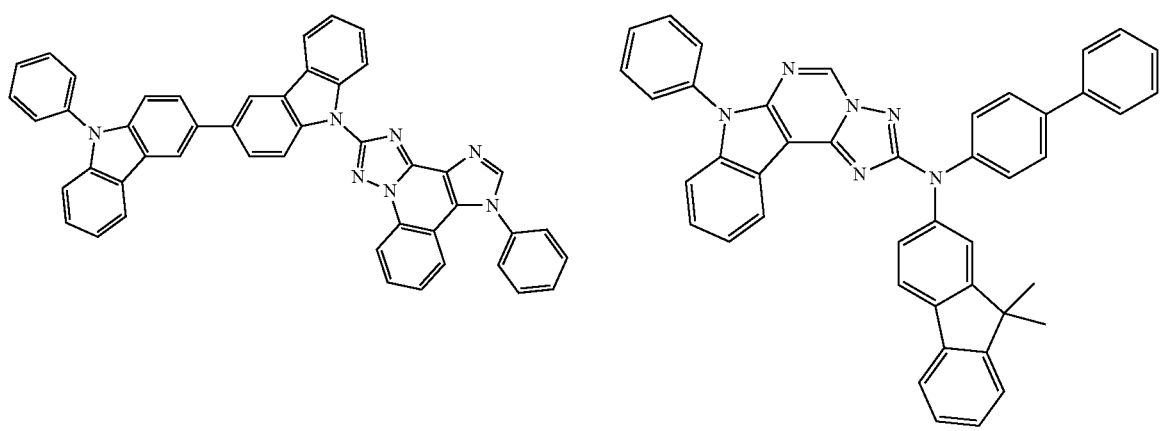

-continued
J-12
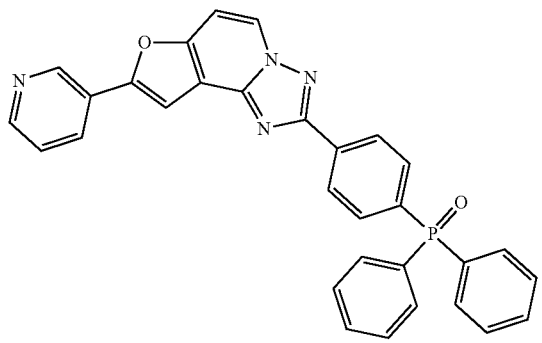
J-13
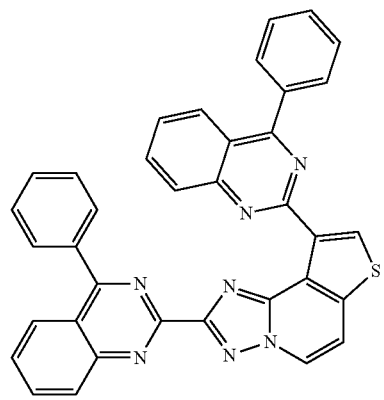
J-14
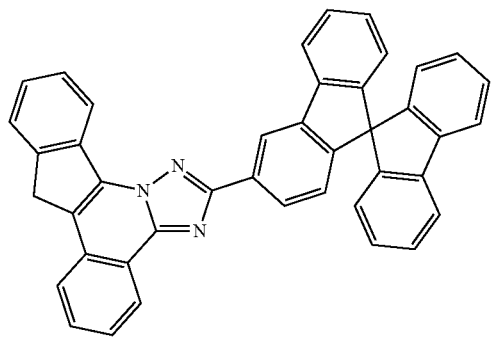
J-15
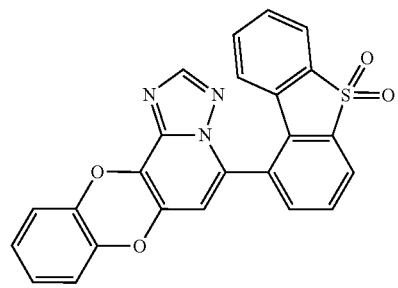
J-16
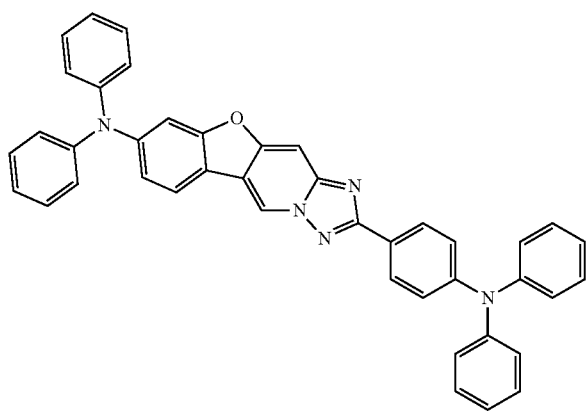
J-17
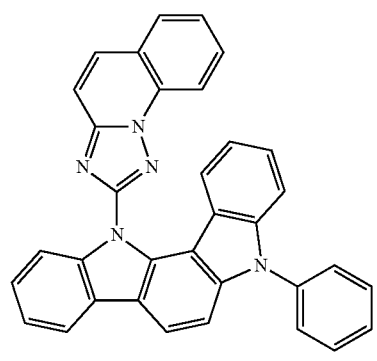

-continued
J-18
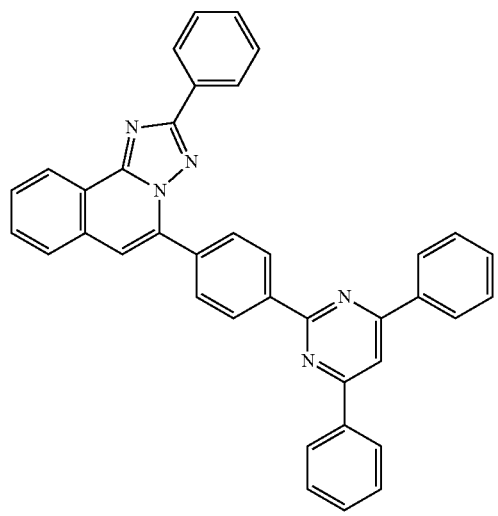
J-19
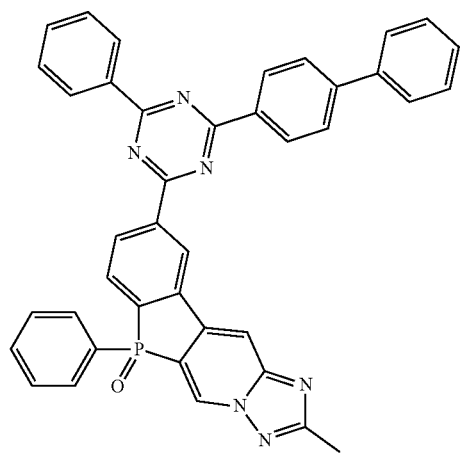
J-20
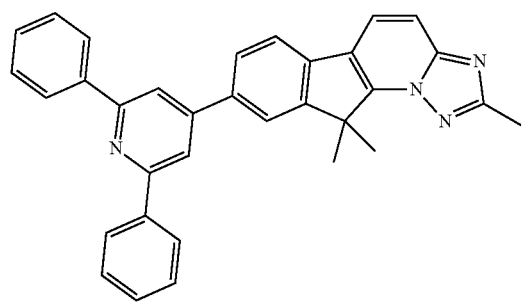
J-21
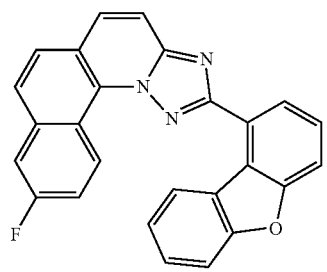
J-22
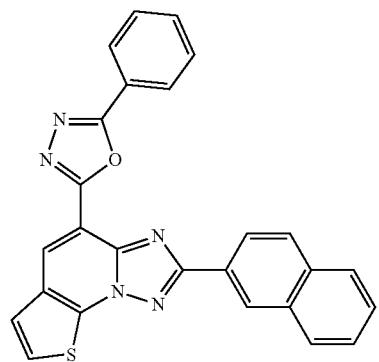
J-23
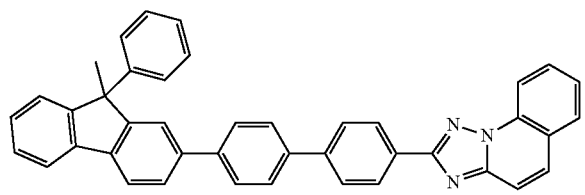
J-24
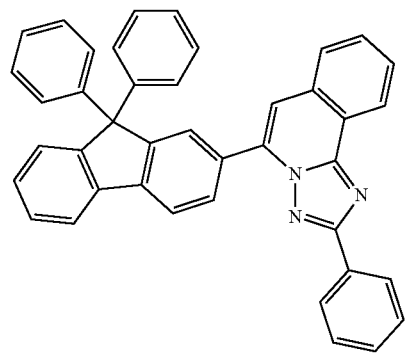
J-25
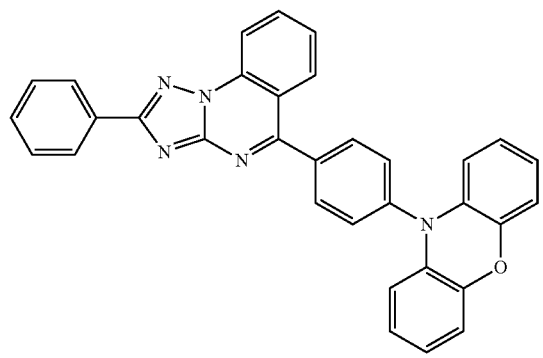

-continued
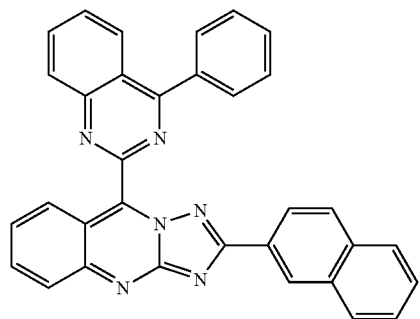
J-26
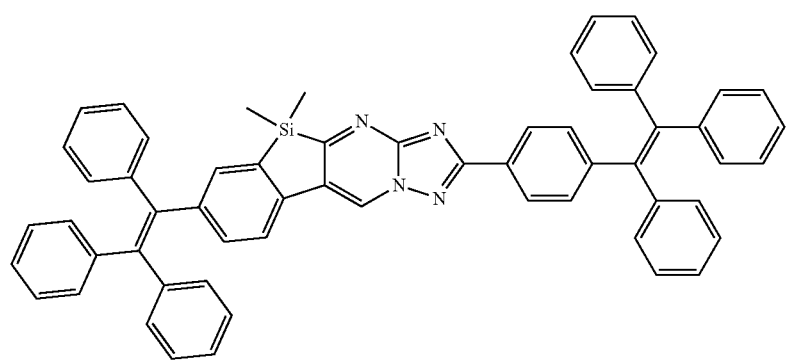
J-27
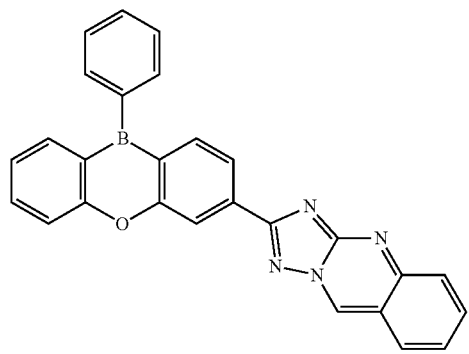
J-28
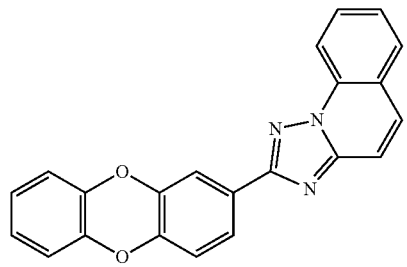
J-30
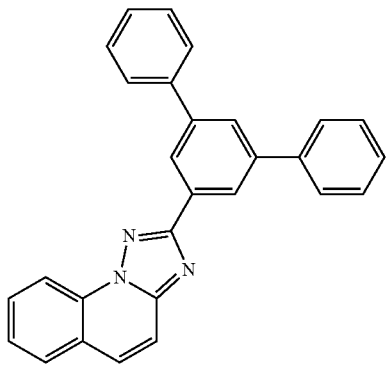
J-31

-continued
J-32
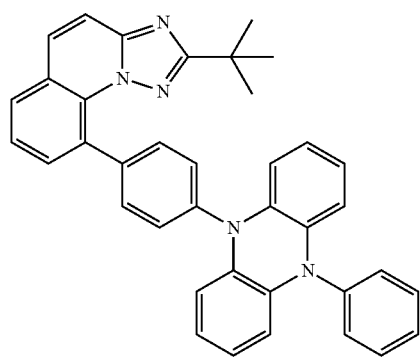
J-33
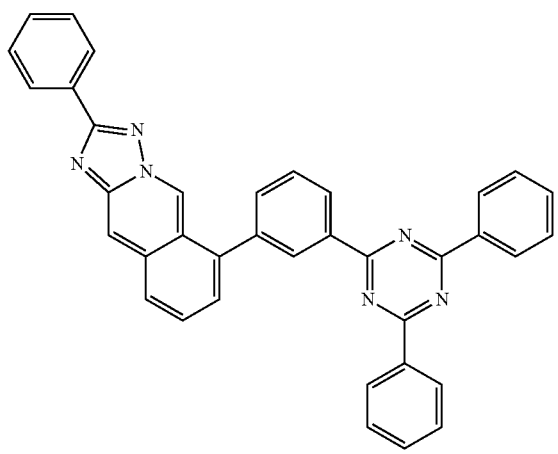
J-34
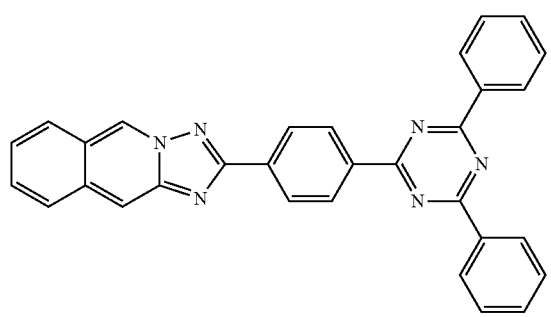
J-35
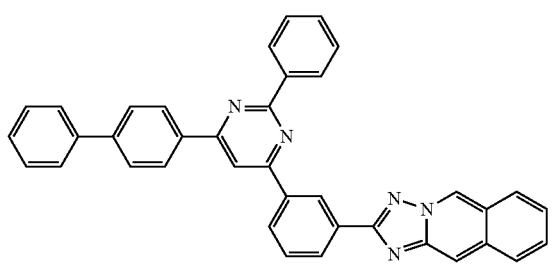
J-36
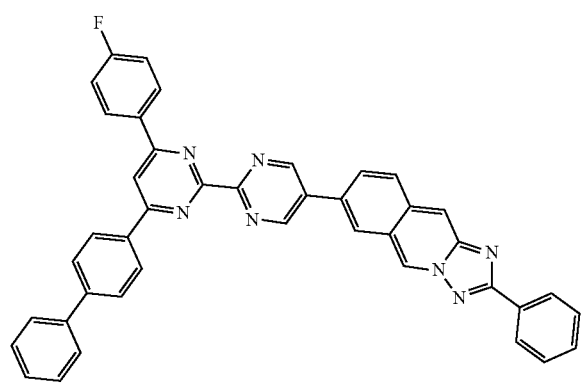
J-37
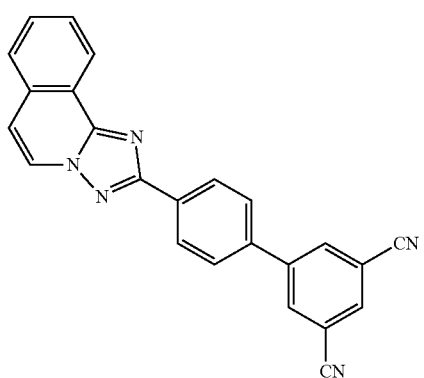
J-38
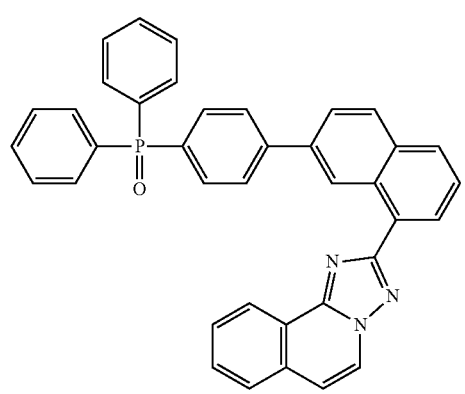
J-39
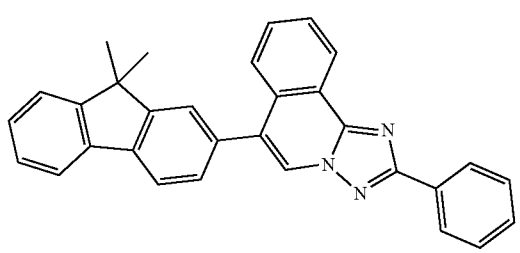

-continued
J-40
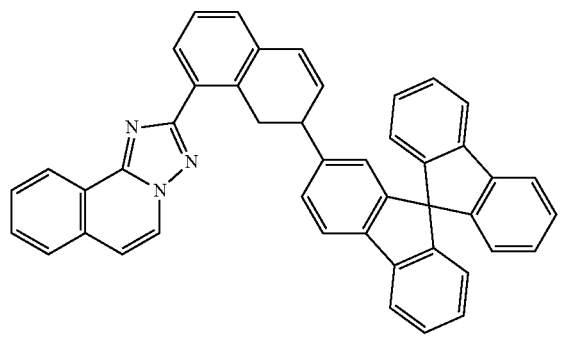
J-41
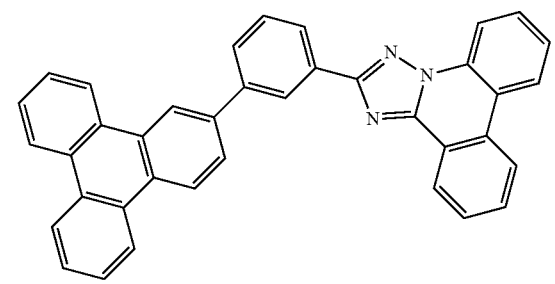
J-42
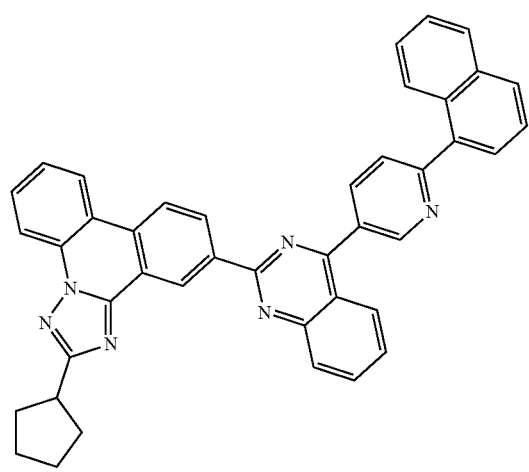
J-43
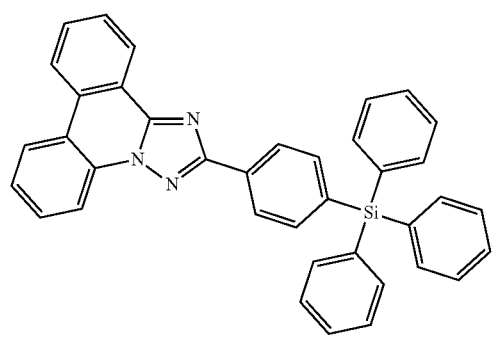
J-44
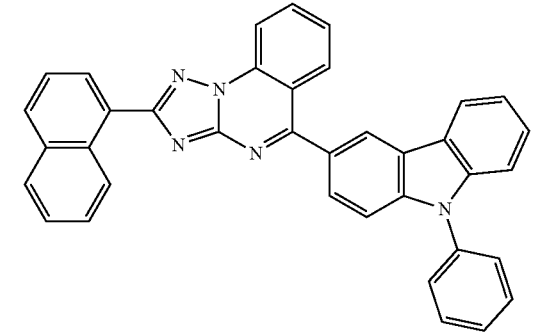
J-45
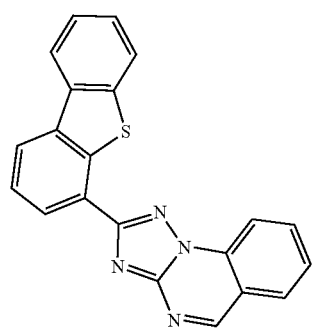
J-46
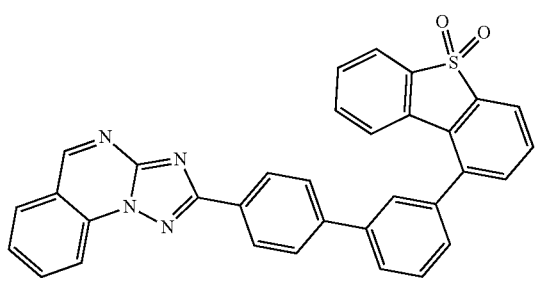
J-47

-continued
J-48
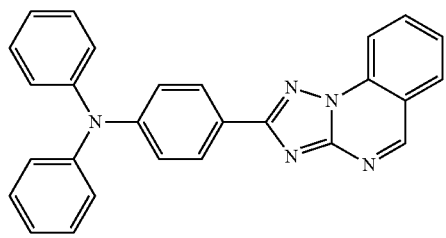
J-49
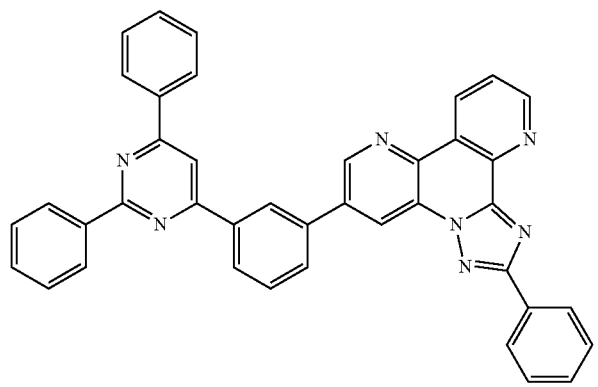
J-50
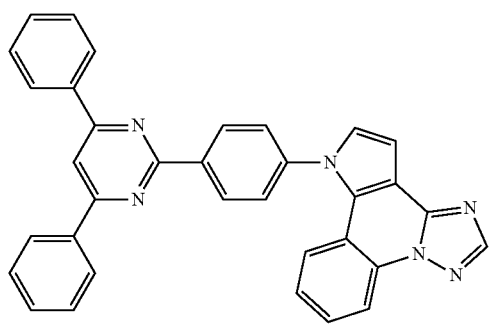
J-51
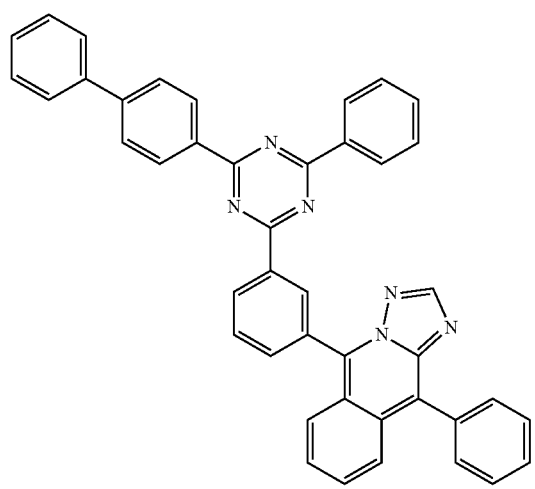
J-52
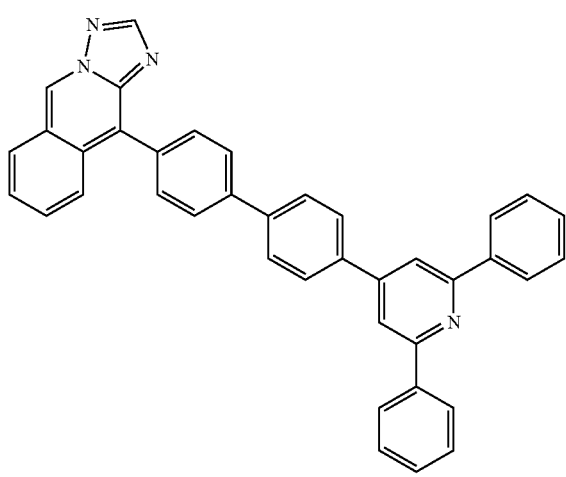
J-53
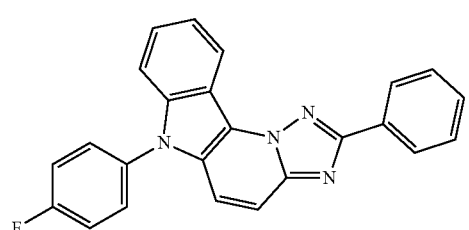

-continued
J-54
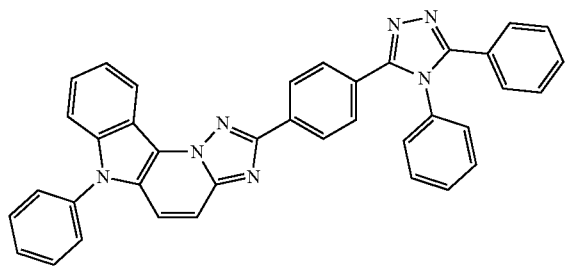
J-55
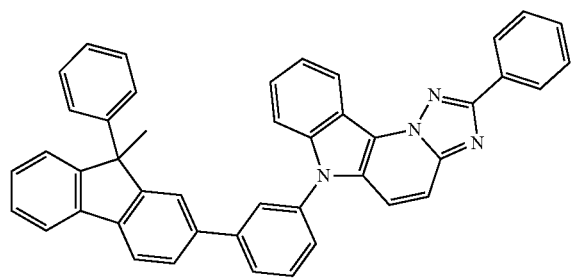
J-56
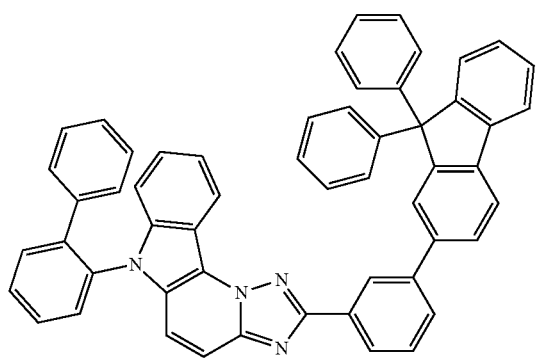
J-57
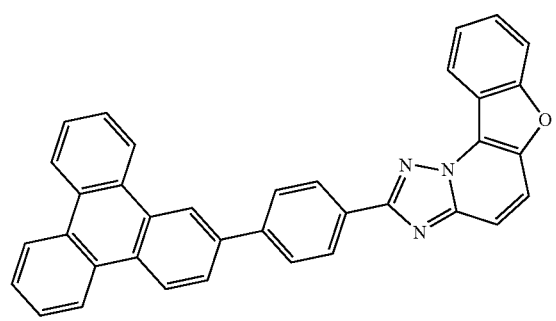
J-58
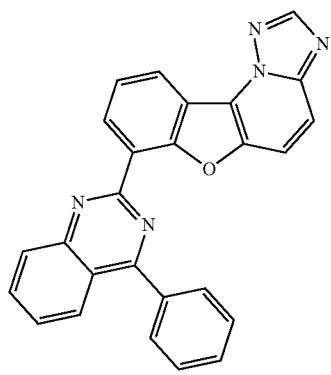
J-59
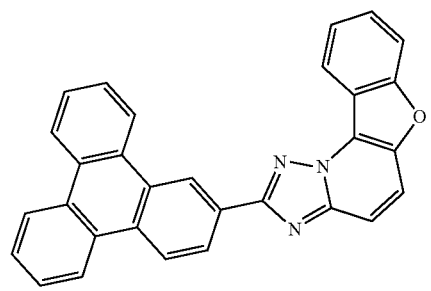
J-60
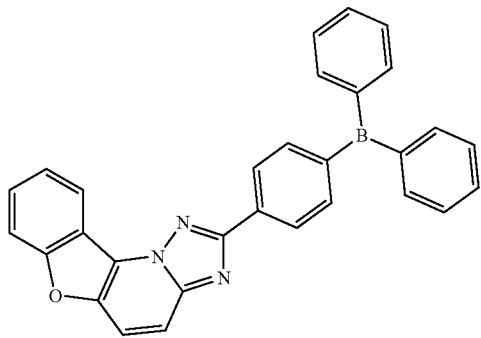
J-61
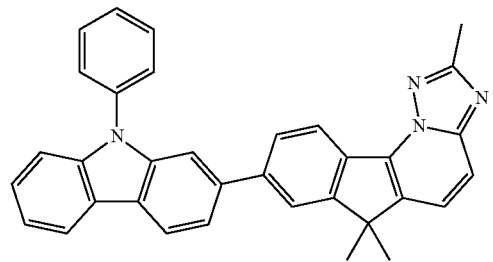

-continued
J-62
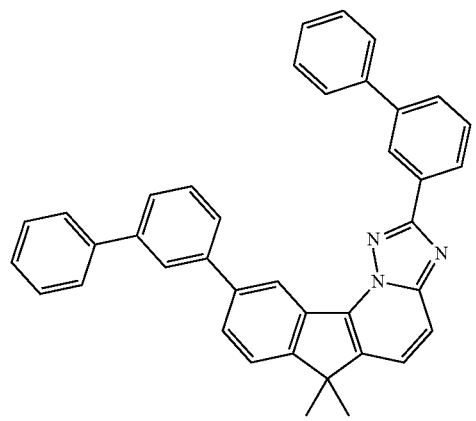
J-63
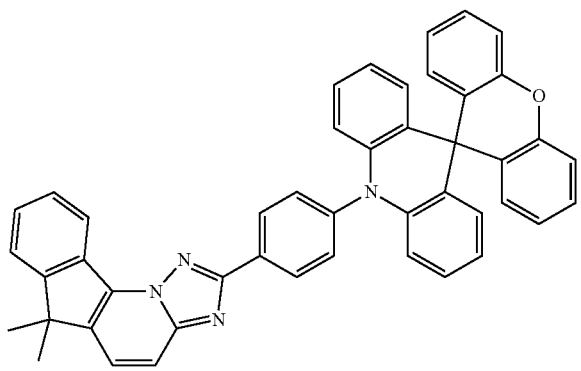
J-64
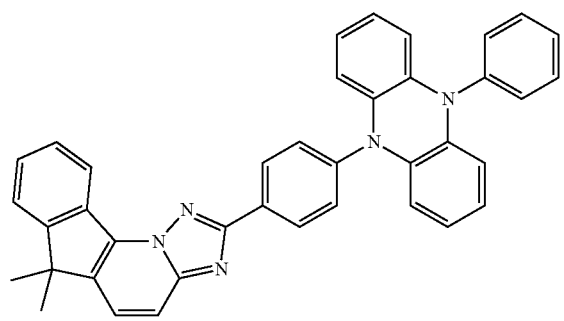
J-65
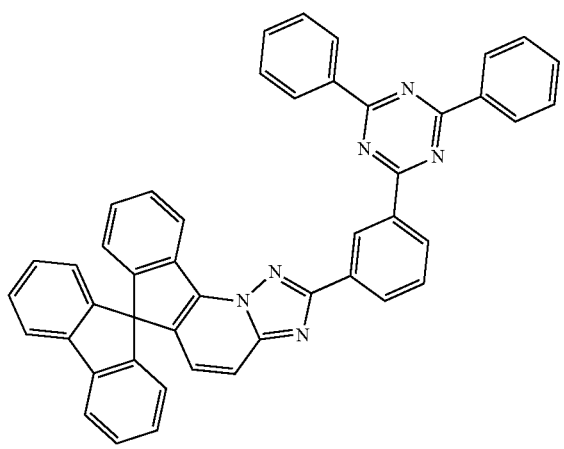
J-66
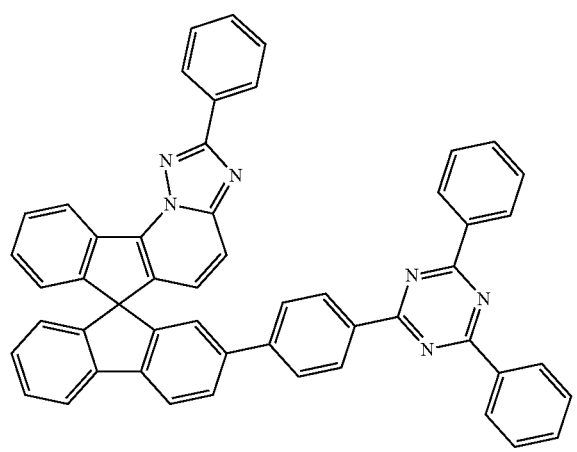
J-67
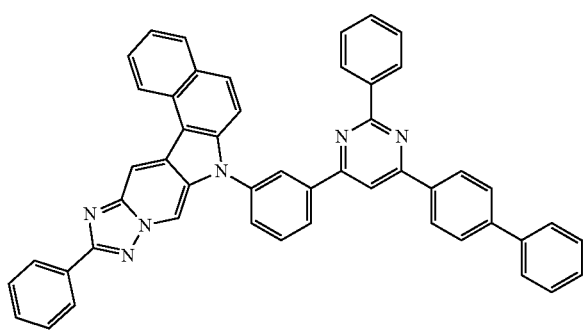

-continued
J-68
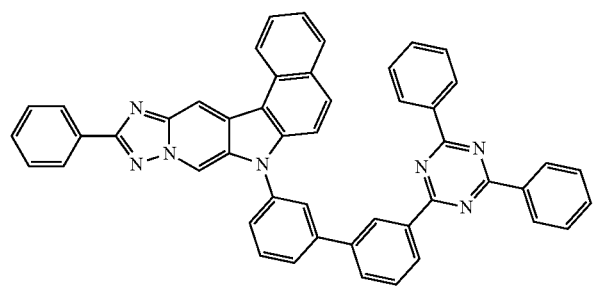
J-69
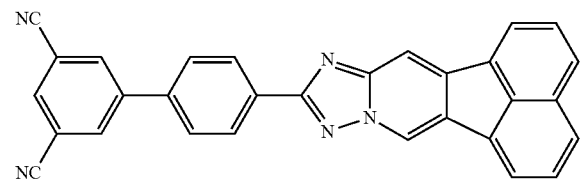
J-70
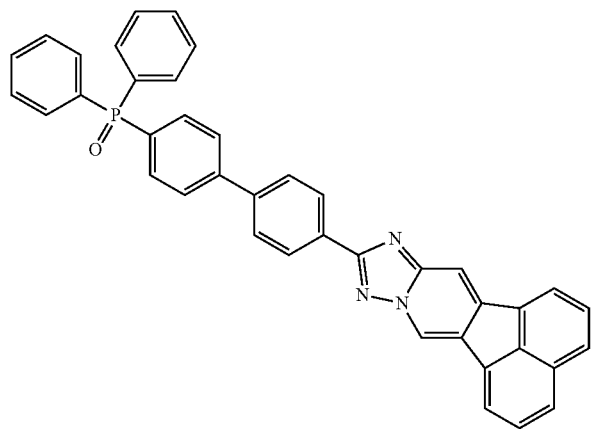
J-71
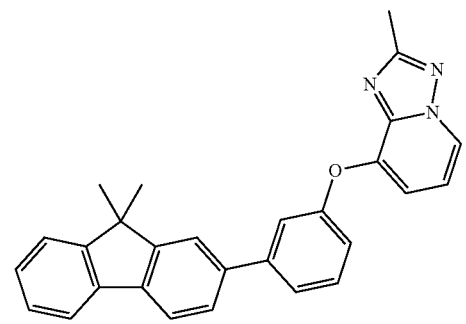
J-72
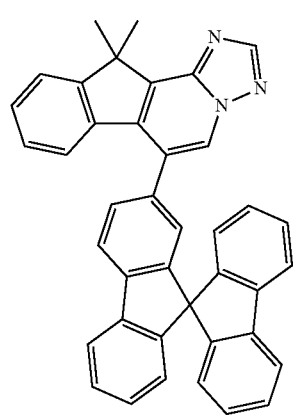
J-73
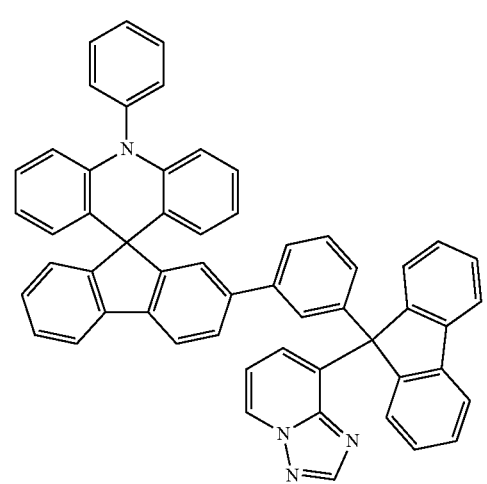

-continued
J-74
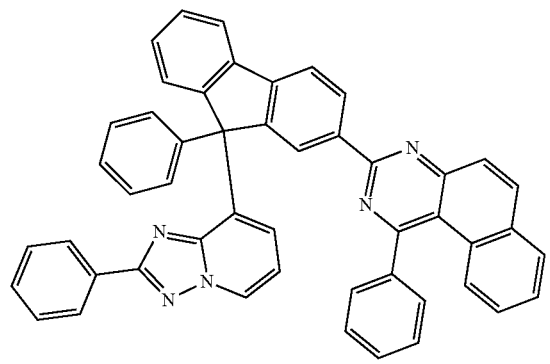
J-75
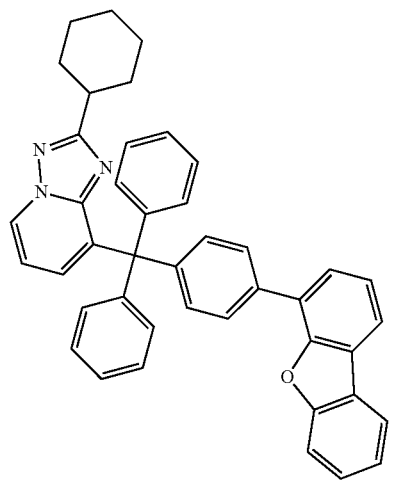
J-76
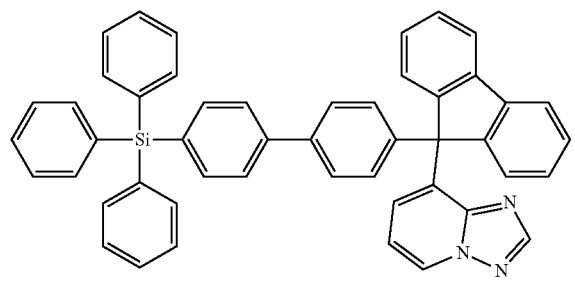
J-77
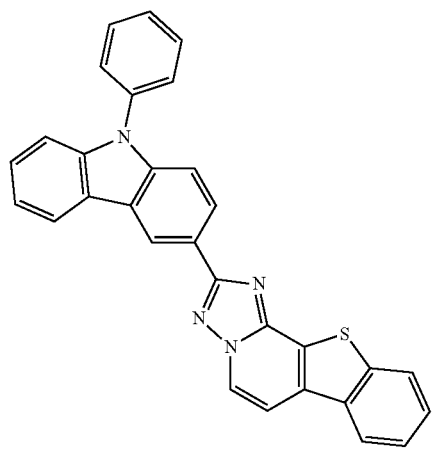
J-78
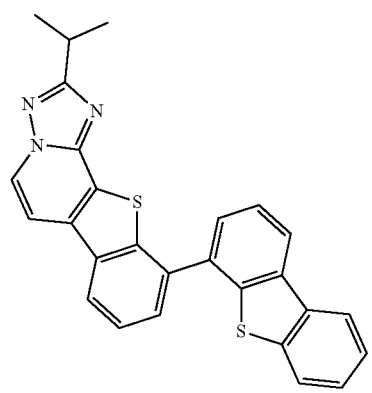
J-79
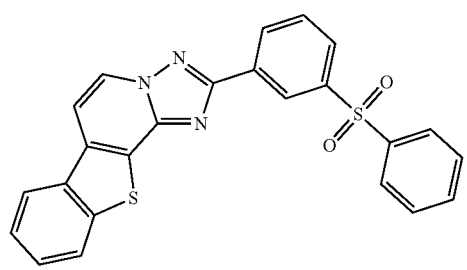
J-80
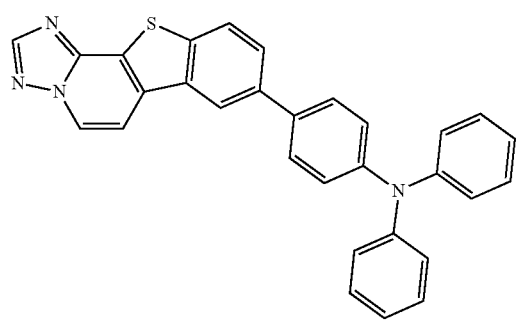
J-81
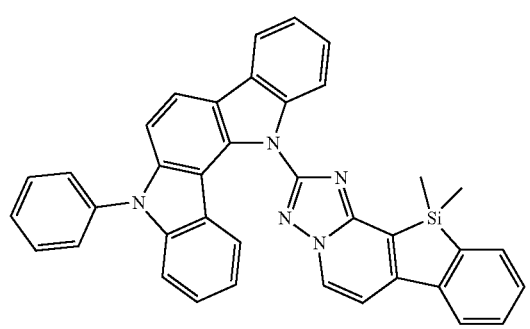

-continued
J-82
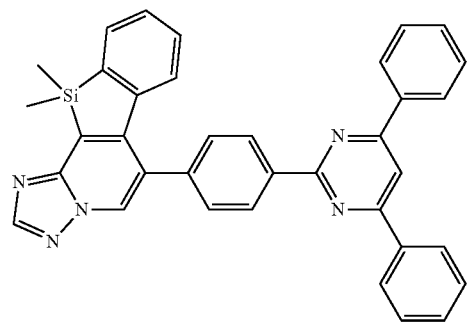
J-83
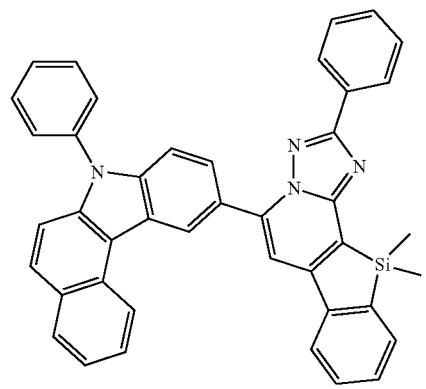
J-84
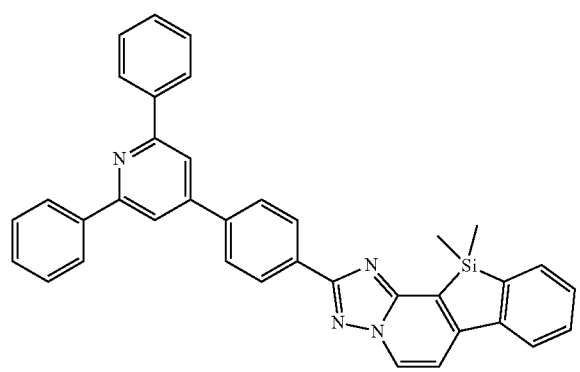
J-85
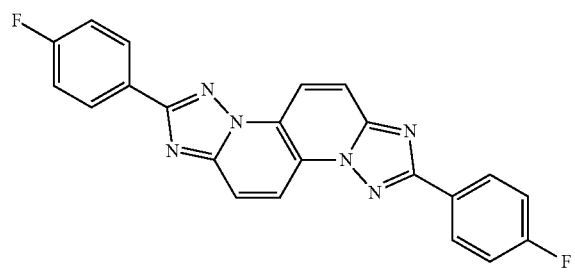
J-86
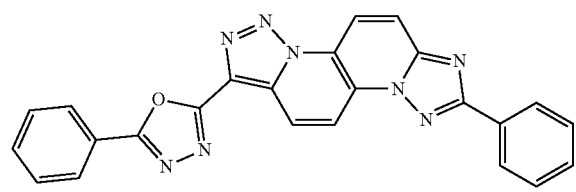
J-87
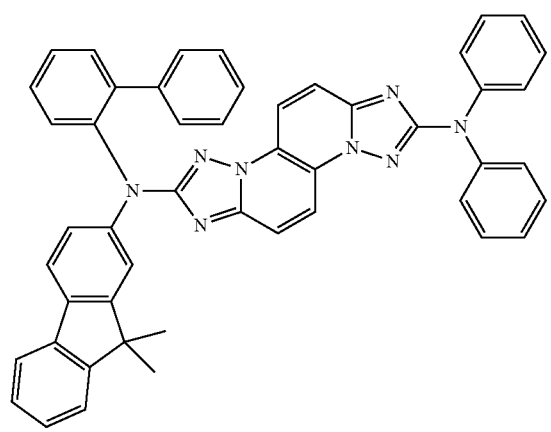

-continued
J-88
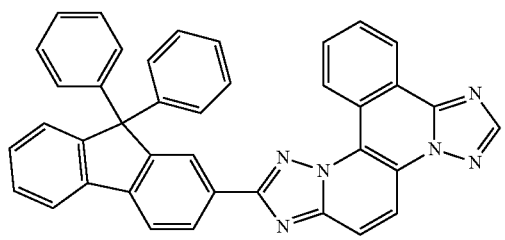
J-89
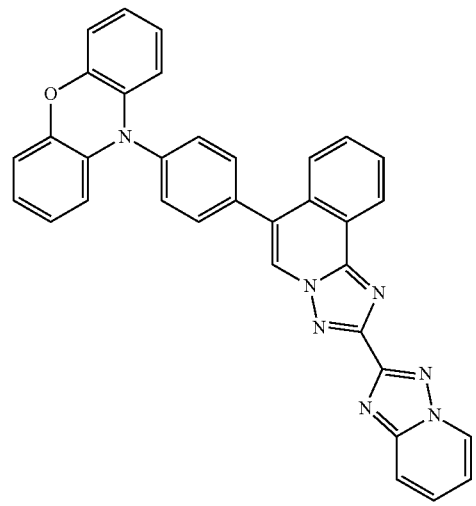
J-90
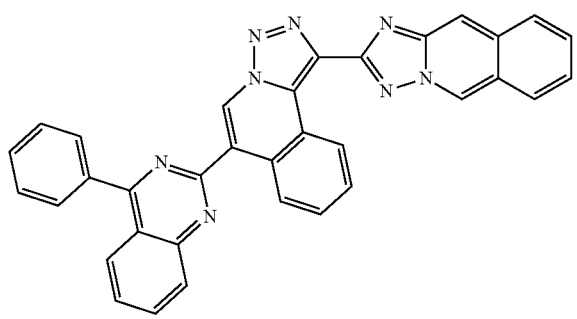
J-91
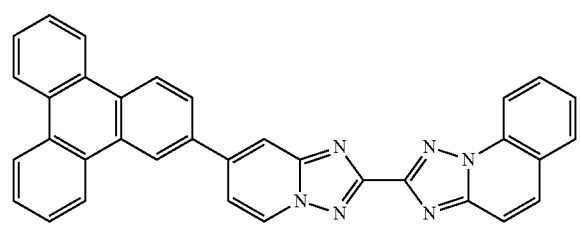
J-92
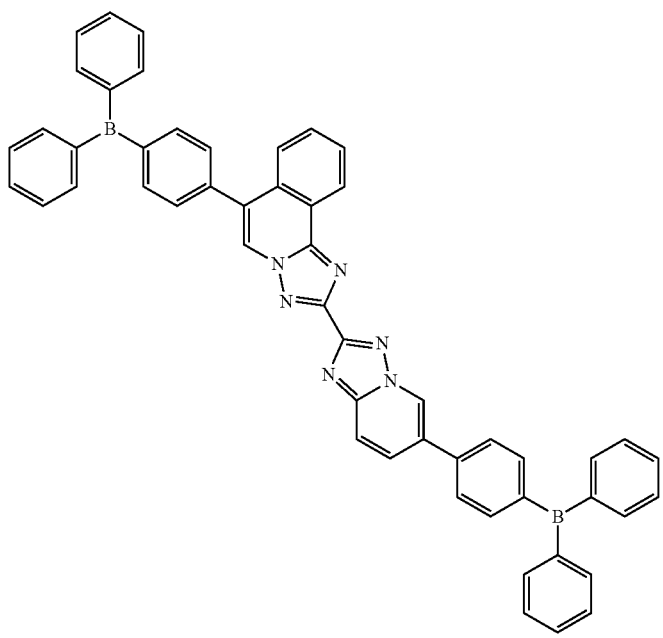

-continued

J-93

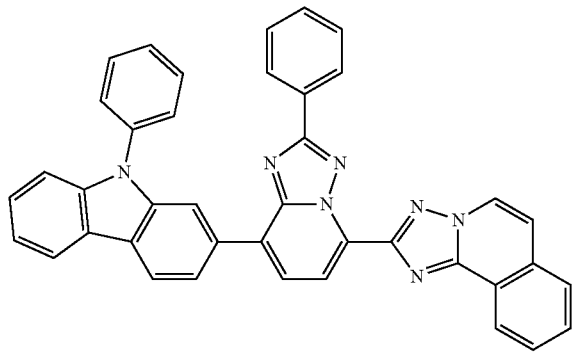

J-94

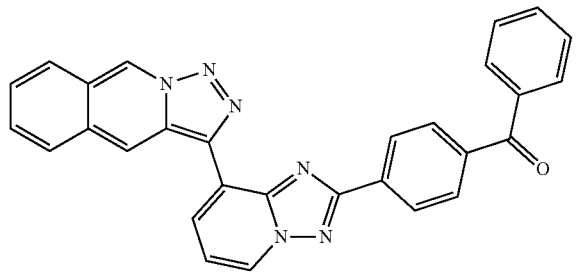

J-95

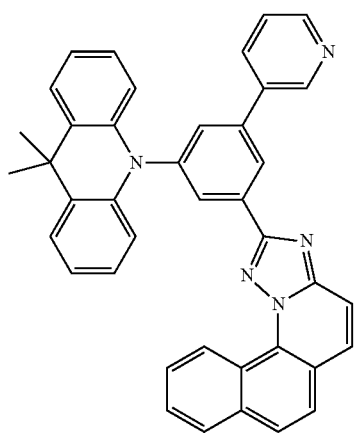

J-96

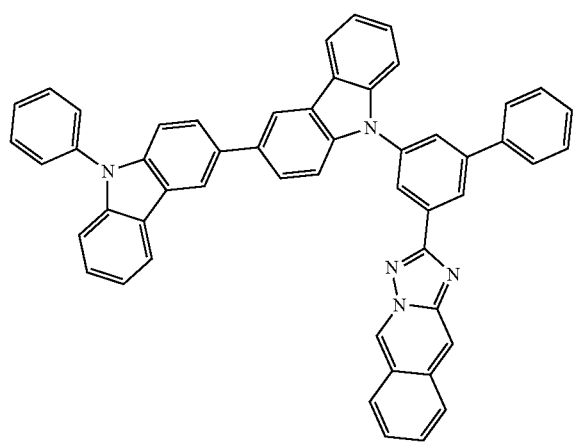

The compound of Chemical Formula 1 of the present invention may be synthesized using general synthesis methods (refer to Chem. Rev., 60:313 (1960); J Chem. SOC. 4482 (1955); Chem. Rev. 95: 2457 (1995) or the like). Detailed synthesis processes of the compounds of the present invention will be specifically described in synthesis examples to be described later.

2. Organic Electroluminescent Device

Meanwhile, another aspect of the present invention relates to an organic electroluminescent device (organic EL device) including the compound represented by Chemical Formula 1 according to the present invention.

Specifically, the present invention relates to an organic electroluminescent device including an anode, a cathode, and one or more organic material layers provided between the anode and the cathode, and at least one of the one or more organic material layers includes the compound represented by Chemical Formula 1. Herein, the compound may be used either alone or as a mixture of two or more.

The one or more organic material layers may be any one or more of a hole injection layer, a hole transport layer, a light emitting layer, a light emitting auxiliary layer, a lifespan improving layer, an electron transport layer, a hole blocking layer and an electron injection layer, and at least one organic material layer among these may include the compound represented by Chemical Formula 1.

The structure of the organic electroluminescent device according to the present invention described above is not particularly limited, but, when referring to FIG. 1 as one example, includes an anode (10) and a cathode (20) facing each other, and an organic layer (30) located between the anode (10) and the cathode (20). Herein, the organic layer (30) may include a hole transport layer (31), a light emitting layer (32) and an electron transport layer (34). In addition, an electron blocking layer (33) may be included between the hole transport layer (31) and the light emitting layer (32), and a hole blocking layer (35) may be included between the electron transport layer (34) and the light emitting layer (32).

When referring to FIG. 2 as another example of the present invention, the organic layer (30) may further include a hole injection layer (37) between the hole transport layer (31) and the anode (10), and may further include an electron injection layer (36) between the electron transport layer (34) and the cathode (20).

The hole injection layer (37) laminated between the hole transport layer (31) and the anode (10) in the present invention is a layer having a function of, as well as improving interfacial properties between ITO used as the anode and an organic material used as the hole transport layer (31), smoothing the ITO surface by being coated on the top of the ITO of which surface is not smooth, and those commonly used in the art may be used without particular limit, and for example, amine compounds may be used. However, the hole injection layer is not limited thereto.

In addition, the electron injection layer (36) is a layer laminated on the top of the electron transport layer and having a function of facilitating electron injection from the cathode and eventually improving power efficiency, and is not particularly limited as long as it is commonly used in the art. For example, materials such as LiF, Liq, NaCl, CsF, $Li_2O$ or BaO may be used.

Although not shown in the drawings in the present invention, a light emitting auxiliary layer may be further included between the electron blocking layer (33) and the light emitting layer (32). The light emitting auxiliary layer may perform a role of adjusting a thickness of the organic layer (30) while performing a role of transporting holes to the light emitting layer (32). The light emitting auxiliary layer may include a hole transport material, and may be formed with the same material as the hole transport layer (31).

In addition, although not shown in the drawings in the present invention, a lifespan improving layer may be further included between the hole blocking layer (35) and the light emitting layer (32). Holes migrating to the light emitting layer (32) by getting on an ionization potential level in an organic light emitting device are not able to diffuse or migrate to the electron transport layer by being blocked by a high energy barrier of the lifespan improving layer, and consequently, the lifespan improving layer has a function of limiting the holes in the light emitting layer. Such a function of limiting the holes in the light emitting layer prevents the holes from diffusing to the electron transport layer migrating electrons by reduction, and therefore, suppresses a lifespan decrease phenomenon caused through an irreversible decomposition reaction by oxidation, and thereby contributes to improving a lifespan of the organic light emitting device.

In the present invention, the compound represented by Chemical Formula 1 has excellent electron withdrawing group (EWG) properties, is more electrochemically stable compared to a 6-membered heteroring structure known in the art and has excellent electron mobility, and in addition thereto, has a high glass transition temperature and excellent thermal stability. Accordingly, the compound represented by Chemical Formula 1 of the present invention has excellent electron transport ability and light emission property, and may be used as a material of any one of a hole injection layer, a hole transport layer, a light emitting layer, an electron transport layer and an electron injection layer, an organic material layer of an organic electroluminescent device. The compound represented by Chemical Formula 1 of the present invention may be preferably used as a material of any of a light emitting layer, an electron transport layer and a hole blocking layer further laminated on the electron transport layer, and more preferably used as a material of an electron transport layer, or a hole blocking layer.

In addition, when using the compound according to the present invention as a light emitting layer material, the compound represented by Chemical Formula 1 may be specifically used as a phosphorescent host, a fluorescent host or a dopant material of the light emitting layer, and may be preferably used as a phosphorescent host (blue, green and/or red phosphorescent host material).

In addition, the organic electroluminescent device in the present invention has, as described above, an anode, one or more organic material layers and a cathode consecutively laminated, and in addition thereto, may further include an insulating layer or an adhesive layer at an interface between the electrode and the organic material layer.

Except that at least one or more of the organic material layers (for example, hole blocking layer) are formed to include the compound represented by Chemical Formula 1, the organic electroluminescent device of the present invention may be manufactured by forming other organic material layers and electrodes using materials and methods known in the art.

The organic material layer may be formed using a vacuum deposition method or a solution coating method. Examples of the solution coating method may include spin coating, dip coating, doctor blading, inkjet printing, thermal transfer method or the like, but are not limited thereto.

A substrate capable of being used in the present invention is not particularly limited, and silicon wafers, quartz, glass plates, metal plates, plastic films, sheets and the like may be used.

The anode material may be prepared using, for example, a conductor having high work function so as to have smooth hole injection, and examples thereof may include metals such as vanadium, chromium, copper, zinc or gold, or alloys thereof; metal oxides such as zinc oxide, indium oxide, indium tin oxide (ITO) or indium zinc oxide (IZO); combinations of metals and oxides such as $ZnO:Al$ or $SnO_2:Sb$; conductive polymers such as polythiophene, poly(3-methylthiophene), poly[3,4-(ethylene-1,2-dioxy)thiophene] (PEDT), polypyrrole or polyaniline; carbon black, and the like, but are not limited thereto.

The cathode material may be prepared using, for example, a conductor having low work function so as to have smooth electron injection, and examples thereof may include metals such as magnesium, calcium, sodium, potassium, titanium, indium, yttrium, lithium, gadolinium, aluminum, silver, tin or lead, or alloys thereof; and multilayer-structured materials such as LiF/Al or $LiO_2/Al$, but are not limited thereto.

Hereinafter, the present invention will be described in detail with reference to examples as follows. However, the following examples are for illustrative purposes only, and the present invention is not limited to the following examples.

[Preparation Example 1] Synthesis of A-1

<Step 1> Synthesis of [(1-isoquinolinylamino)thioxomethyl]-, ethyl ester (9CI)

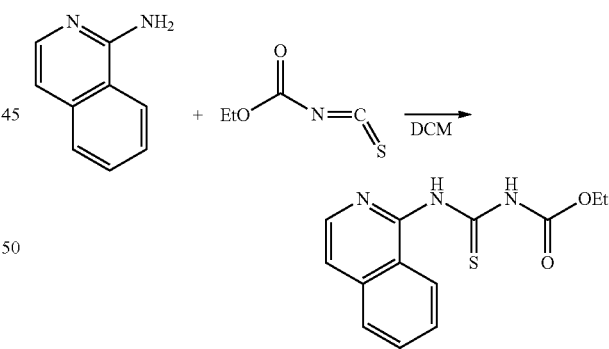

Dichloromethane (10 mL) was added to isoquinoline-1-amine (1.44 g, 10 mmol). The result was cooled to 0° C., and ethoxycarbonyl isothiocyanate (1.31 g, 10 mmol) was slowly added dropwise thereto over 15 minutes. The temperature of the reaction solution was raised to room temperature, and the reaction solution was stirred for 20 hours. The reaction solution was vacuum distilled to properly remove the solvent and then filtered. After drying with warm air, a target compound (2.47 g, yield 90%) was obtained.

$^1$H-NMR: δ 1.26 (t, 3H), 4.18 (q, 2H), 7.08 (d, 1H), 7.43 (t, 1H), 7.60 (m, 2H), 8.30 (m, 2H), 11.46 (s, 1H), 12.41 (s, 1H)

<Step 2> Synthesis of [1,2,4]triazolo[5,1-a]isoquinoline-2-amine

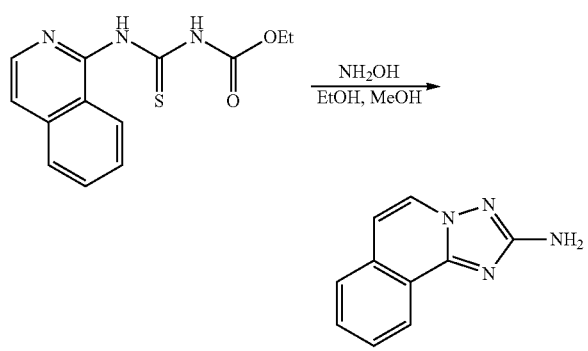

A mixed solvent of EtOH/MeOH (1:1, 20 mL) was added to hydroxylamine hydrochloride (2.77 g, 40 mmol). Triethylamine (3.03 g, 30 mmol) was added to the reaction solution, and the result was stirred for 1 hour. [(1-isoquinolinylamino)thioxomethyl]-, ethyl ester (9CI) (2.75 g, 10 mmol) was added thereto, and after slowly raising the temperature, the result was heated under reflux for 3 hours. The temperature was lowered to room temperature and produced solids were filtered. The obtained solid product was combined, washed with purified water, a mixed solvent of EtOH/MeOH and n-hexane, and dried with warm air to obtain a target compound [1,2,4]triazolo[5,1-a]isoquinoline-2-amine (1.65 g, yield 90%).

$^1$H-NMR: δ 6.31 (s, 1H), 7.60 (m, 4H), 7.99 (d, 1H), 8.45 (d, 1H), 7.97 (s, 1H), 8.59 (d, 1H), 8.98 (t, 1H)

<Step 3> Synthesis of A-1

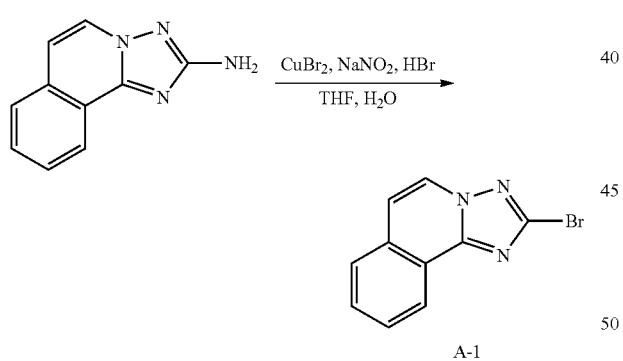

CuBr$_2$ (0.67 g, 3 mmol) and THF (20 mL) were added to [1,2,4]triazolo[5,1-a]isoquinoline-2-amine (1.84 g, 10 mmol). The reaction solution was cooled to 0° C., HBr (20 mL) was slowly added thereto, and NaNO$_2$ (1.72 g, 25 mmol) dissolved in purified water (10 mL) was slowly added dropwise thereto. The reaction solution was stirred for 12 hours at room temperature. An aqueous sodium hydroxide solution (10 mL) was added to the reaction solution, the result was stirred for 1 hour, the mixture solution was extracted with E.A (50 mL) and then washed with distilled water. The obtained organic layer was dried with anhydrous MgSO$_4$, vacuum distilled and purified using silica gel column chromatography to obtain target Compound A-1 (1.48 g, yield 60%).

$^1$H-NMR: δ 7.60 (m, 4H), 7.99 (d, 1H), 8.45 (d, 1H)

[Preparation Example 2] Synthesis of A-2

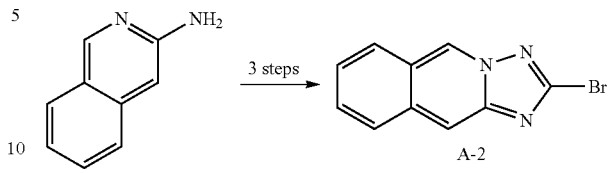

Target Compound A-2 (1.46 g, yield 59%) was obtained in the same manner as in [Preparation Example 1] except that isoquinoline-3-amine (1.44 g, 10 mmol) was used as the reactant instead of isoquinoline-1-amine.

$^1$H-NMR: δ 7.45 (m, 2H), 7.64 (m, 2H), 8.11 (d, 1H), 9.15 (s, 1H)

[Preparation Example 3] Synthesis of A-3

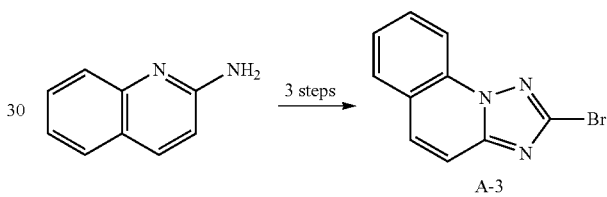

Target Compound A-3 (1.43 g, yield 58%) was obtained in the same manner as in [Preparation Example 1] except that quinoline-2-amine (1.44 g, 10 mmol) was used as the reactant instead of isoquinoline-1-amine.

$^1$H-NMR: δ 7.69 (t, 1H), 7.85 (m, 2H), 8.09 (m, 2H), 8.29 (d, 1H)

[Preparation Example 4] Synthesis of A-4

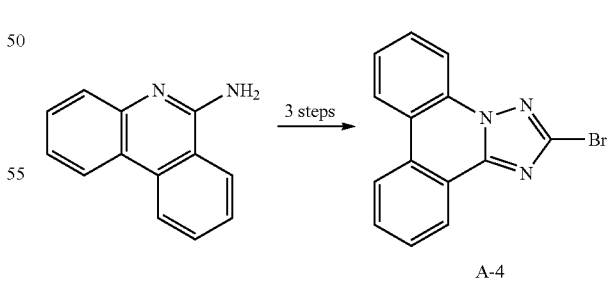

Target Compound A-4 (1.69 g, yield 57%) was obtained in the same manner as in [Preparation Example 1] except that phenanthridine-6-amine (1.94 g, 10 mmol) was used as the reactant instead of isoquinoline-1-amine.

$^1$H-NMR: δ 7.63 (m, 3H), 7.84 (m, 2H), 7.99 (d, 1H), 8.10 (m, 2H)

[Preparation Example 5] Synthesis of A-5

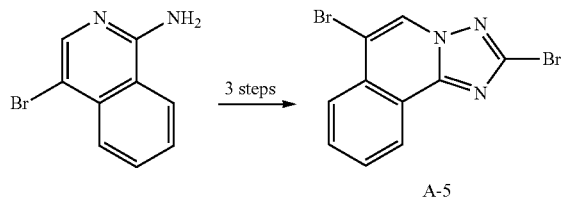

A-5

Target Compound A-5 (1.83 g, yield 56%) was obtained in the same manner as in [Preparation Example 1] except that 4-bromoisoquinoline-1-amine (2.23 g, 10 mmol) was used as the reactant instead of isoquinoline-1-amine.

$^1$H-NMR: δ 7.63 (t, 1H), 7.90 (m, 3H), 8.74 (s, 1H)

[Preparation Example 6] Synthesis of A-6

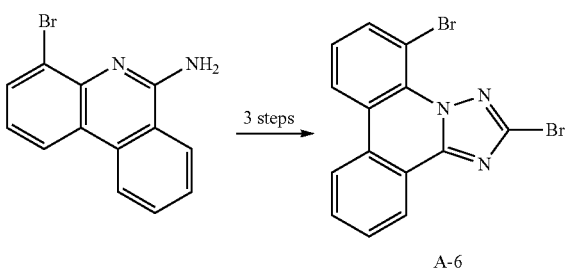

A-6

Target Compound A-6 (2.07 g, yield 55%) was obtained in the same manner as in [Preparation Example 1] except that 4-bromophenanthridine-6-amine (2.73 g, 10 mmol) was used as the reactant instead of isoquinoline-1-amine.

$^1$H-NMR: δ 7.43 (t, 1H), 7.61 (m, 2H), 7.83 (d, 1H), 7.99 (d, 1H), 8.01 (d, 1H), 8.37 (d, 1H)

[Preparation Example 7] Synthesis of A-7

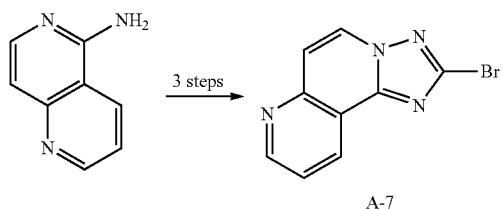

A-7

Target Compound A-7 (1.34 g, yield 54%) was obtained in the same manner as in [Preparation Example 1] except that 1,6-naphthyridine-5-amine (1.45 g, 10 mmol) was used as the reactant instead of isoquinoline-1-amine.

$^1$H-NMR: δ 7.46 (t, 1H), 7.70 (d, 1H), 8.23 (d, 1H), 8.78 (d, 1H), 9.14 (d, 1H)

[Preparation Example 8] Synthesis of A-8

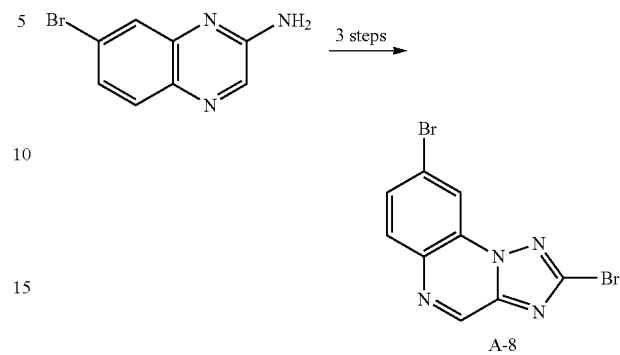

A-8

Target Compound A-8 (1.73 g, yield 53%) was obtained in the same manner as in [Preparation Example 1] except that 7-bromoquinoxaline-2-amine (2.24 g, 10 mmol) was used as the reactant instead of isoquinoline-1-amine.

$^1$H-NMR: δ 7.56 (d, 1H), 7.85 (d, 1H), 8.24 (s, 1H), 8.74 (s, 1H)

[Preparation Example 9] Synthesis of A-9

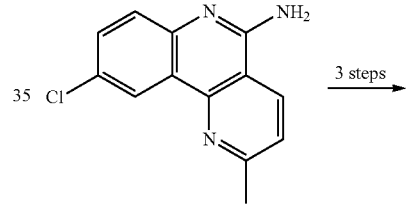

A-9

Target Compound A-9 (1.80 g, yield 52%) was obtained in the same manner as in [Preparation Example 1] except that 9-chloro-2-methylbenzo[h][1,6]naphthyridine-5-amine (2.43 g, 10 mmol) was used as the reactant instead of isoquinoline-1-amine.

$^1$H-NMR: δ 2.76 (s, 3H), 7.35 (d, 1H), 7.66 (s, 1H), 7.98 (m, 2H), 8.22 (d, 1H)

[Preparation Example 10] Synthesis of A-10

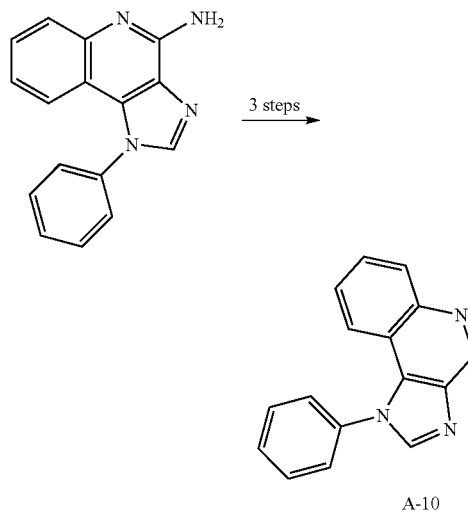

A-10

Target Compound A-10 (1.85 g, yield 51%) was obtained in the same manner as in [Preparation Example 1] except that 1-phenyl-1H-imidazo[4,5-c]quinoline-4-amine (2.60 g, 10 mmol) was used as the reactant instead of isoquinoline-1-amine.

$^1$H-NMR: δ 7.15 (s, 1H), 7.40 (m, 4H), 7.62 (t, 1H), 7.85 (m, 2H), 8.08 (d, 1H), 8.36 (d, 1H)

[Preparation Example 11] Synthesis of A-11

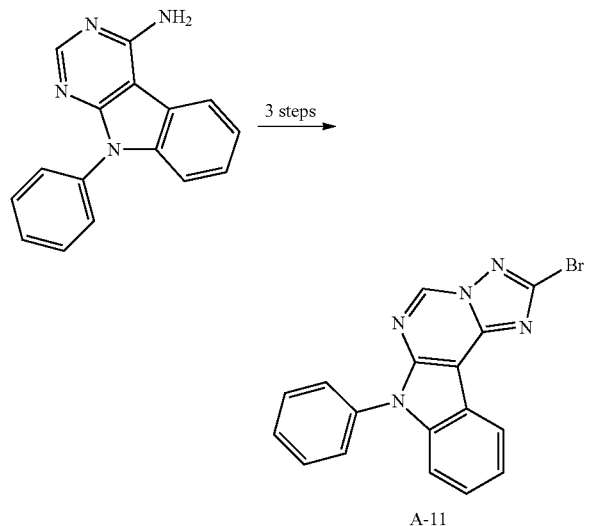

A-11

Target Compound A-11 (1.82 g, yield 50%) was obtained in the same manner as in [Preparation Example 1] except that 9-phenyl-9H-pyrimido[4,5-b]indole-4-amine (2.60 g, 10 mmol) was used as the reactant instead of isoquinoline-1-amine.

$^1$H-NMR: δ 7.16 (t, 1H), 7.35 (t, 1H), 7.60 (m, 5H), 7.94 (d, 1H), 8.55 (d, 1H), 9.54 (s, 1H)

[Preparation Example 12] Synthesis of A-12

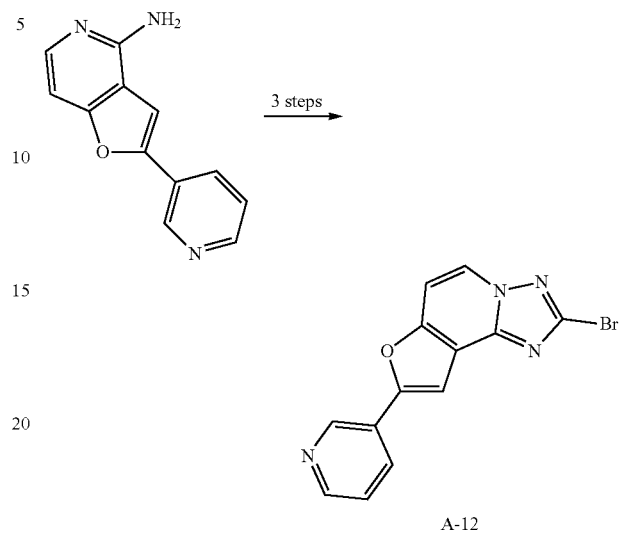

A-12

Target Compound A-12 (1.60 g, yield 51%) was obtained in the same manner as in [Preparation Example 1] except that 2-(pyridin-3-yl)furo[3,2-c]pyridine-4-amine (2.11 g, 10 mmol) was used as the reactant instead of isoquinoline-1-amine.

$^1$H-NMR: δ 6.56 (s, 1H), 7.57 (t, 1H), 7.86 (d, 1H), 8.42 (d, 1H), 8.59 (d, 1H), 8.70 (d, 1H), 9.24 (s, 1H)

[Preparation Example 13] Synthesis of A-13

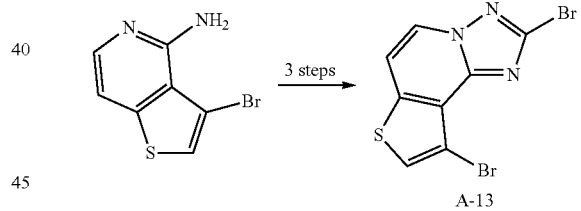

A-13

Target Compound A-13 (1.73 g, yield 52%) was obtained in the same manner as in [Preparation Example 1] except that 3-bromothieno[3,2-c]pyridine-4-amine (2.29 g, 10 mmol) was used as the reactant instead of isoquinoline-1-amine.

$^1$H-NMR: δ 7.38 (d, 1H), 8.55 (m, 2H)

[Preparation Example 14] Synthesis of A-14

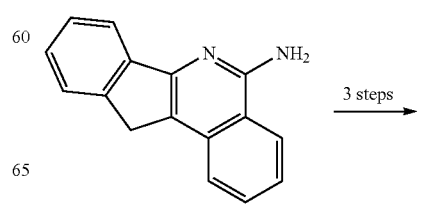

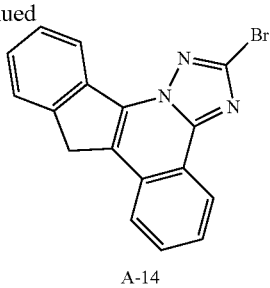

A-14

Target Compound A-14 (1.78 g, yield 53%) was obtained in the same manner as in [Preparation Example 1] except that 11H-indeno[1,2-c]isoquinoline-5-amine (2.32 g, 10 mmol) was used as the reactant instead of isoquinoline-1-amine.

$^1$H-NMR: δ 3.81 (s, 2H), 7.27 (t, 1H), 7.38 (m, 2H), 7.59 (t, 1H), 7.70 (t, 1H), 8.00 (m, 3H)

[Synthesis Example 1] Synthesis of J-1

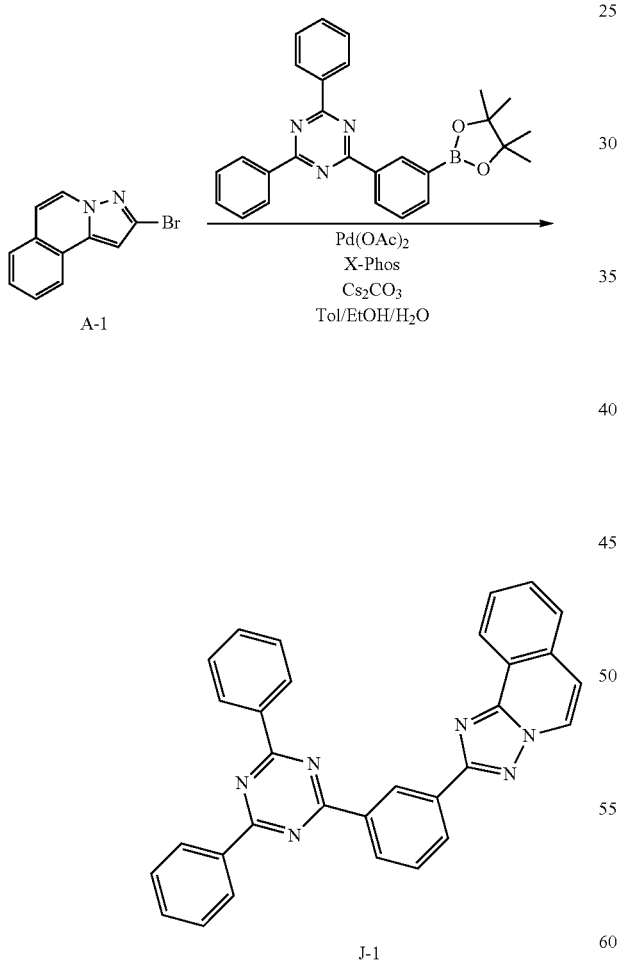

J-1

Under a nitrogen stream, A-1 (2.48 g, 10 mmol), 2,4-diphenyl-6-(3-(4,4,5,5-tetramethyl-1,3,2-dioxaborolan-2-yl)phenyl)-1,3,5-triazine (4.35 g, 10 mmol), Pd(OAc)$_2$ (0.11 g, 5 mol %), Xphos (0.47 g, 2 mmol), Cs$_2$CO$_3$ (6.51 g, 20 mmol) and toluene/EtOH/H$_2$O (80 ml/40 ml/20 ml) were mixed, and stirred for 6 hours at 110° C. After the reaction was terminated, the result was extracted with methylene chloride, and filtered using MgSO$_4$. After removing the solvent of the filtered organic layer, the result was column chromatographed to obtain target Compound J-1 (2.57 g, yield 54%).

[LCMS]: 476

[Synthesis Example 2] Synthesis of J-2

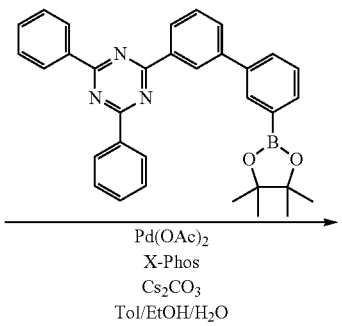

J-2

Target Compound J-2 (3.03 g, yield 55%) was obtained in the same manner as in Synthesis Example 1 except that A-2 (2.48 g, 10.0 mmol) was used instead of A-1, and 2,4-diphenyl-6-(3'-(4,4,5,5-tetramethyl-1,3,2-dioxaborolan-2-yl)-[1,1'-biphenyl]-3-yl)-1,3,5-triazine (5.11 g, 10.0 mmol) was used instead of 2,4-diphenyl-6-(3-(4,4,5,5-tetramethyl-1,3,2-dioxaborolan-2-yl)phenyl)-1,3,5-triazine.

[LCMS]: 552

[Synthesis Example 3] Synthesis of J-3
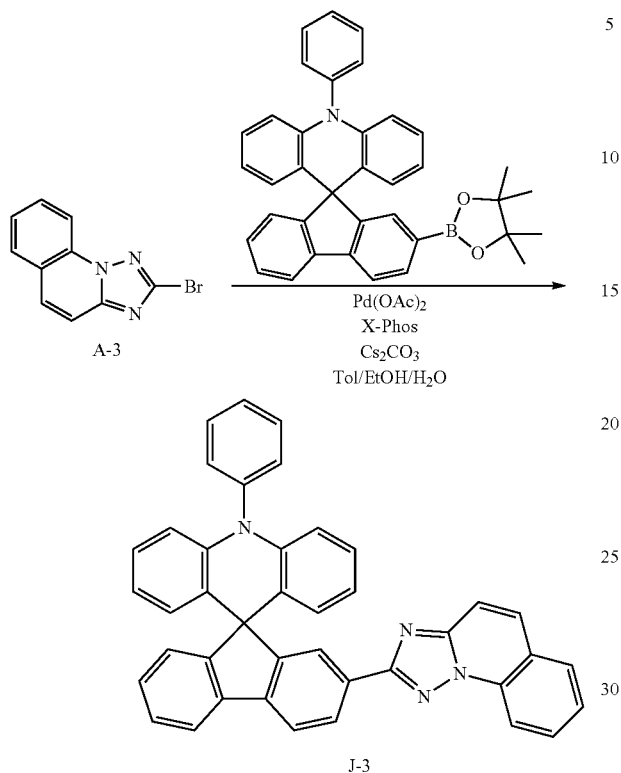
Target Compound J-3 (3.21 g, yield 56%) was obtained in the same manner as in Synthesis Example 1 except that A-3 (2.48 g, 10.0 mmol) was used instead of A-1, and 10-phenyl-2'-(4,4,5,5-tetramethyl-1,3,2-dioxaborolan-2-yl)-10H-spiro[acridine-9,9'-fluorene] (5.33 g, 10.0 mmol) was used instead of 2,4-diphenyl-6-(3-(4,4,5,5-tetramethyl-1,3,2-dioxaborolan-2-yl)phenyl)-1,3,5-triazine.
[LCMS]: 574
[Synthesis Example 4] Synthesis of J-4
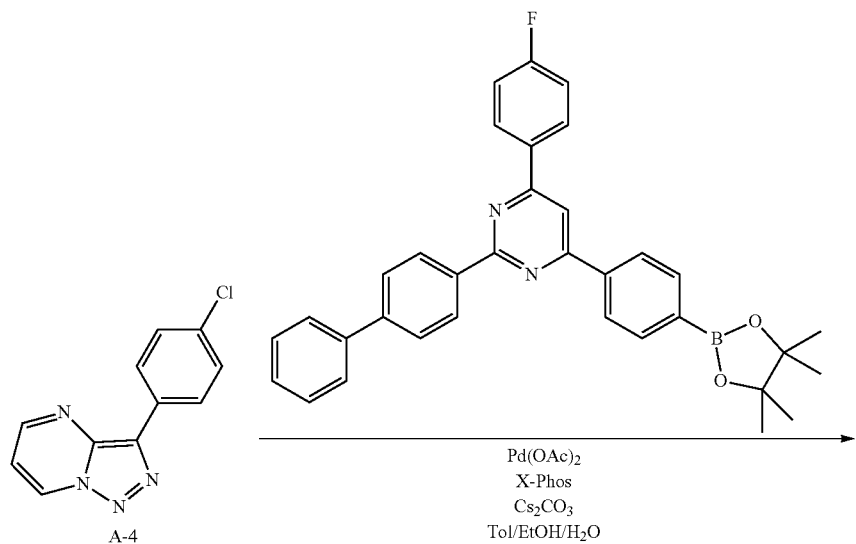

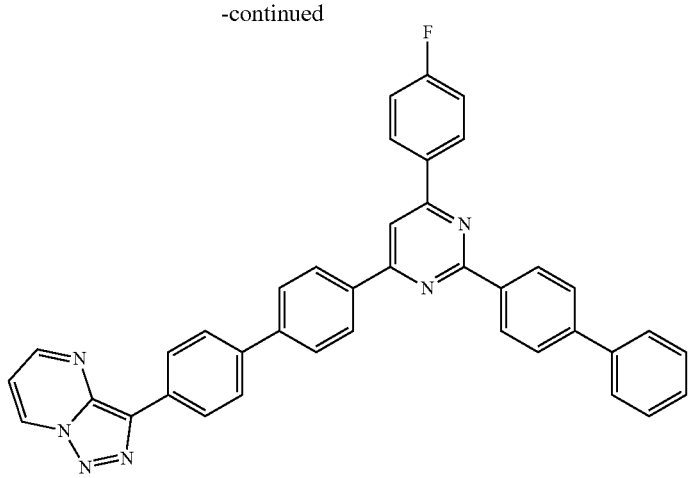

J-4

Target Compound J-4 (3.53 g, yield 57%) was obtained in the same manner as in Synthesis Example 1 except that A-4 (2.98 g, 10.0 mmol) was used instead of A-1, and 2-([1,1'-biphenyl]-4-yl)-4-(4-fluorophenyl)-6-(4-(4,4,5,5-tetramethyl-1,3,2-dioxaborolan-2-yl)phenyl)pyrimidine (5.28 g, 10.0 mmol) was used instead of 2,4-diphenyl-6-(3-(4,4,5,5-tetramethyl-1,3,2-dioxaborolan-2-yl)phenyl)-1,3,5-triazine.

[LCMS]: 619

Target Compound J-5 (4.81 g, yield 58%) was obtained in the same manner as in Synthesis Example 1 except that A-5 (3.26 g, 10.0 mmol) was used instead of A-1, and 4,4,5,5-tetramethyl-2-(4-(1,2,2-triphenylvinyl)phenyl)-1,3,2-dioxaborolane (9.16 g, 20.0 mmol) was used instead of 2,4-diphenyl-6-(3-(4,4,5,5-tetramethyl-1,3,2-dioxaborolan-2-yl)phenyl)-1,3,5-triazine.

[LCMS]: 830

[Synthesis Example 5] Synthesis of J-5

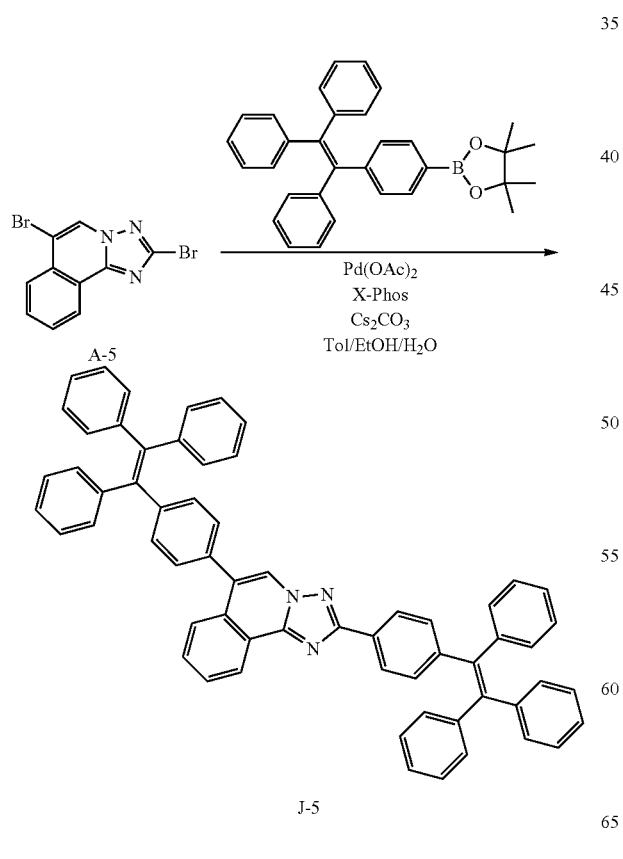

[Synthesis Example 6] Synthesis of J-6

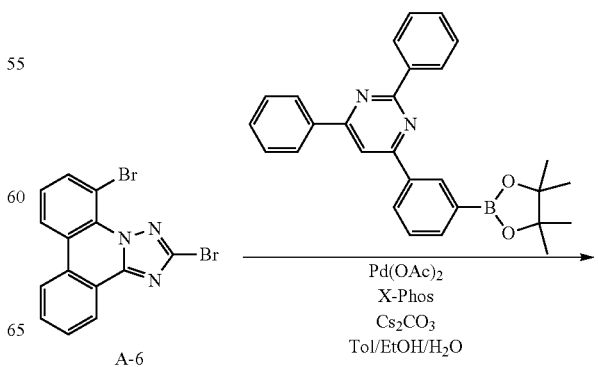

-continued

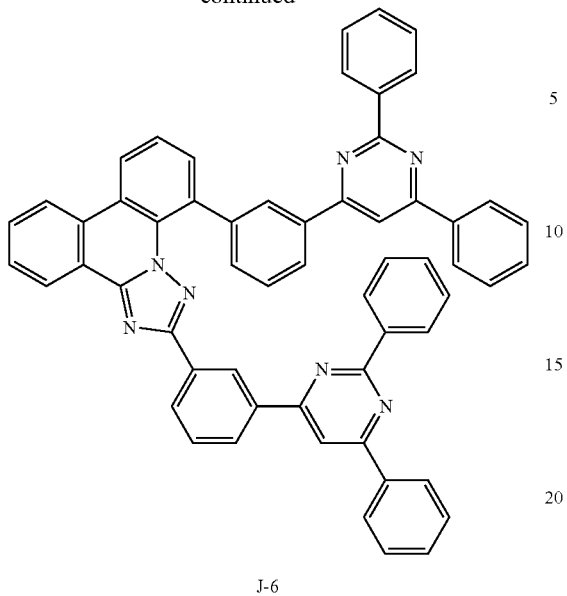

J-6

Target Compound J-6 (4.90 g, yield 59%) was obtained in the same manner as in Synthesis Example 1 except that A-6 (3.77 g, 10.0 mmol) was used instead of A-1, and 2,4-diphenyl-6-(3-(4,4,5,5-tetramethyl-1,3,2-dioxaborolan-2-yl)phenyl)pyrimidine (8.68 g, 20.0 mmol) was used instead of 2,4-diphenyl-6-(3-(4,4,5,5-tetramethyl-1,3,2-dioxaborolan-2-yl)phenyl)-1,3,5-triazine.

[LCMS]: 831

[Synthesis Example 7] Synthesis of J-7

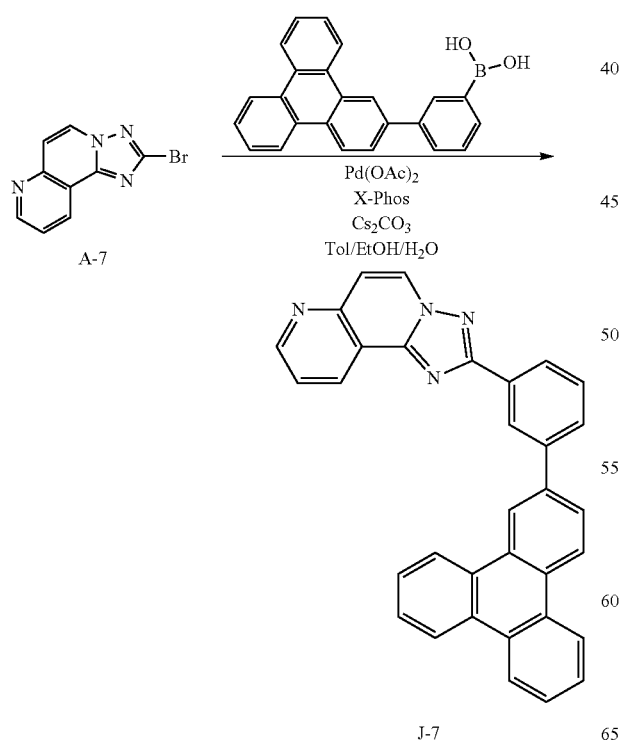

Target Compound J-7 (2.83 g, yield 60%) was obtained in the same manner as in Synthesis Example 1 except that A-7 (2.49 g, 10.0 mmol) was used instead of A-1, and (3-(triphenylen-2-yl)phenyl)boronic acid (3.48 g, 10.0 mmol) was used instead of 2,4-diphenyl-6-(3-(4,4,5,5-tetramethyl-1,3,2-dioxaborolan-2-yl)phenyl)-1,3,5-triazine.

[LCMS]: 472

[Synthesis Example 8] Synthesis of J-8

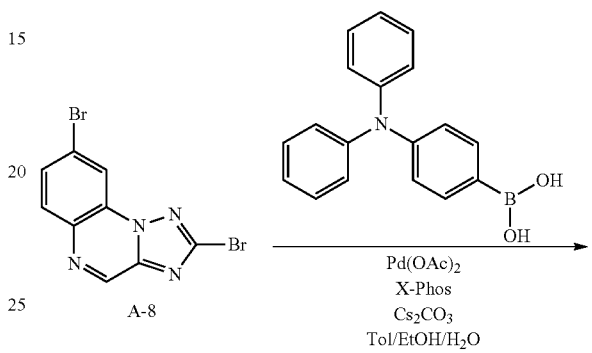

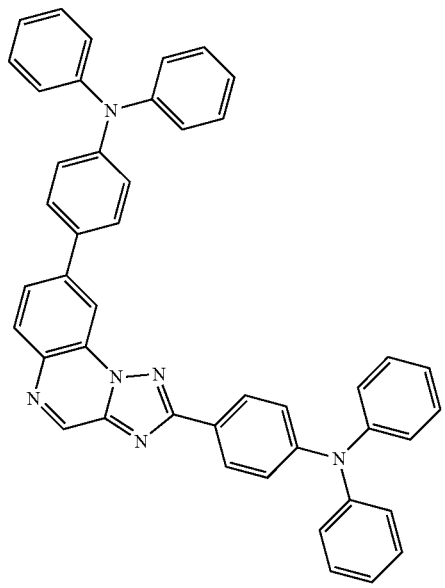

J-8

Target Compound J-8 (3.87 g, yield 59%) was obtained in the same manner as in Synthesis Example 1 except that A-8 (3.27 g, 10.0 mmol) was used instead of A-1, and (4-(diphenylamino)phenyl)boronic acid (5.78 g, 20.0 mmol) was used instead of 2,4-diphenyl-6-(3-(4,4,5,5-tetramethyl-1,3,2-dioxaborolan-2-yl)phenyl)-1,3,5-triazine.

[LCMS]: 656

[Synthesis Example 9] Synthesis of J-9
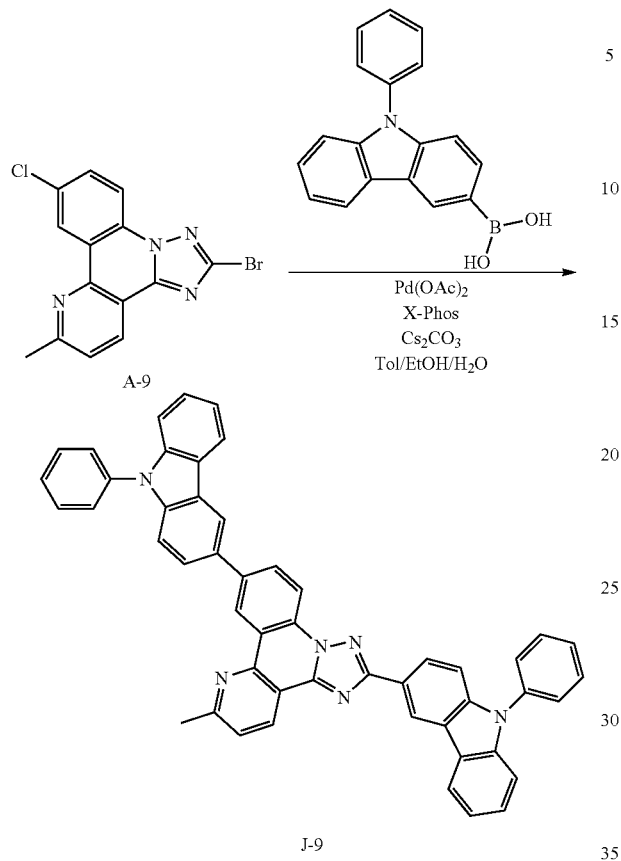
Target Compound J-9 (4.15 g, yield 58%) was obtained in the same manner as in Synthesis Example 1 except that A-9 (3.47 g, 10.0 mmol) was used instead of A-1, and (9-phenyl-9H-carbazol-3-yl)boronic acid (5.74 g, 20.0 mmol) was used instead of 2,4-diphenyl-6-(3-(4,4,5,5-tetramethyl-1,3,2-dioxaborolan-2-yl)phenyl)-1,3,5-triazine.
[LCMS]: 716
[Synthesis Example 10] Synthesis of J-10
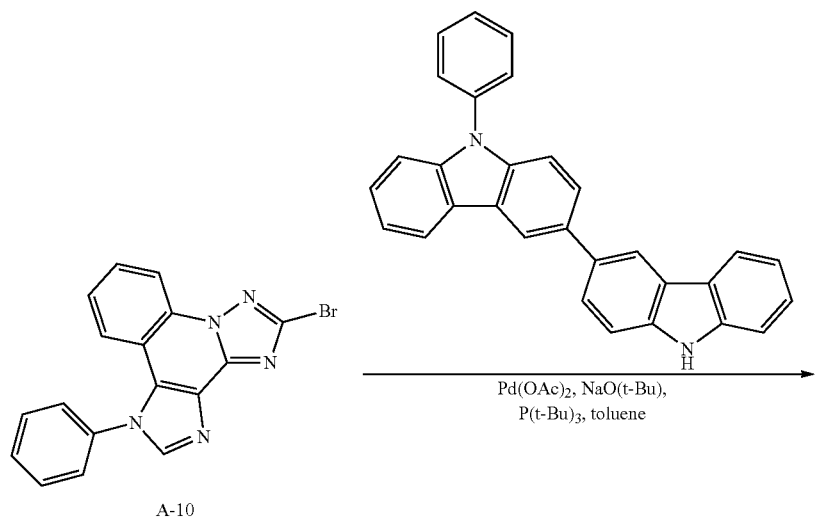

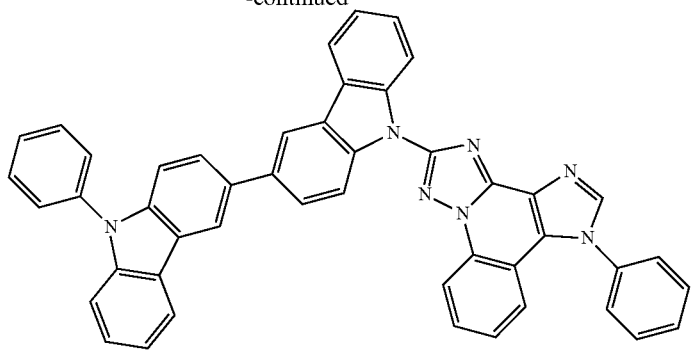

J-10

Under a nitrogen stream, A-10 (3.64 g, 10 mmol), 9-phenyl-9H,9'H-3,3'-bicarbazole (4.08 g, 10 mmol), Pd(OAc)$_2$ (0.11 g, 5 mol %), P(t-Bu)$_3$ (0.20 g, 1 mmol), NaO(t-Bu) (1.92 g, 20 mmol) and toluene (200 ml) were mixed, and stirred for 12 hours at 110° C. After the reaction was terminated, the result was extracted with methylene chloride, and filtered using MgSO$_4$. After removing the solvent from the filtered organic layer, the result was column chromatographed to obtain target Compound J-10 (3.94 g, yield 57%).

[LCMS]: 691

[Synthesis Example 11] Synthesis of J-11

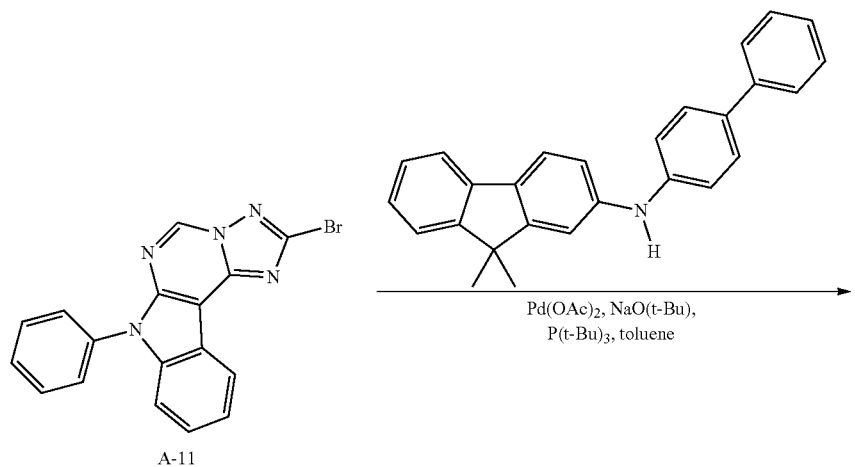

A-11

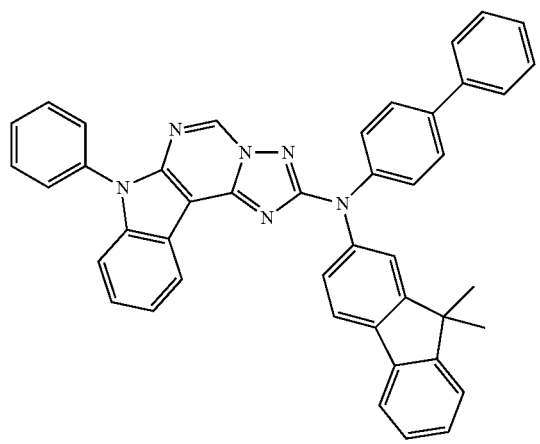

J-11

Target Compound J-11 (3.61 g, yield 56%) was obtained in the same manner as in Synthesis Example 10 except that A-11 (3.64 g, 10.0 mmol) was used instead of A-10, and N-([1,1'-biphenyl]-4-yl)-9,9-dimethyl-9H-fluorene-2-amine (3.61 g, 10.0 mmol) was used instead of 9-phenyl-9H,9'H-3,3'-bicarbazole.

[LCMS]: 644

[Synthesis Example 12] Synthesis of J-12

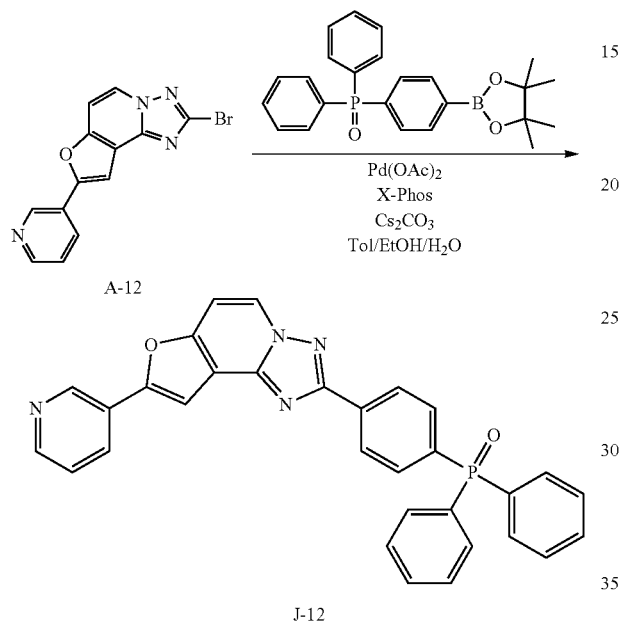

Target Compound J-12 (2.81 g, yield 55%) was obtained in the same manner as in Synthesis Example 1 except that A-12 (3.15 g, 10.0 mmol) was used instead of A-1, and diphenyl(4-(4,4,5,5-tetramethyl-1,3,2-dioxaborolan-2-yl)phenyl)phosphine oxide (4.04 g, 10.0 mmol) was used instead of 2,4-diphenyl-6-(3-(4,4,5,5-tetramethyl-1,3,2-dioxaborolan-2-yl)phenyl)-1,3,5-triazine.

[LCMS]: 512

[Synthesis Example 13] Synthesis of J-13

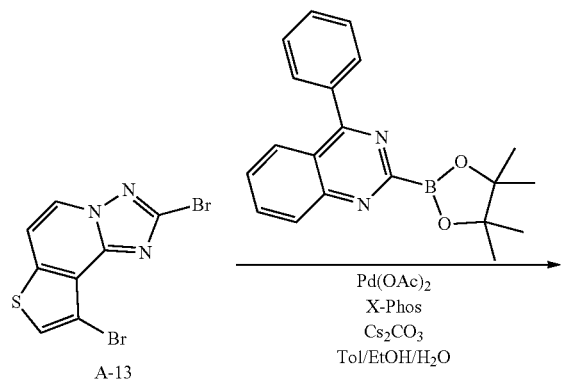

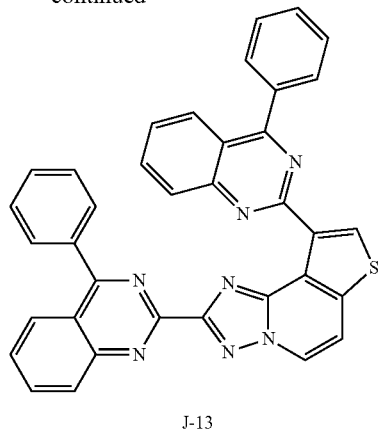

Target Compound J-13 (3.15 g, yield 54%) was obtained in the same manner as in Synthesis Example 1 except that A-13 (3.33 g, 10.0 mmol) was used instead of A-1, and 4-phenyl-2-(4,4,5,5-tetramethyl-1,3,2-dioxaborolan-2-yl)quinazoline (6.64 g, 20.0 mmol) was used instead of 2,4-diphenyl-6-(3-(4,4,5,5-tetramethyl-1,3,2-dioxaborolan-2-yl)phenyl)-1,3,5-triazine.

[LCMS]: 583

[Synthesis Example 14] Synthesis of J-14

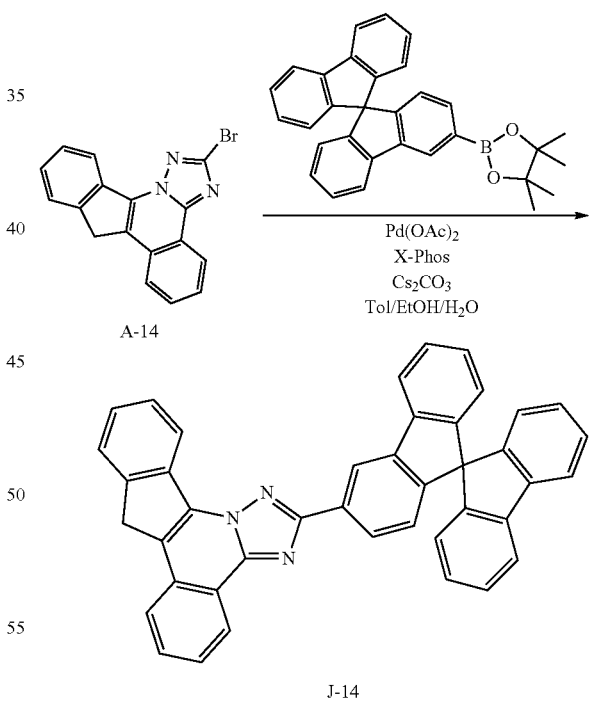

Target Compound J-14 (3.02 g, yield 53%) was obtained in the same manner as in Synthesis Example 1 except that A-14 (3.36 g, 10.0 mmol) was used instead of A-1, and 2-(9,9'-spirobi[fluoren]-3-yl)-4,4,5,5-tetramethyl-1,3,2-dioxaborolane (4.42 g, 10.0 mmol) was used instead of 2,4-diphenyl-6-(3-(4,4,5,5-tetramethyl-1,3,2-dioxaborolan-2-yl)phenyl)-1,3,5-triazine.

[LCMS]: 571

[Examples 1 to 7] Manufacture of Blue Organic Electroluminescent Devices

After high purity sublimation purifying Compounds J-1 to J-7 synthesized in the synthesis examples using commonly known methods, blue organic electroluminescent devices were manufactured as follows.

First, a glass substrate on which indium tin oxide (ITO) was coated as a thin film to a thickness of 1500 Å was ultrasonic cleaned using distilled water. After the cleaning with distilled water was finished, the substrate was ultrasonic cleaned with solvents of isopropyl alcohol, acetone, methanol and the like, dried, then transferred to a UV OZONE washer (Power sonic 405, manufactured by Hwashin Tech. Co., Ltd.), and then, after cleaning the substrate for 5 minutes using UV, the substrate was transferred to a vacuum deposition apparatus.

On the transparent ITO electrode prepared as above, DS-205 (Doosan Corporation Electro-Materials, 80 nm)/NPB (15 nm)/ADN+5% DS-405 (Doosan Corporation Electro-Materials, 30 nm)/each compound of Compounds J-1 to J-7 (30 nm)/LiF (1 nm)/Al (200 nm) were laminated in this order to manufacture an organic electroluminescent device.

[Comparative Example 1] Manufacture of Blue Organic Electroluminescent Device

A blue organic electroluminescent device was manufactured in the same manner as in Example 1 except that $Alq_3$ was used instead of Compound J-1 as the electron transport layer material.

[Comparative Example 2] Manufacture of Blue Organic Electroluminescent Device

A blue organic electroluminescent device was manufactured in the same manner as in Example 1 except that Compound J-1 was not used as the electron transport layer material.

Structures of the NPB, the ADN and the Alq3 used in Examples 1 to 7 and Comparative Examples 1 and 2 are as follows.

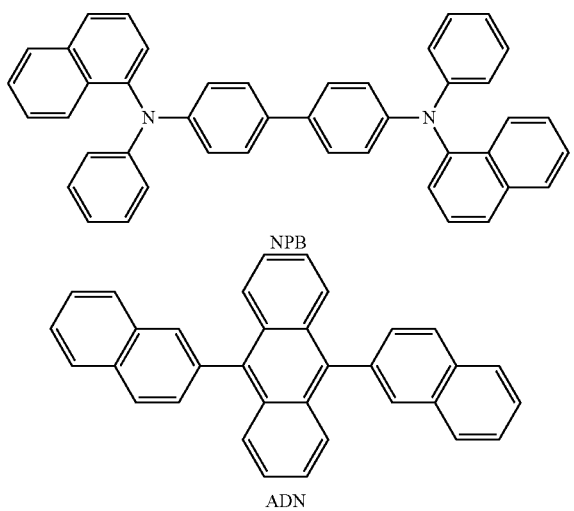

NPB

ADN

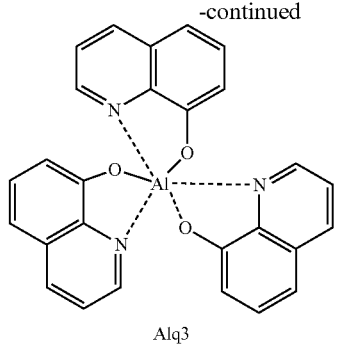

Alq3

Evaluation Example 1

For the blue organic electroluminescent devices each manufactured in Examples 1 to 7 and Comparative Examples 1 and 2, driving voltage, current efficiency and light emission wavelength at current density of 10 mA/cm² were measured, and the results are shown in the following Table 1.

TABLE 1

| Sample | Electron Transport Layer | Driving Voltage (V) | Light Emission Peak (nm) | Current Efficiency (cd/A) |
|---|---|---|---|---|
| Example 1 | J-1 | 3.9 | 454 | 8.1 |
| Example 2 | J-2 | 3.7 | 457 | 7.8 |
| Example 3 | J-3 | 3.8 | 457 | 8.4 |
| Example 4 | J-4 | 3.6 | 452 | 8.7 |
| Example 5 | J-5 | 4.5 | 455 | 8.6 |
| Example 6 | J-6 | 3.4 | 452 | 8.4 |
| Example 7 | J-7 | 3.8 | 453 | 9.0 |
| Comparative Example 1 | Alq$_3$ | 5.4 | 458 | 5.5 |
| Comparative Example 2 | — | 4.9 | 460 | 5.8 |

As shown in Table 1, it was seen that the blue organic electroluminescent devices using the compound of the present invention in an electron transport layer (Examples 1 to 7) exhibited excellent performance in terms of driving voltage, light emission peak and current efficiency compared to the blue organic electroluminescent device using existing Alq$_3$ in an electron transport layer (Comparative Example 1) and the blue organic electroluminescent device without an electron transport layer (Comparative Example 2).

[Examples 8 to 14] Manufacture of Blue Organic Electroluminescent Devices

After high purity sublimation purifying Compounds J-8 to J-14 synthesized in the synthesis examples using commonly known methods, blue organic electroluminescent devices were manufactured using the following procedure.

First, a glass substrate on which indium tin oxide (ITO) was coated as a thin film to a thickness of 1500 Å was ultrasonic cleaned using distilled water. After the cleaning with distilled water was finished, the substrate was ultrasonic cleaned with solvents of isopropyl alcohol, acetone, methanol and the like, dried, then transferred to a UV OZONE washer (Power sonic 405, manufactured by Hwashin Tech. Co., Ltd.), and then, after cleaning the substrate for 5 minutes using UV, the substrate was transferred to a vacuum deposition apparatus.

On the transparent ITO electrode prepared as above, DS-205 (Doosan Corporation Electro-Materials, 80 nm)/NPB (15 nm)/ADN+5% DS-405 (Doosan Corporation Electro-Materials, 30 nm)/each compound of Compounds J-8 to J-14 (5 nm)/Alq$_3$ (25 nm)/LiF (1 nm)/Al (200 nm) were laminated in this order to manufacture an organic electroluminescent device.

[Comparative Example 3] Manufacture of Blue Organic Electroluminescent Device

A blue organic electroluminescent device was manufactured in the same manner as in Example 8 except that Compound J-8 was not used as the hole blocking layer material, and the Alq$_3$, an electron transport layer material, was deposited to 30 nm instead of 25 nm.

Evaluation Example 2

For the blue organic electroluminescent devices each manufactured in Examples 8 to 14 and Comparative Example 3, driving voltage, light emission wavelength and current efficiency at current density of 10 mA/cm$^2$ were measured, and the results are shown in the following Table 2.

TABLE 2

| Sample | Hole Blocking Layer | Driving Voltage (V) | Light Emission Peak (nm) | Current Efficiency (cd/A) |
| --- | --- | --- | --- | --- |
| Example 8 | J-8 | 4.2 | 452 | 8.1 |
| Example 9 | J-9 | 3.7 | 451 | 8.1 |
| Example 10 | J-10 | 4.7 | 452 | 7.7 |
| Example 11 | J-11 | 3.8 | 454 | 8.3 |
| Example 12 | J-12 | 3.7 | 451 | 7.4 |
| Example 13 | J-13 | 4.1 | 452 | 8.1 |
| Example 14 | J-14 | 4.5 | 453 | 7.7 |
| Comparative Example 3 | — | 4.8 | 458 | 6.0 |

As shown in Table 2, it was seen that the blue organic electroluminescent devices using the compound of the present invention in a hole blocking layer (Examples 8 to 14) exhibited excellent performance in terms of current efficiency, light emission peak and driving voltage compared to the blue organic electroluminescent device without a hole blocking layer (Comparative Example 3).

The present invention relates to a novel organic compound capable of being used as a material for an organic electroluminescent device, and an organic electroluminescent device including the same.

The invention claimed is:

1. A compound represented by any one of the following Chemical Formulae 3 to 6:

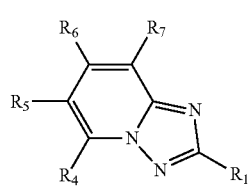

[Chemical Formula 3]

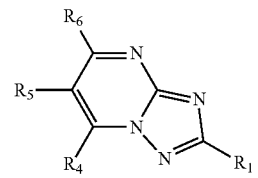

[Chemical Formula 4]

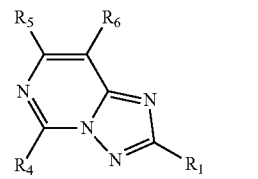

[Chemical Formula 5]

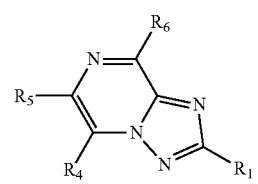

[Chemical Formula 6]

wherein, in Chemical Formulae 3 to 6,
R$_1$ and R$_4$ to R$_7$ are each independently a substituent represented by the following Chemical Formula 2;

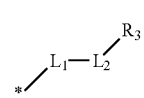

[Chemical Formula 2]

in Chemical Formula 2,
* means a part where a bond is formed;
L$_1$ and L$_2$ are each independently selected from the group consisting of a single bond, a C$_6$~C$_{18}$ arylene group and a heteroarylene group having 5 to 18 nuclear atoms;
R$_3$ is selected from the group consisting of hydrogen, deuterium, halogen, a cyano group, a nitro group, a C$_1$~C$_{40}$ alkyl group, a C$_2$~C$_{40}$ alkenyl group, a C$_2$~C$_{40}$ alkynyl group, a C$_3$~C$_{40}$ cycloalkyl group, a heterocycloalkyl group having 3 to 40 nuclear atoms, a C$_6$~C$_{60}$ aryl group, a heteroaryl group having 5 to 60 nuclear atoms, a C$_1$~C$_{40}$ alkyloxy group, a C$_6$~C$_{60}$ aryloxy group, a C$_3$~C$_{40}$ alkylsilyl group, a C$_6$~C$_{60}$ arylsilyl group, a C$_1$~C$_{40}$ alkylsulfonyl group, a C$_6$~C$_{60}$ arylsulfonyl group, a C$_1$~C$_{40}$ alkylboron group, a C$_6$~C$_{60}$ arylboron group, a C$_6$~C$_{60}$ arylphosphanyl group, a C$_6$~C$_{60}$ mono or diarylphosphinyl group, a C$_1$~C$_{40}$ alkylcarbonyl group, a C$_6$~C$_{60}$ arylcarbonyl group and a C$_6$~C$_{60}$ arylamine group, or bonds to an adjacent group to form an aromatic ring having 5 to 50 nuclear atoms, a non-aromatic fused polycyclic ring having 5 to 50 nuclear atoms, an aromatic heteroring having 5 to 50 nuclear atoms, or a non-aromatic fused heteropolycyclic ring having 5 to 50 nuclear atoms; and
the arylene group and the heteroarylene group of L$_1$ and L$_2$, the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_3$, and the aromatic ring, the non-aromatic fused polycyclic ring, the aromatic heteroring and the non-aromatic fused heteropolycyclic ring formed by adjacent two $R_3$s bonding to each other are each independently unsubstituted or substituted with one or more types of substituents selected from the group consisting of deuterium, halogen, a cyano group, a nitro group, a $C_1\text{~}C_{40}$ alkyl group, a $C_2\text{~}C_{40}$ alkenyl group, a $C_2\text{~}C_{40}$ alkynyl group, a $C_6\text{~}C_{60}$ aryl group, a heteroaryl group having 5 to 60 nuclear atoms, a $C_6\text{~}C_{60}$ aryloxy group, a $C_1\text{~}C_{40}$ alkyloxy group, a $C_6\text{~}C_{60}$ arylamine group, a $C_3\text{~}C_{40}$ cycloalkyl group, a heterocycloalkyl group having 3 to 40 nuclear atoms, a $C_1\text{~}C_{40}$ alkylsilyl group, a $C_1\text{~}C_{40}$ alkylboron group, a $C_6\text{~}C_{60}$ arylboron group, a $C_6\text{~}C_{60}$ arylphosphanyl group, a $C_6\text{~}C_{60}$ mono or diarylphosphinyl group, a $C_1\text{~}C_{40}$ alkylcarbonyl group, a $C_6\text{~}C_{60}$ arylcarbonyl group and a $C_6\text{~}C_{60}$ arylsilyl group, and when substituted with a plurality of the substituents, these are the same as or different from each other;

wherein one or more of $R_4$ and $R_5$, $R_5$ and $R_6$, and $R_6$ and $R_7$ each independently form a fused ring with a ring represented by any one of the following Chemical Formulae 8 to 11, 13 and 14, with proviso that $R_5$ and $R_6$ of Chemical Formula 5 do not form a ring of Chemical Formula 13:

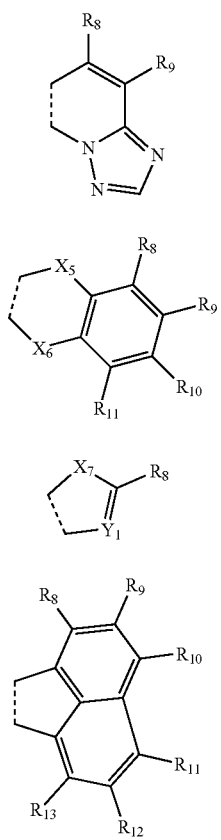

[Chemical Formula 8]

[Chemical Formula 9]

[Chemical Formula 10]

[Chemical Formula 11]

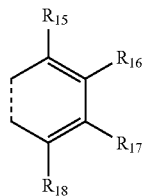

[Chemical Formula 13]

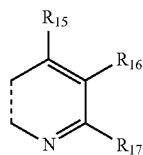

[Chemical Formula 14]

in Chemical Formulae 8 to 11, 13 and 14, a dotted line means a part that is fused;

$X_5$ and $X_6$ are each independently selected from the group consisting of a single bond, O, $N(Ar_7)$ $C(Ar_2)(Ar_3)$, S, $Si(Ar_4)(Ar_5)$ and $P(=O)(Ar_6)$, however, $X_5$ and $X_6$ are not both a single bond, and when any one of $X_5$ and $X_6$ is a single bond, the other is not $N(Ar_7)$;

$Y_1$ is N or $C(Ar_1)$, and when $Ar_1$ is present in plural numbers, these are the same as or different from each other;

$X_7$ is O, $N(Ar_7)$ or S;

$Ar_1$ to $Ar_7$, $R_8$ to $R_{13}$ and $R_{15}$ to $R_{18}$ are each independently a substituent represented by the Chemical Formula 2;

wherein, when all of $R_4$ to $R_7$ that do not form a fused ring are hydrogen and $R_{15}$ to $R_{18}$ are also hydrogen, $R_1$ is selected from the group consisting of a $C_2\text{~}C_{40}$ alkenyl group, a $C_6\text{~}C_{60}$ aryl group, a heteroaryl group having 5 to 60 nuclear atoms, a $C_3\text{~}C_{40}$ alkylsilyl group, a $C_6\text{~}C_{60}$ arylsilyl group, a $C_1\text{~}C_{40}$ alkylsulfonyl group, a $C_6\text{~}C_{60}$ arylsulfonyl group, a $C_1\text{~}C_{40}$ alkylboron group, a $C_6\text{~}C_{60}$ arylboron group, a $C_6\text{~}C_{60}$ arylphosphanyl group, a $C_6\text{~}C_{60}$ mono or diarylphosphinyl group, a $C_1\text{~}C_{40}$ alkylcarbonyl group, a $C_6\text{~}C_{60}$ arylcarbonyl group and a $C_6\text{~}C_{60}$ arylamine group; and the alkenyl group, the aryl group, the heteroaryl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_1$ and $R_3$ are each independently unsubstituted or substituted with one or more types of substituents selected from the group consisting of halogen, a cyano group, a $C_1\text{~}C_{40}$ alkyl group, a $C_2\text{~}C_{40}$ alkenyl group, a $C_2\text{~}C_{40}$ alkynyl group, a $C_6\text{~}C_{60}$ aryl group and a heteroaryl group having 5 to 60 nuclear atoms, and when substituted with a plurality of the substituents, these are the same as or different from each other.

2. The compound of claim 1, wherein one or more of $R_{15}$ and $R_{16}$, $R_{16}$ and $R_{17}$, and $R_{17}$ and $R_{18}$ each independently form a fused ring with a ring represented by the following Chemical Formula 16:

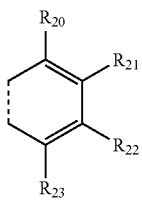

[Chemical Formula 16]

in Chemical Formula 16,
a dotted line means a part that is fused;
$R_{20}$ to $R_{23}$ are each independently a substituent represented by the following Chemical Formula 17:

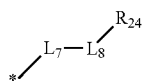

[Chemical Formula 17]

in Chemical Formula 17,
* means a part where a bond is formed;
$L_7$ and $L_8$ are each independently selected from the group consisting of a single bond, a $C_6$~$C_{18}$ arylene group and a heteroarylene group having 5 to 18 nuclear atoms;
$R_{24}$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group; and
the arylene group and the heteroarylene group of $L_7$ and $L_8$, and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_{24}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

3. The compound of claim 1, wherein the ring represented by Chemical Formula 8 is represented by the following Chemical Formula 18:

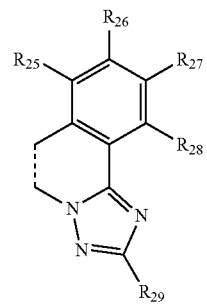

[Chemical Formula 18]

in Chemical Formula 18,
a dotted line means a part that is fused;
$R_{25}$ to $R_{29}$ are each independently a substituent represented by the following Chemical Formula 15;

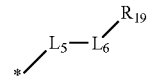

[Chemical Formula 15]

in Chemical Formula 15,
* means a part where a bond is formed;
$L_5$ and $L_6$ are each independently selected from the group consisting of a single bond, a $C_6$~$C_{18}$ arylene group and a heteroarylene group having 5 to 18 nuclear atoms;
$R_{19}$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, or bonds to an adjacent group to form an aromatic ring having 5 to 50 nuclear atoms, a non-aromatic fused polycyclic ring having 5 to 50 nuclear atoms, an aromatic heteroring having 5 to 50 nuclear atoms, or a non-aromatic fused heteropolycyclic ring having 5 to 50 nuclear atoms; and
the arylene group and the heteroarylene group of $L_5$ and $L_6$, the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_{19}$, and the aromatic ring, the non-aromatic fused polycyclic ring, the aromatic heteroring and the non-aromatic fused heteropolycyclic ring formed by adjacent two substituents bonding to each other are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

4. The compound of claim 1, wherein, in the ring represented by Chemical Formula 9, any one of $X_5$ and $X_6$ is a single bond, and the other one is O, a $C(Ar_2)(Ar_3)$, S, $Si(Ar_4)(Ar_5)$ or $P(=O)(Ar_6)$;

$Ar_2$ to $Ar_6$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $Ar_2$ to $Ar_6$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

5. The compound of claim 1, wherein the ring represented by Chemical Formula 9 is represented by the following Chemical Formula 19 or 20:

[Chemical Formula 19]

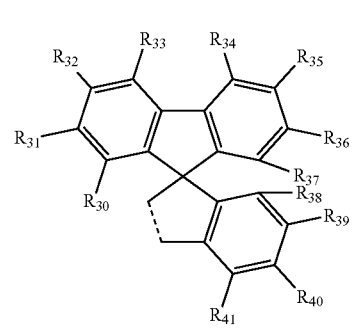

[Chemical Formula 20]

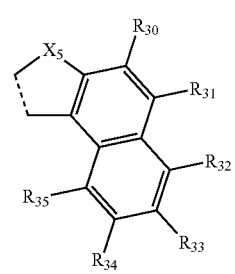

in Chemical Formulae 19 and 20, a dotted line means a part that is fused;

$X_5$ is O, N, a $C(Ar_2)(Ar_3)$, S, $Si(Ar_4)(Ar_5)$ or $P(=O)(Ar_6)$;

$Ar_2$ to $Ar_6$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group;

the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $Ar_2$ to $Ar_6$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other;

$R_{30}$ to $R_{41}$ are each independently a substituent represented by the following Chemical Formula 15;

[Chemical Formula 15]

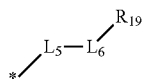

in Chemical Formula 15,
* means a part where a bond is formed;
$L_5$ and $L_6$ are each independently selected from the group consisting of a single bond, a $C_6$~$C_{18}$ arylene group and a heteroarylene group having 5 to 18 nuclear atoms;
$R_{19}$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, or bonds to an adjacent group to form an aromatic ring having 5 to 50 nuclear atoms, a non-aromatic fused polycyclic ring having 5 to 50 nuclear atoms, an aromatic heteroring having 5 to 50 nuclear atoms, or a non-aromatic fused heteropolycyclic ring having 5 to 50 nuclear atoms; and the arylene group and the heteroarylene group of $L_5$ and $L_6$, the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_{19}$, and the aromatic ring, the non-aromatic fused polycyclic ring, the aromatic heteroring and the non-aromatic fused heteropolycyclic ring formed by adjacent two substituents bonding to each other are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

6. The compound of claim 1, wherein $L_1$ and $L_2$ are each independently selected from the group consisting of a single bond, a phenylene group, a biphenylene group, a naphthalenyl group, a quinazolinyl group, a carbazolyl group and a fluorenyl group.

7. The compound of claim 1, wherein $L_1$ and $L_2$ are each independently a single bond or a linker represented by any one of the following Chemical Formulae A-1 to A-6:

A-1
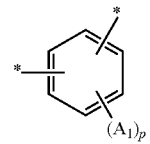

A-2
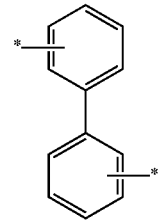

A-3
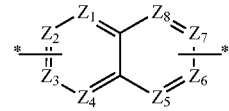

A-4
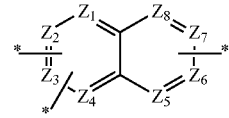

A-5
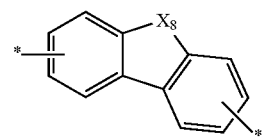

A-6
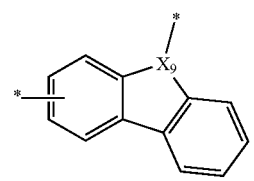

in Chemical Formulae A-1 to A-6,
* means a part where a bond is formed;
p is an integer of 0 to 4;
$A_1$ is selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, and when $A_1$ is present in plural numbers, these are the same as or different from each other;

$Z_1$ to $Z_8$ are each independently N or $C(Ar_8)$;

any one of $Z_1$ to $Z_4$ and any one of $Z_5$ to $Z_8$ bonding as a linker in Chemical Formula A-3 are $C(Ar_8)$, and herein, $Ar_8$ is not present;

any two of $Z_1$ to $Z_4$ bonding as a linker in Chemical Formula A-4 are $C(Ar_8)$, and herein, $Ar_8$ is not present;

$X_8$ is O, S, $N(Ar_9)$ or $C(Ar_{10})(Ar_{11})$;

$X_9$ is N or $C(Ar_{12})$;

$Ar_8$ to $Ar_{12}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group, and when $Ar_8$ is present in plural numbers, these are the same as or different from each other; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $A_1$ and $Ar_8$ to $Ar_{12}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

8. The compound of claim 1, wherein at least one of $R_1$ and $R_3$ is each independently selected from the group consisting of a $C_2$~$C_{40}$ alkenyl group, a $C_6$~$C_{60}$ aryl group, a heteroaryl group having 5 to 60 nuclear atoms, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group; and the alkenyl group, the aryl group, the heteroaryl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_1$ and $R_3$ are each independently unsubstituted or substituted with one or more types of substituents selected from the group consisting of halogen, a cyano group, a $C_1$~$C_{40}$ alkyl group, a $C_2$~$C_{40}$ alkenyl group, a $C_2$~$C_{40}$ alkynyl group, a $C_6$~$C_{60}$ aryl group and a heteroaryl group having 5 to 60 nuclear atoms, and when substituted with a plurality of the substituents, these are the same as or different from each other.

9. The compound of claim 1, wherein at least one of $R_1$ and $R_3$ is each independently a substituent represented by any one of the following Chemical Formulae B-1 to B-7:

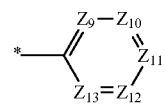

B-1

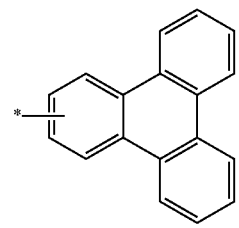

B-2

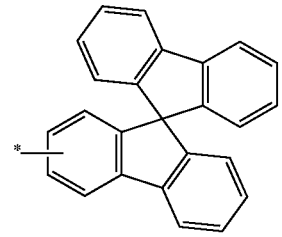

B-3

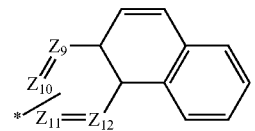

B-4

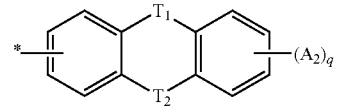

B-5

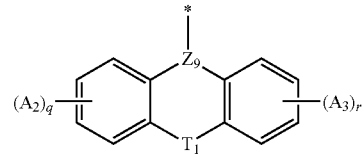

B-6

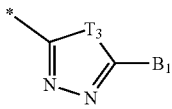

in Chemical Formulae B-1 to B-7,
* means a part where a bond is formed;

$Z_9$ to $Z_{13}$ are each independently N or $C(Ar_{13})$;

any one of $Z_9$ to $Z_{12}$ forming a bond as a substituent in Chemical Formula B-4 is $C(Ar_{13})$, and herein, $Ar_{13}$ is present;

$T_1$ and $T_2$ are each independently selected from the group consisting of a single bond, a $C(Ar_{14})(Ar_{15})$, $N(Ar_{16})$, O, S, $S(=O)(=O)$, $B(Ar_{17})$ and $Si(Ar_{18})(Ar_{19})$, however, $T_1$ and $T_2$ are not both a single bond;

$T_3$ is $N(Ar_{20})$ or O;

q and r are each independently an integer of 0 to 4;

$A_2$ and $A_3$ are each independently selected from the group consisting of deuterium, halogen, a cyano group, a nitro group, a $C_1\text{~}C_{40}$ alkyl group, a $C_2\text{~}C_{40}$ alkenyl group, a $C_2\text{~}C_{40}$ alkynyl group, a $C_3\text{~}C_{40}$ cycloalkyl group, a heterocycloalkyl group having 3 to 40 nuclear atoms, a $C_6\text{~}C_{60}$ aryl group, a heteroaryl group having 5 to 60 nuclear atoms, a $C_1\text{~}C_{40}$ alkyloxy group, a $C_6\text{~}C_{60}$ aryloxy group, a $C_3\text{~}C_{40}$ alkylsilyl group, a $C_6\text{~}C_{60}$ arylsilyl group, a $C_1\text{~}C_{40}$ alkylsulfonyl group, a $C_6\text{~}C_{60}$ arylsulfonyl group, a $C_1\text{~}C_{40}$ alkylboron group, a $C_6\text{~}C_{60}$ arylboron group, a $C_6\text{~}C_{60}$ arylphosphanyl group, a $C_6\text{~}C_{60}$ mono or diarylphosphinyl group, a $C_1\text{~}C_{40}$ alkylcarbonyl group, a $C_6\text{~}C_{60}$ arylcarbonyl group and a $C_6\text{~}C_{60}$ arylamine group, and when $A_2$ and $A_3$ are each present in plural numbers, these are the same as or different from each other;

$B_1$ and $Ar_{13}$ to $Ar_{20}$ are each independently selected from the group consisting of hydrogen, deuterium, halogen, a cyano group, a nitro group, a $C_1\text{~}C_{40}$ alkyl group, a $C_2\text{~}C_{40}$ alkenyl group, a $C_2\text{~}C_{40}$ alkynyl group, a $C_3\text{~}C_{40}$ cycloalkyl group, a heterocycloalkyl group having 3 to 40 nuclear atoms, a $C_6\text{~}C_{60}$ aryl group, a heteroaryl group having 5 to 60 nuclear atoms, a $C_1\text{~}C_{40}$ alkyloxy group, a $C_6\text{~}C_{60}$ aryloxy group, a $C_3\text{~}C_{40}$ alkylsilyl group, a $C_6\text{~}C_{60}$ arylsilyl group, a $C_1\text{~}C_{40}$ alkylsulfonyl group, a $C_6\text{~}C_{60}$ arylsulfonyl group, a $C_1\text{~}C_{40}$ alkylboron group, a $C_6\text{~}C_{60}$ arylboron group, a $C_6\text{~}C_{60}$ arylphosphanyl group, a $C_6\text{~}C_{60}$ mono or diarylphosphinyl group, a $C_1\text{~}C_{40}$ alkylcarbonyl group, a $C_6\text{~}C_{60}$ arylcarbonyl group and a $C_6\text{~}C_{60}$ arylamine group, and when $Ar_{13}$ to $Ar_{19}$ are each present in plural numbers, these are the same as or different from each other; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $A_2$, $A_3$, $B_1$ and $Ar_{13}$ to $Ar_{20}$ are each independently unsubstituted or substituted with one or more types of substituents selected from the group consisting of deuterium, halogen, a cyano group, a nitro group, a $C_1\text{~}C_{40}$ alkyl group, a $C_2\text{~}C_{40}$ alkenyl group, a $C_2\text{~}C_{40}$ alkynyl group, a $C_6\text{~}C_{60}$ aryl group, a heteroaryl group having 5 to 60 nuclear atoms, a $C_6\text{~}C_{60}$ aryloxy group, a $C_1\text{~}C_{40}$ alkyloxy group, a $C_6\text{~}C_{60}$ arylamine group, a $C_3\text{~}C_{40}$ cycloalkyl group, a heterocycloalkyl group having 3 to 40 nuclear atoms, a $C_1\text{~}C_{40}$ alkylsilyl group, a $C_1\text{~}C_{40}$ alkylsulfonyl group, a $C_6\text{~}C_{60}$ arylsulfonyl group, a $C_1\text{~}C_{40}$ alkylboron group, a $C_6\text{~}C_{60}$ arylboron group, a $C_6\text{~}C_{60}$ arylphosphanyl group, a $C_6\text{~}C_{60}$ mono or diarylphosphinyl group, a $C_1\text{~}C_{40}$ alkylcarbonyl group, a $C_6\text{~}C_{60}$ arylcarbonyl group and a $C_6\text{~}C_{60}$ arylsilyl group, and when substituted with a plurality of the substituents, these are the same as or different from each other.

10. The compound of claim 1, which is selected from the group consisting of the following compounds:

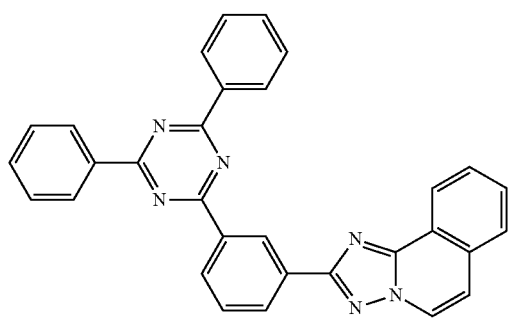

J-1

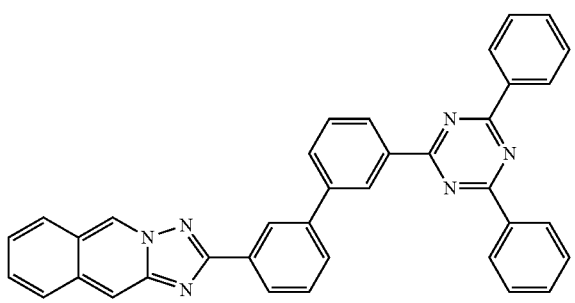

J-2

-continued
J-3
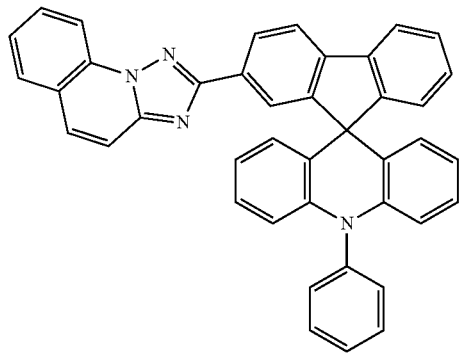
J-4
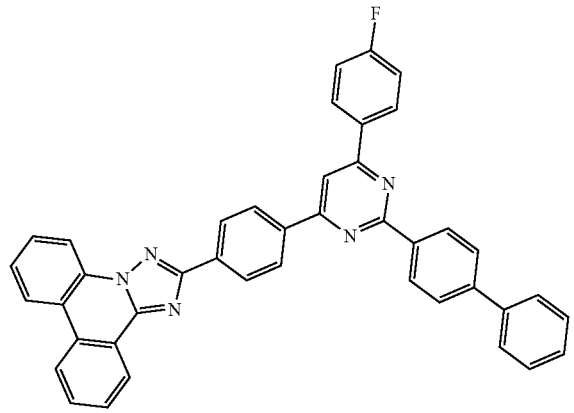
J-5
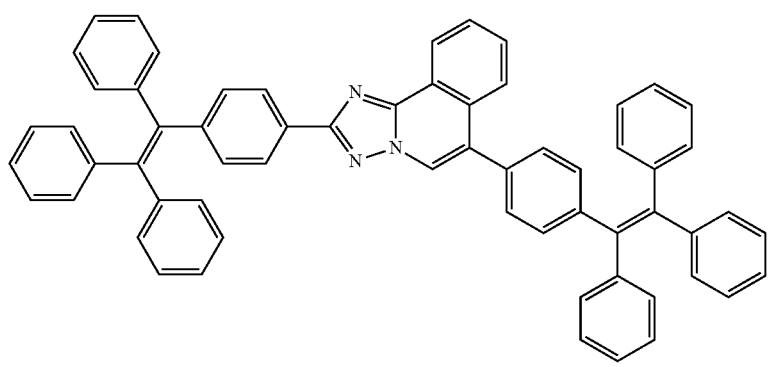
J-6
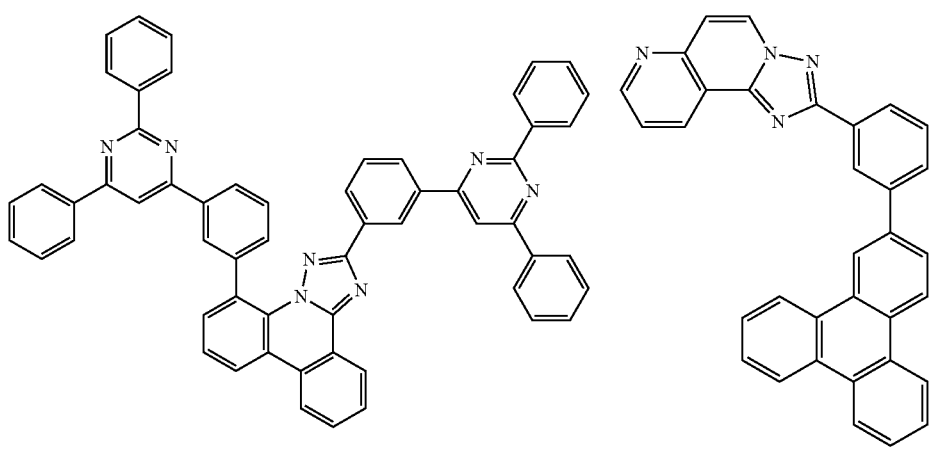
J-7
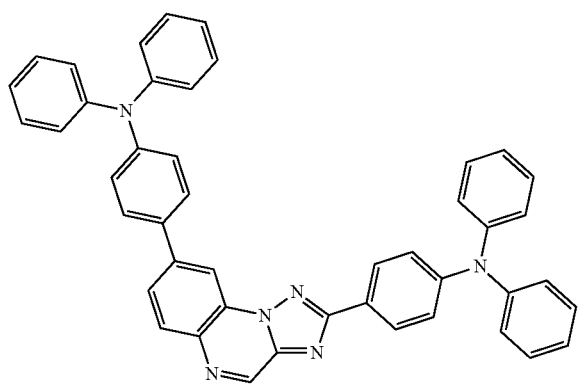
J-8
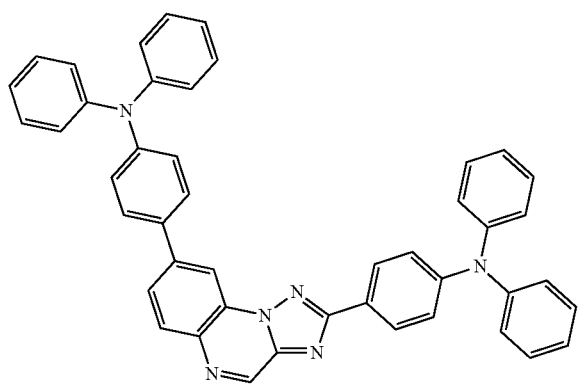
J-9
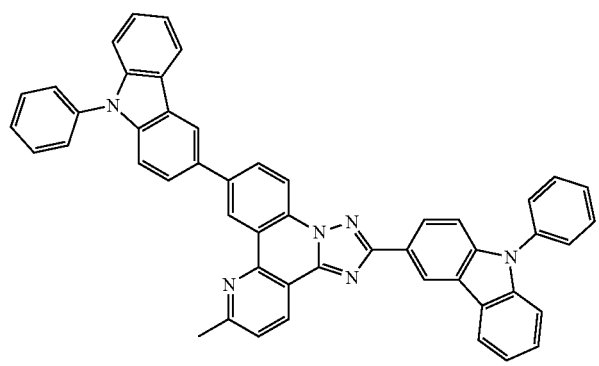

-continued
J-10
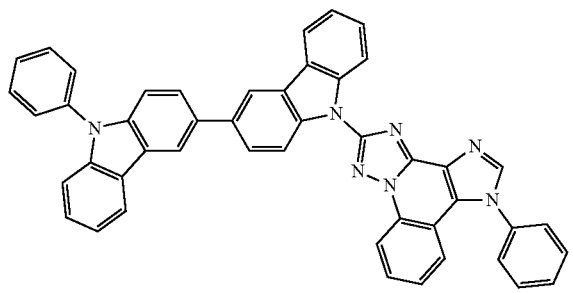
J-11
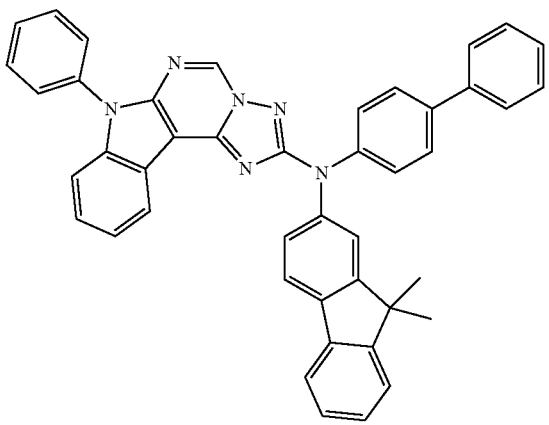
J-12
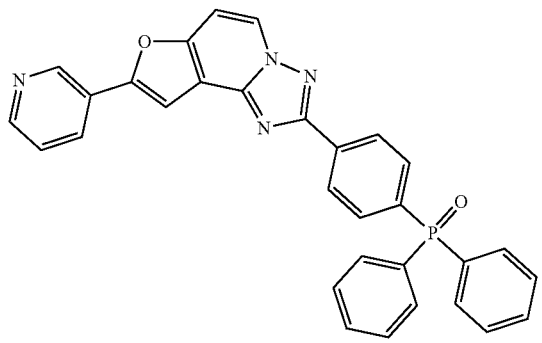
J-13
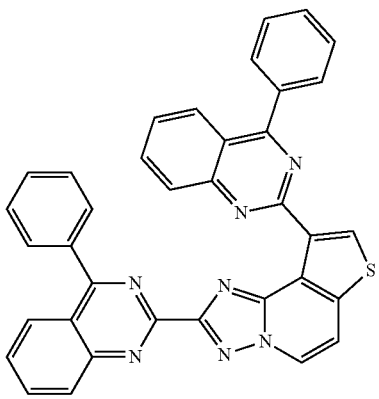
J-14
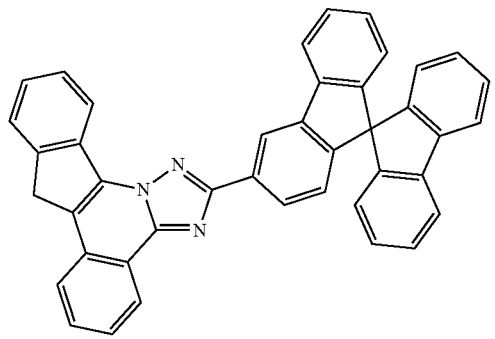
J-15
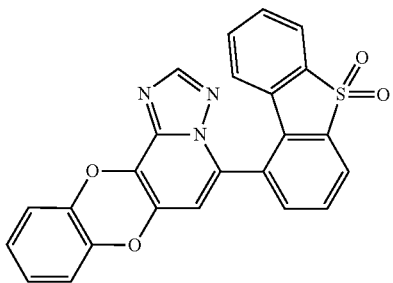
J-16
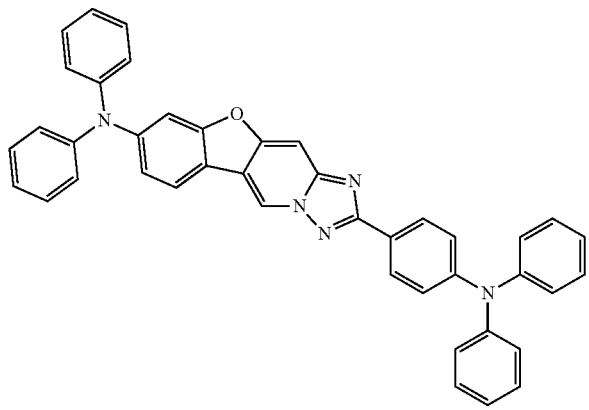
J-17
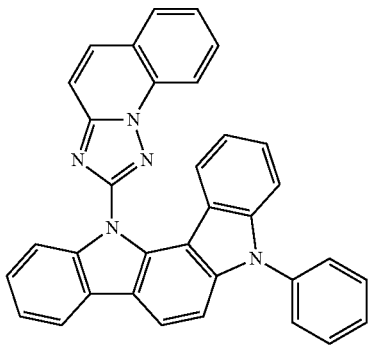

-continued
J-18
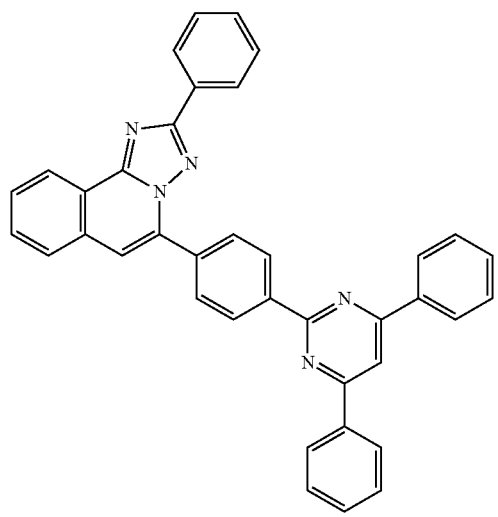
J-19
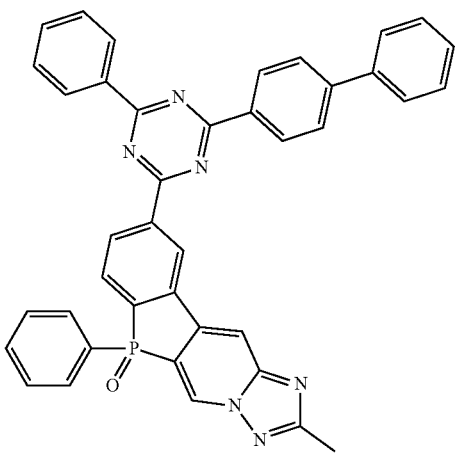
J-20
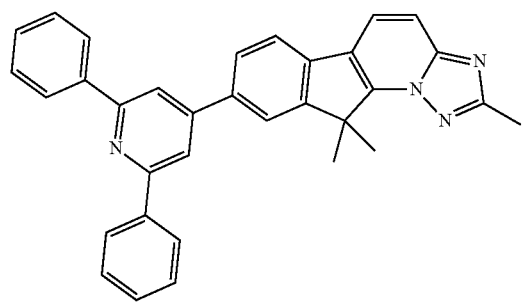
J-21
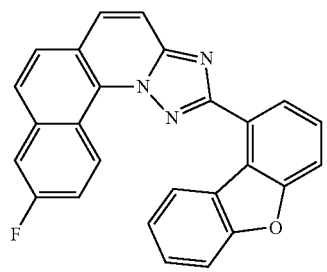
J-22
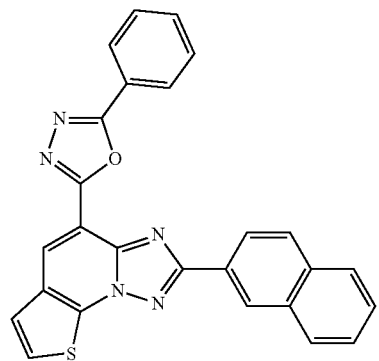
J-23
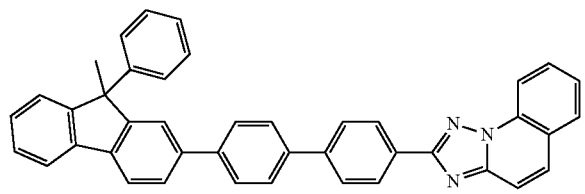
J-24
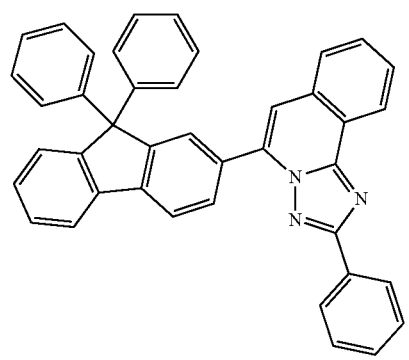
J-25
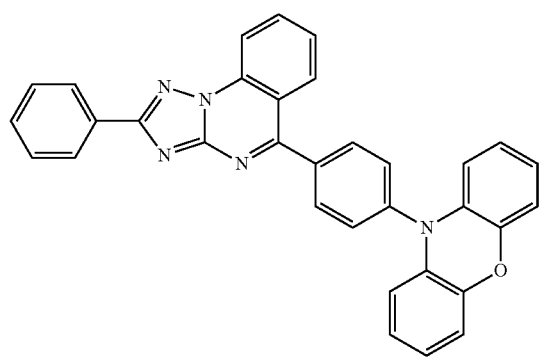

-continued
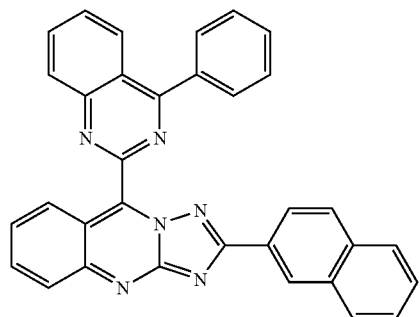
J-26
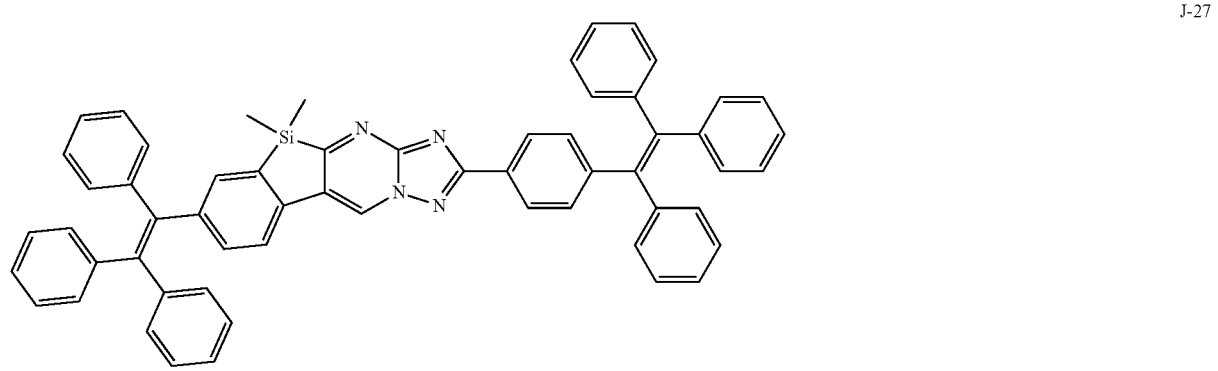
J-27
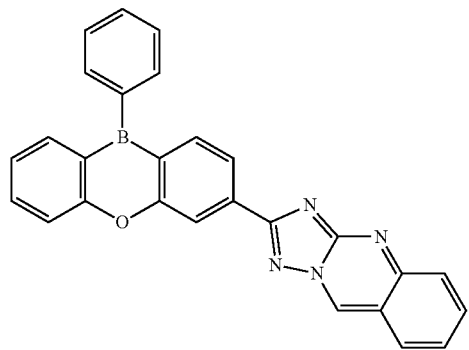
J-28
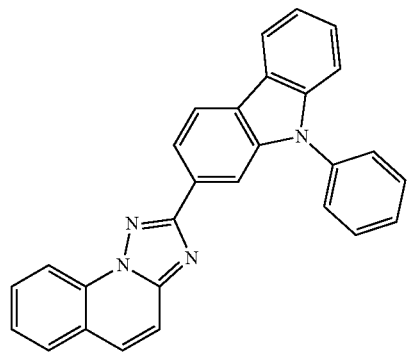
J-29
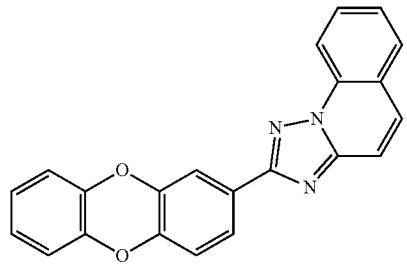
J-30
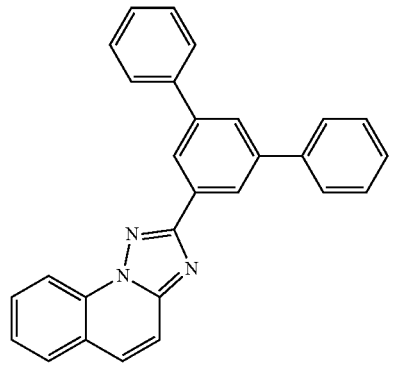
J-31

-continued
J-32
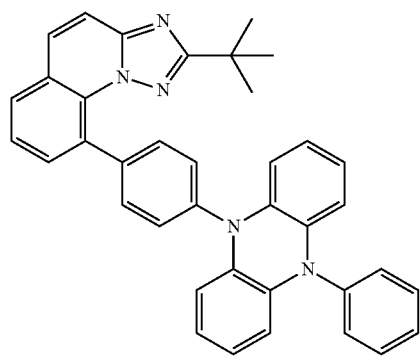
J-33
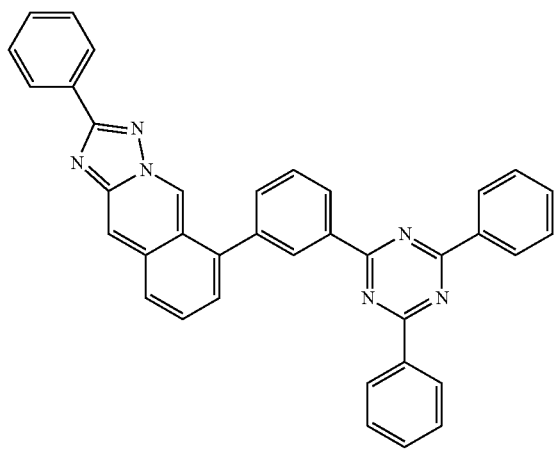
J-34
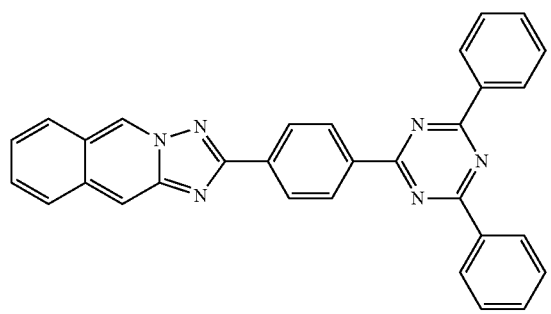
J-35
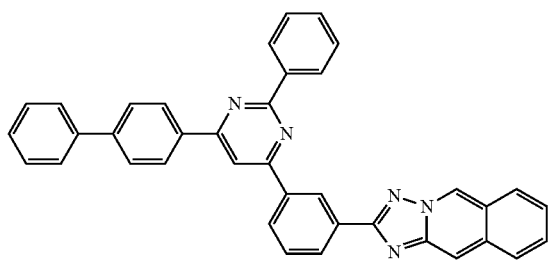
J-36
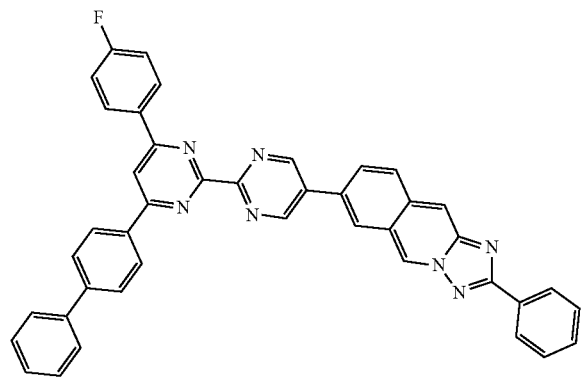
J-37
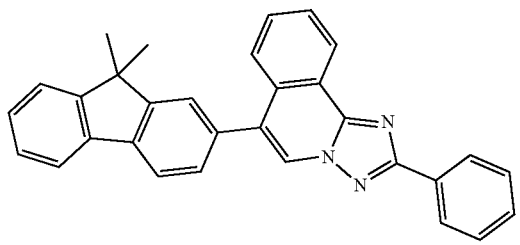
J-38
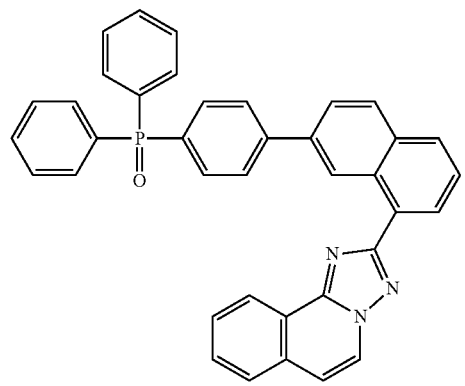
J-39

-continued
J-40
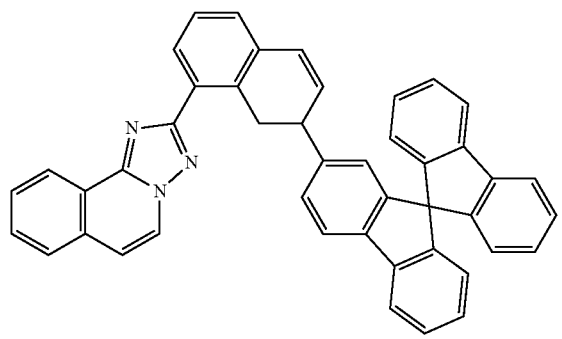
J-41
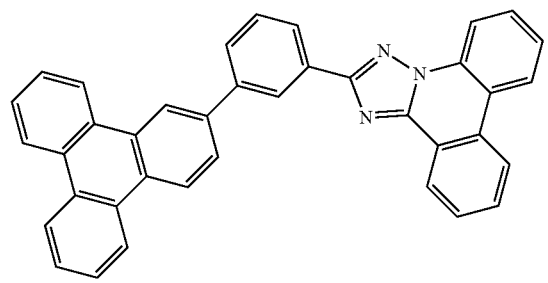
J-42
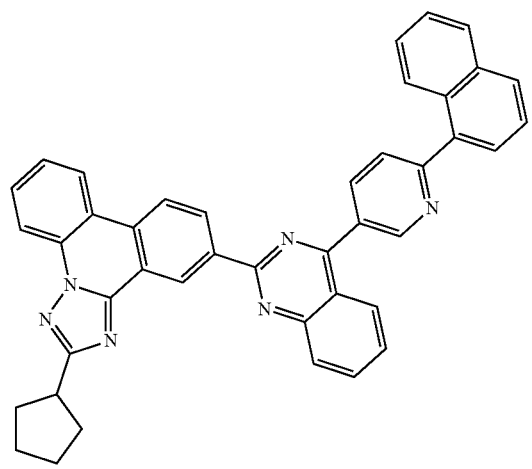
J-43
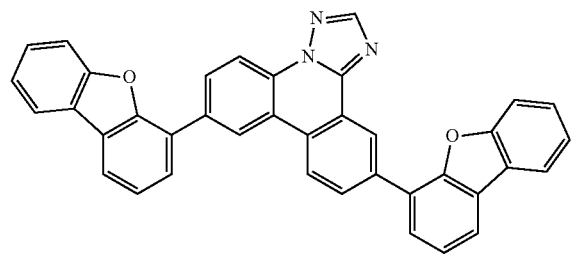
J-44
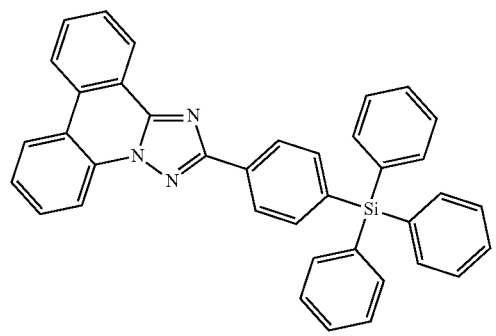
J-45
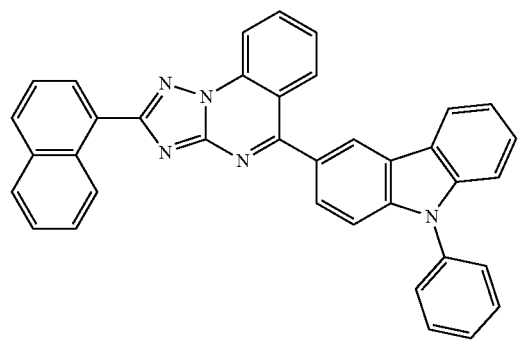
J-46
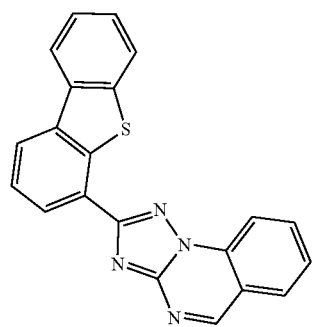
J-47
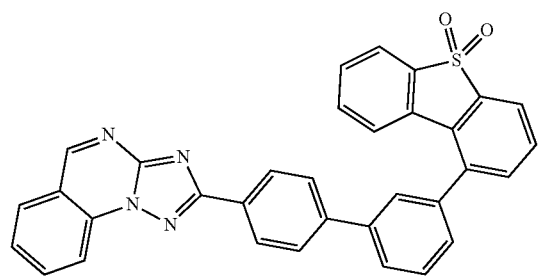

J-48
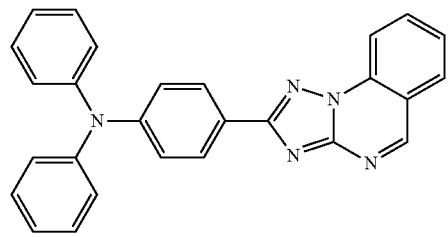
J-49
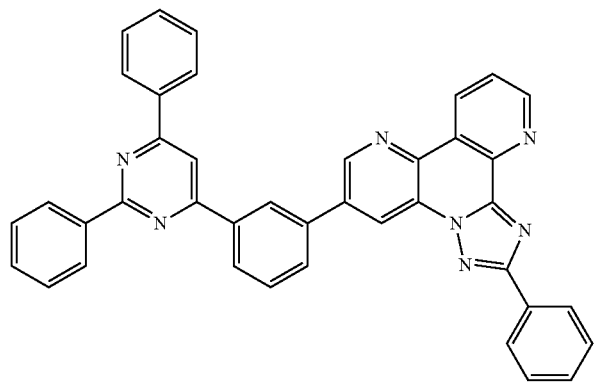
J-50
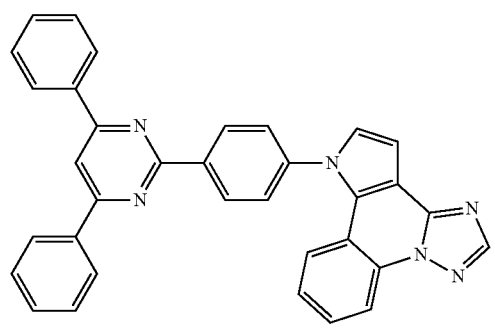
J-51
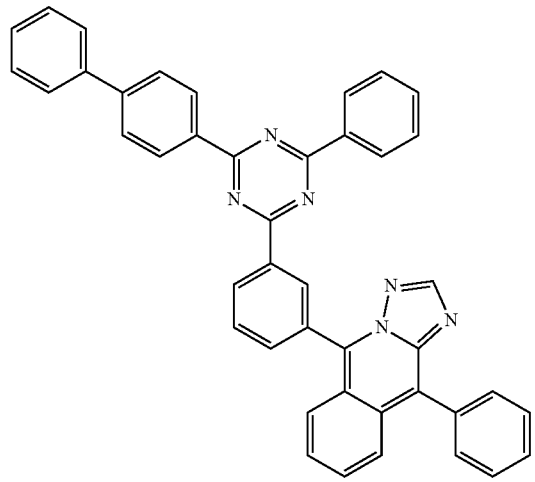
J-52
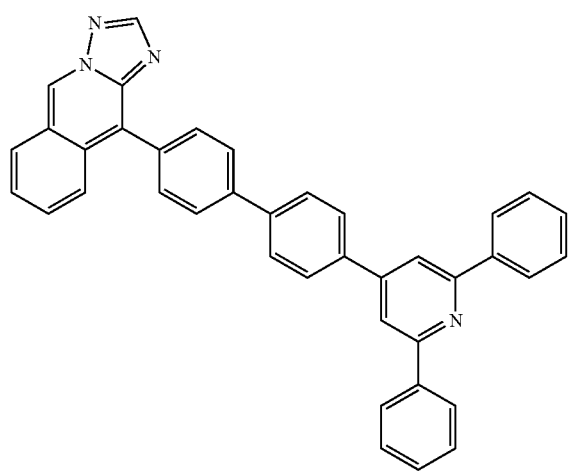
J-57
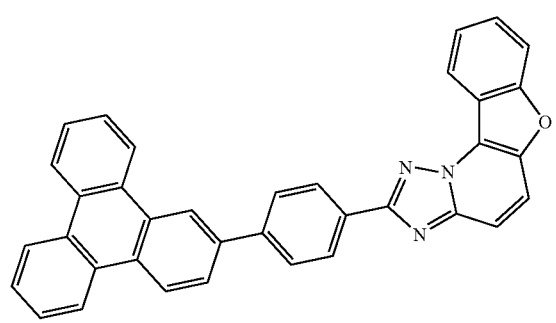

-continued
J-58
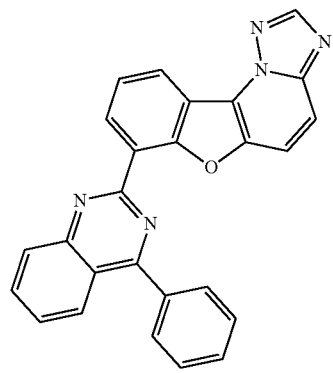
J-59
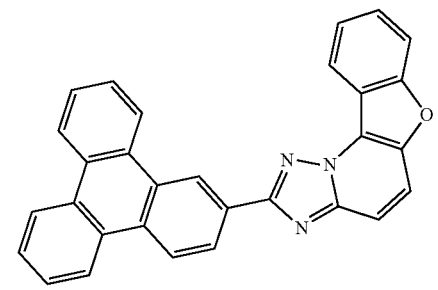
J-60
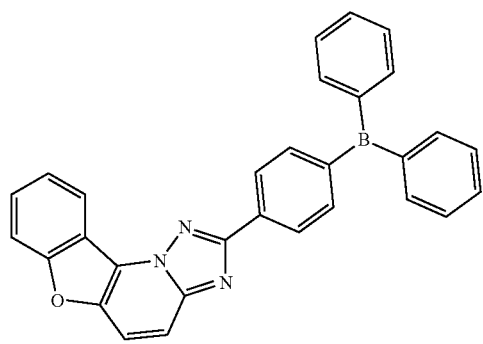
J-61
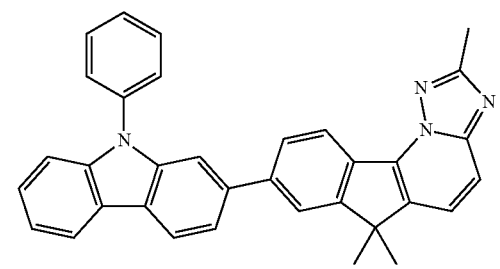
J-62
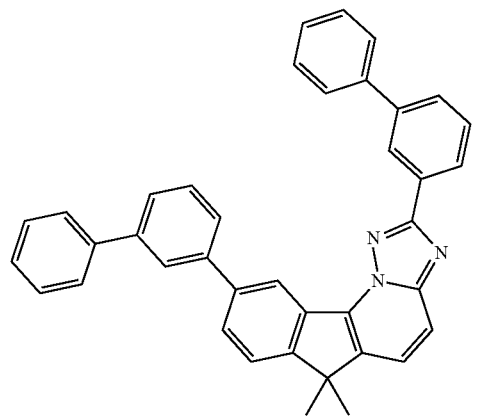
J-63
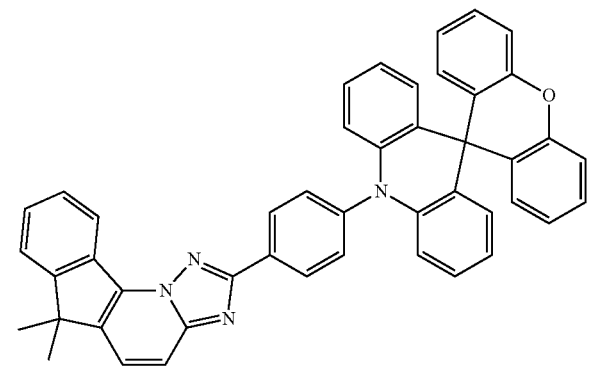
J-64
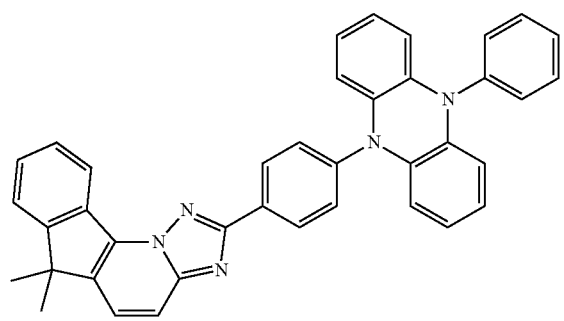
J-65
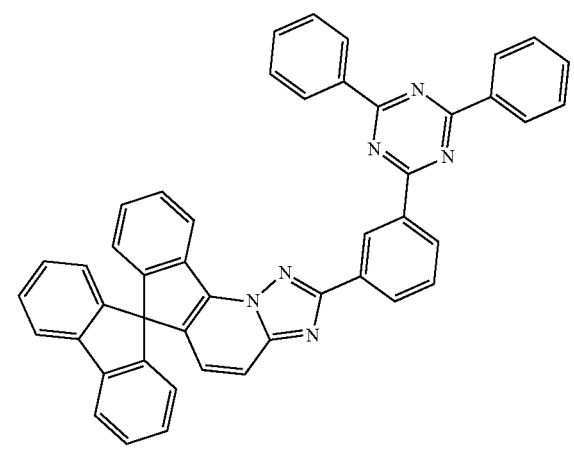

-continued
J-66
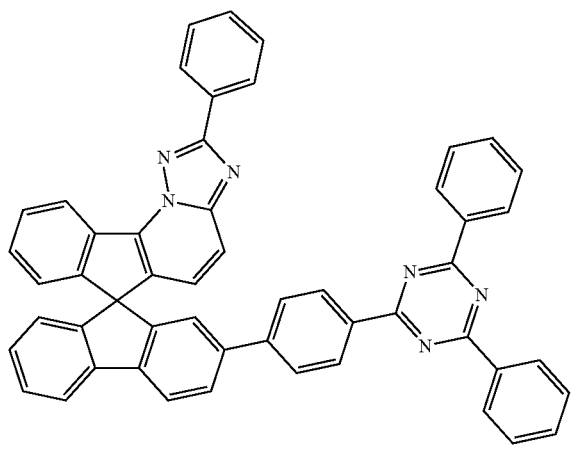
J-69
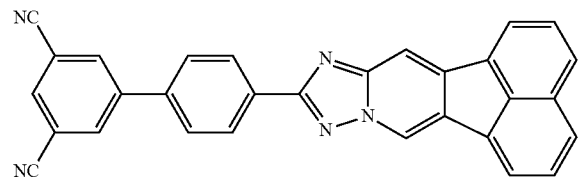
J-70
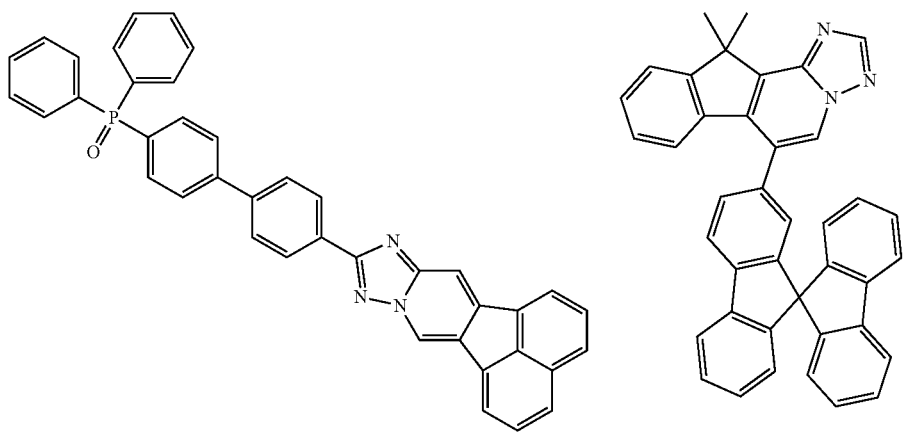
J-72
J-77
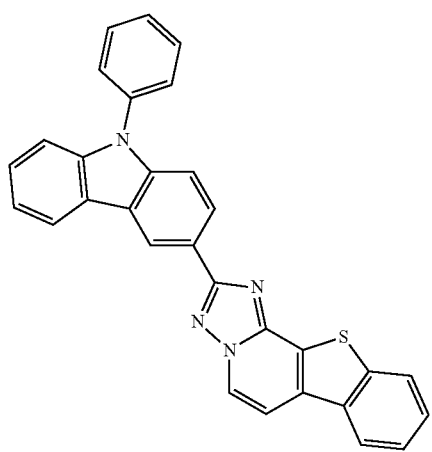
J-78
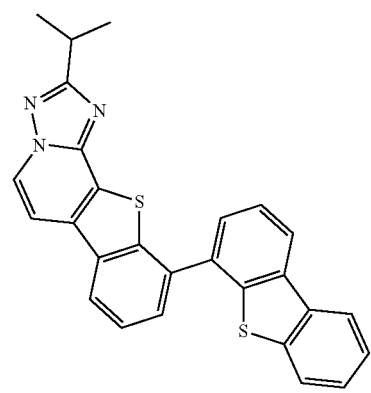

-continued
J-79
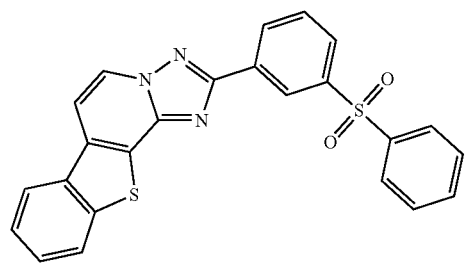
J-80
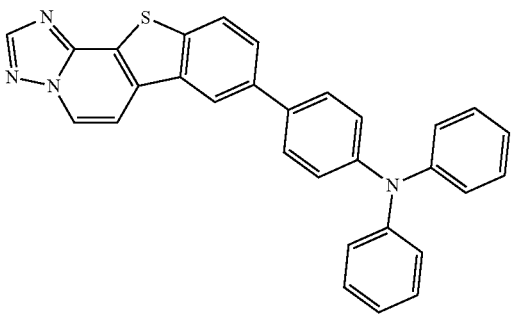
J-81
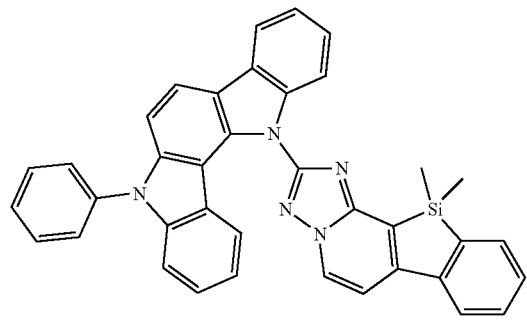
J-82
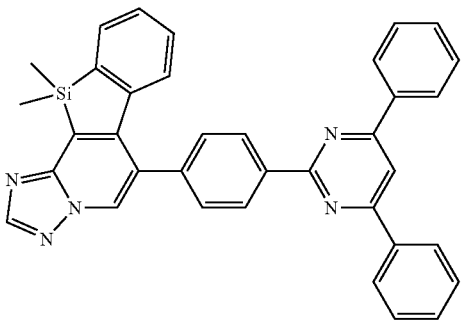
J-83
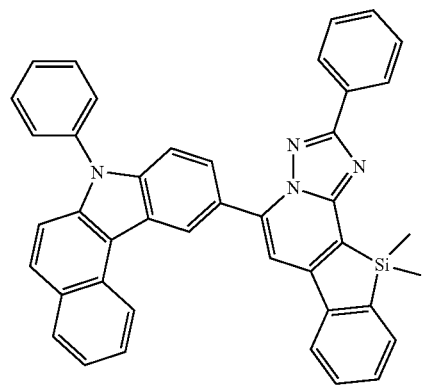
J-84
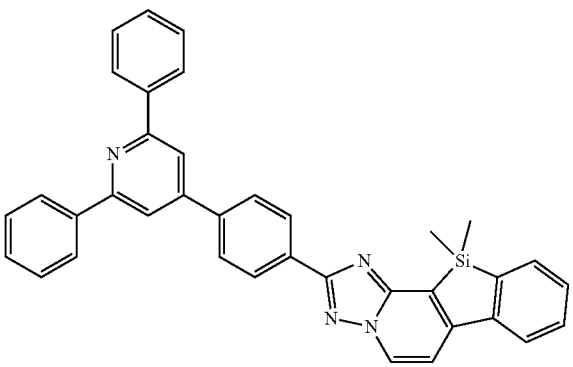
J-85
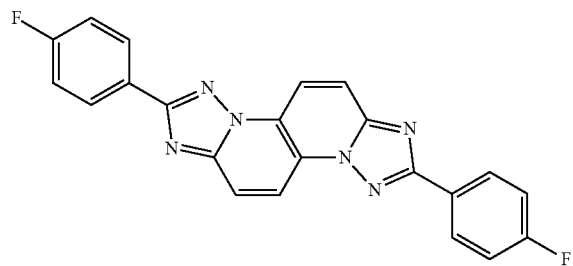
J-86
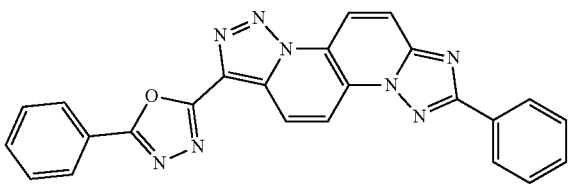

-continued
J-87
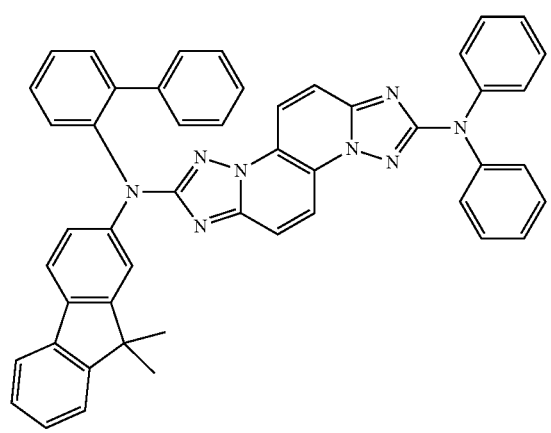
J-88
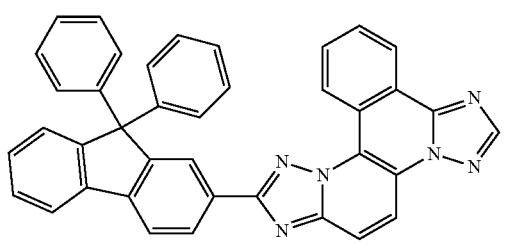
J-89
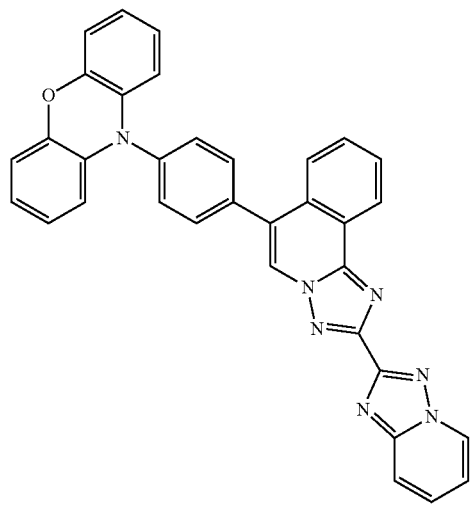
J-90
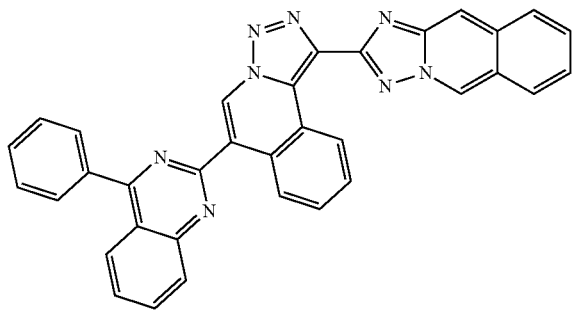
J-91
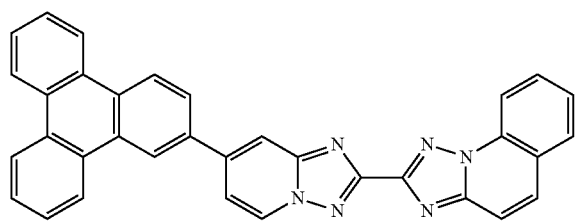
J-92
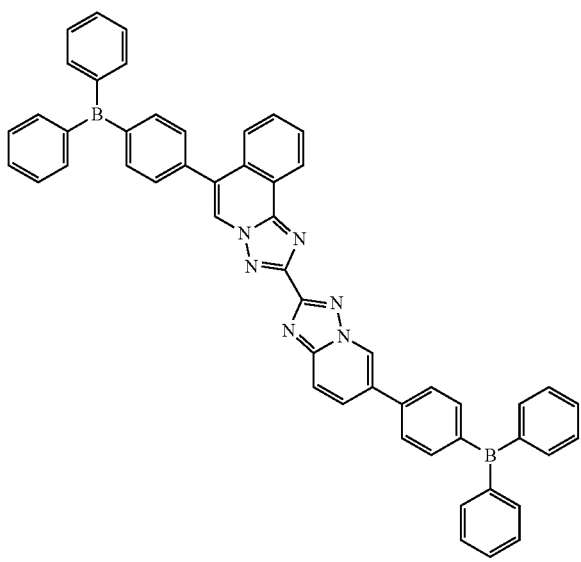

-continued

J-93
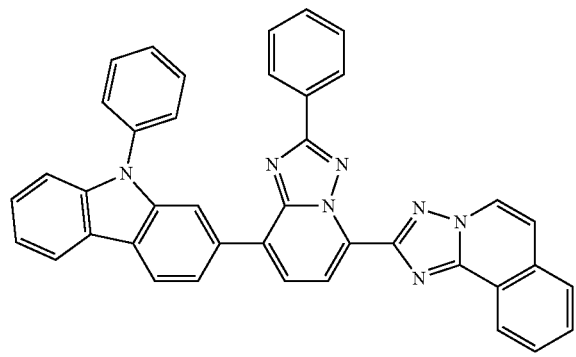

J-94
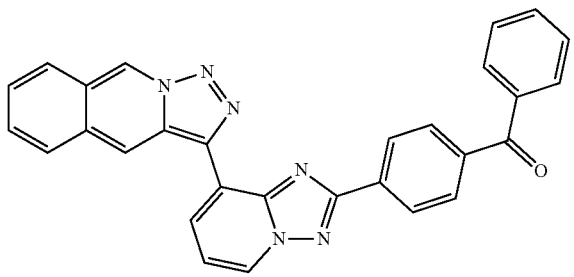

J-95
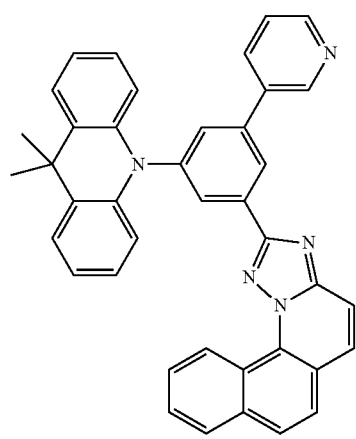

J-96
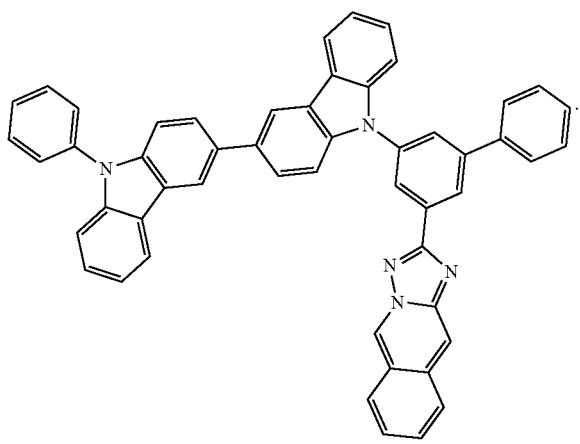

11. An organic electroluminescent device comprising:
(i) an anode;
(ii) a cathode; and
(iii) one or more organic material layers provided between the anode and the cathode,
wherein at least one of the one or more organic material layers includes the compound represented by any one of Chemical Formulae 3 to 6 of claim 1.

12. The organic electroluminescent device of claim 11, wherein the organic material layer including the compound is selected from the group consisting of a hole injection layer, a hole transport layer, an electron transport layer, a hole blocking layer, an electron injection layer, a lifespan improving layer, a light emitting layer and a light emitting auxiliary layer.

* * * * *